(12) United States Patent
Nair et al.

(10) Patent No.: US 9,994,501 B2
(45) Date of Patent: *Jun. 12, 2018

(54) HIGH EFFICIENCY, HIGH PERFORMANCE METAL-ORGANIC FRAMEWORK (MOF) MEMBRANES IN HOLLOW FIBERS AND TUBULAR MODULES

(71) Applicant: Georgia Tech Research Corporation, Atlanta, GA (US)

(72) Inventors: Sankar Nair, Atlanta, GA (US); Kiwon Eum, Atlanta, GA (US); Christopher W. Jones, Atlanta, GA (US); Ali Rownaghi, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/061,964

(22) Filed: Mar. 4, 2016

(65) Prior Publication Data

US 2016/0184798 A1 Jun. 30, 2016

Related U.S. Application Data

(63) Continuation-in-part of application No. 14/231,871, filed on Apr. 1, 2014, now Pat. No. 9,687,791.
(Continued)

(51) Int. Cl.
*C07C 7/144* (2006.01)
*B01D 63/06* (2006.01)
(Continued)

(52) U.S. Cl.
CPC .............. *C07C 7/144* (2013.01); *B01D 63/063* (2013.01); *B01D 67/0051* (2013.01);
(Continued)

(58) Field of Classification Search
CPC .............. B01D 67/0051; B01D 53/228; B01D 2053/224; B01D 63/063; Y10T 29/49345; C07C 7/144; B01J 19/2475
See application file for complete search history.

(56) References Cited

U.S. PATENT DOCUMENTS 5,968,366 A 10/1999 Deckman et al.
6,953,493 B2 10/2005 Nakayama et al.
(Continued)

FOREIGN PATENT DOCUMENTS

CN 1617761 A 5/2005
CN 1914219 A 2/2007
(Continued)

OTHER PUBLICATIONS

Ameloot, et al., *Interfacial synthesis of hollow metal-organic framework capsules demonstrating selective permeability*, Nature Chemistry 3 (May 2011) 382-387.
(Continued)

*Primary Examiner* — Lessanework Seifu
(74) *Attorney, Agent, or Firm* — Adams and Reese LLP

(57) ABSTRACT

A reactor cell for measuring gas and liquid permeation is disclosed. A hollow fiber is supported by and sealed into a first hole and a second hole of the reactor module. The first and second ends of the hollow fiber are sealed with a sealing solution. Methods for making and using the reactor cell are also disclosed. As made and used, the reactor cell further comprises a molecular sieving membrane that is uniform and free of defects grown on an inner bore surface of the hollow fiber.

30 Claims, 43 Drawing Sheets
(27 of 43 Drawing Sheet(s) Filed in Color)

Related U.S. Application Data

(60) Provisional application No. 61/913,592, filed on Dec. 9, 2013, provisional application No. 61/820,489, filed on May 7, 2013.

(51) Int. Cl.
   *B01D 67/00* (2006.01)
   *B01D 69/08* (2006.01)

(52) U.S. Cl.
   CPC ............ *B01D 69/08* (2013.01); *Y02P 20/582* (2015.11); *Y10T 29/49345* (2015.01)

(56) References Cited

U.S. PATENT DOCUMENTS

| | | |
|---|---|---|
| 7,014,680 B2 | 3/2006 | Nakayama et al. |
| 7,306,647 B2 | 12/2007 | Miller et al. |
| 7,494,610 B2 | 2/2009 | Yeung et al. |
| 7,553,352 B2 | 6/2009 | Mueller et al. |
| 7,880,026 B2 | 2/2011 | Ni et al. |
| 7,973,090 B2 | 7/2011 | Suzuki et al. |
| 8,042,695 B2 | 10/2011 | Ishibashi |
| 8,123,834 B2 | 2/2012 | Masel et al. |
| 8,132,678 B2 | 3/2012 | Liu et al. |
| 8,269,029 B2 | 9/2012 | Masel et al. |
| 8,302,782 B2 | 11/2012 | Falconer et al. |
| 8,518,153 B2 | 8/2013 | Ryan et al. |
| 8,673,057 B2 | 3/2014 | Zhou et al. |
| 8,725,482 B2 | 5/2014 | Haldoupis et al. |
| 2002/0003105 A1 | 1/2002 | McEvoy |
| 2002/0031303 A1 | 3/2002 | Wang |
| 2004/0058224 A1 | 3/2004 | Eshraghi et al. |
| 2004/0139908 A1 | 7/2004 | Bowe et al. |
| 2004/0173094 A1 | 9/2004 | Nakayama et al. |
| 2005/0124819 A1 | 6/2005 | Yaghi et al. |
| 2005/0204916 A1 | 9/2005 | Falconer et al. |
| 2005/0229779 A1 | 10/2005 | Nakayama et al. |
| 2005/0233945 A1 | 10/2005 | Brown et al. |
| 2006/0107830 A1 | 5/2006 | Miller et al. |
| 2006/0201884 A1 | 9/2006 | Kulprathipanja et al. |
| 2007/0022877 A1 | 2/2007 | Marand et al. |
| 2007/0112189 A1 | 5/2007 | Ikeda et al. |
| 2007/0244347 A1 | 10/2007 | Ying et al. |
| 2008/0047432 A1 | 2/2008 | Nonaka et al. |
| 2008/0177098 A1 | 7/2008 | Bahnmuller et al. |
| 2008/0214686 A1 | 9/2008 | Suzuki et al. |
| 2008/0261101 A1 | 10/2008 | de Figueiredo Gomes et al. |
| 2008/0287413 A1 | 11/2008 | Aslund et al. |
| 2009/0004084 A1 | 1/2009 | Bell et al. |
| 2009/0011926 A1 | 1/2009 | Yajima et al. |
| 2009/0060839 A1 | 3/2009 | Boyes et al. |
| 2009/0111959 A1 | 4/2009 | Cao et al. |
| 2009/0114089 A1 | 5/2009 | Liu et al. |
| 2009/0126570 A1 | 5/2009 | Liu et al. |
| 2009/0131643 A1 | 5/2009 | Ni et al. |
| 2009/0152755 A1 | 6/2009 | Liu et al. |
| 2009/0155464 A1 | 6/2009 | Liu et al. |
| 2009/0211440 A1 | 8/2009 | Reyes et al. |
| 2010/0006503 A1 | 1/2010 | Bratton et al. |
| 2010/0071559 A1 | 3/2010 | Miachon et al. |
| 2010/0072424 A1 | 3/2010 | Petoud et al. |
| 2010/0132549 A1 | 6/2010 | Yaghi et al. |
| 2010/0144512 A1 | 6/2010 | Uchikawa et al. |
| 2010/0226991 A1 | 9/2010 | Horcajada-Cortes et al. |
| 2011/0158923 A1 | 6/2011 | Galeone et al. |
| 2011/0160039 A1 | 6/2011 | Himeno et al. |
| 2011/0298115 A1 | 12/2011 | Celaya et al. |
| 2011/0319630 A1 | 12/2011 | Yaghi et al. |
| 2012/0003475 A1 | 1/2012 | Benin et al. |
| 2012/0058302 A1 | 3/2012 | Eggenspieler et al. |
| 2012/0070904 A1 | 3/2012 | Stoddart et al. |
| 2012/0202006 A1 | 8/2012 | Rimer |
| 2012/0310018 A1 | 12/2012 | Lai et al. |
| 2013/0064747 A1 | 3/2013 | Zhou et al. |
| 2013/0157837 A1 | 6/2013 | Banerjee et al. |
| 2013/0197235 A1 | 8/2013 | Thompson et al. |

FOREIGN PATENT DOCUMENTS

| | | |
|---|---|---|
| CN | 103201016 B | 9/2015 |
| JP | 2007045691 | 2/2007 |
| WO | WO-2005099885 A1 | 10/2005 |
| WO | WO-2007139766 A2 | 12/2007 |
| WO | WO-2010103856 | 9/2010 |
| WO | WO-2012074487 A1 | 6/2012 |
| WO | WO-2012138418 A1 | 10/2012 |
| WO | WO-2013020968 A2 | 2/2013 |

OTHER PUBLICATIONS

Brown, et al., *Continuous polycrystalline zeolitic imidazolate framework-90 membranes on polymeric hollow fibers*, Angew. Chem. 124 (2012) 10767-10770.

Buonomenna, *Membrane processes for a sustainable industrial growth*, RSC Adv. 3 (2013) 5694-5740.

Bux, et al., *Oriented zeolitic imidazolate framework-8 membrane with sharp $H_2/C_3H_8$ molecular sieve separation*, Chem. Mater. 23 (2011) 2262-2269.

Cao, et al., *Growth of uniformly oriented silica MFI and BEA zeolite films on substrates*, Science 334 (Dec. 16, 2001) 1533-1538.

Choi, et al., *Grain boundary defect elimination in a zeolite membrane by rapid thermal processing*, Science 325 (Jul. 31, 2009) 590-593.

Gascon, et al., *Accelerated synthesis of all-silica DD3R and its performance in the separation of propylene/propane mixtures*, Microporous & Mesoporous Materials 115 (2008) 585-593.

Gascon, et al., *Practical approach to zeolitic membranes and coatings: State of the art, opportunities, barriers, and future perspectives*, Chem. Mater. 24 (2012) 2829-2844.

Huang, et al., *Steam-stable zeolitic imidazolate framework ZIF-90 membrane with hydrogen selectivity through covalent functionalization*, J. Am. Chem. Soc. 132(44) (2010) 15562-15564.

Jang, et al., *Modified mesoporous silica gas separation membranes on polymeric hollow fibers*, Chem. Mater. 23 (2011) 3025-3028.

Kwon, et al., *Highly propylene-selective supported zeolite-imidazolate framework (ZIF-8) membranes synthesized by rapid microwave-assisted seeding and secondary growth*, Chem. Commun. 49 (2013) 3854-3856.

Li, et al., *Zeolitic imidazolate frameworks for kinetic separation of propane and propene*, J. Am. Chem. Soc. 131(30) (2009) 10368-10369.

Pan, et al., *Effective separation of propylene/propane binary mixtures by ZIF-8 membranes*, J. Membrane Science 390-391 (2012) 93-98.

Pan, et al., *Sharp separation of C2/C3 hydrocarbon mixtures by zeolitic imidazolate framework-8 (ZIF-8) membranes synthesized in aqueous solutions*, Chem. Commun. 47(37) (Oct. 7, 2011) 10275-10277.

Pan, et al., *Synthesis of ceramic hollow fiber supported zeolitic imidazolate framework-8 (ZIF-8) membranes with high hydrogen permeability*, J. Membrane Science 421-422 (2012) 292-298.

Park, et al., *Exceptional chemical and thermal stability of zeolitic imidazolate frameworks*, PNAS 103(27) (Jul. 5, 2006) 10186-10191.

Pera-Titus, et al., *Preparation of inner-side tubular zeolite NaA membranes in a semi-continuous synthesis system*, J. Membrane Science 278 (2006) 401-409.

Shah, et al., *Current status of metal-organic framework membranes for gas separations: Promises and challenges*, Ind. Eng. Chem. Res. 51 (2012) 2179-2199.

Thompson, et al., *Hybrid zeolitic imidazolate frameworks: Controlling framework porosity and functionality by mixed-linker synthesis*, Chem. Mater. 24 (2012) 1930-1936.

Tsapatsis, *Toward high-throughput zeolite membranes*, Science 334 (Nov. 11, 2011) 767-768.

Varoon, et al., *Dispersible exfoliated zeolite nanosheets and their application as a selective membrane*, Science 334 (Oct. 7, 2011) 72-75.

PCT Aug. 22, 2014 International Search Report and Written Opinion issued in International Application PCT/US14/133169.

(56) References Cited

OTHER PUBLICATIONS

Aug. 3, 2012 Office Action/Non-Final Rejection mailed in U.S. Appl. No. 12/971,132, filed Dec. 17, 2010.
Dec. 18, 2012 Response to Office Action dated Aug. 3, 2012 filed in U.S. Appl. No. 12/971,132, filed Dec. 17, 2010.
Jan. 28, 2013 Office Action/Final Rejection mailed in U.S. Appl. No. 12/971,132, filed Dec. 17, 2010.
Jun. 24, 2013 Response to Final Office Action dated Jan. 28, 2013 with Declaration filed in U.S. Appl. No. 12/971,132, filed Dec. 17, 2010.
Aug. 14, 2013 Office Action/Non Final Rejection mailed in U.S. Appl. No. 12/971,132, filed Dec. 17, 2010.
Feb. 11, 2014 Response to Office Action dated Aug. 14, 2013 with Declaration filed in U.S. Appl. No. 12/971,132, filed Dec. 17, 2010.
Mar. 3, 2014 Notice of Allowance/Allowability with Examiner's Amendment and Statement of Reasons for Allowance mailed in U.S. Appl. No. 12/971,132, filed Dec. 17, 2010.
Oct. 31, 2013 Office Action/Non-Final Rejection mailed in U.S. Appl. No. 13/396,411, filed Feb. 14, 2012.
Jan. 17, 2014 Response to Office Action dated Oct. 31, 2013 filed in U.S. Appl. No. 13/396,411, filed Feb. 14, 2012.
Apr. 9, 2014 Final Office Action mailed in U.S. Appl. No. 13/396,411, filed Feb. 14, 2012.
Jun. 3, 2014 Response to Final Office Action filed in U.S. Appl. No. 13/396,411, filed Feb. 14, 2012.
Jun. 11, 2014 Notice of Allowance/Allowability with Examiner's Amendment/Comment mailed in U.S. Appl. No. 13/396,411, filed Feb. 14, 2012.
Dec. 19, 2013 Notice of Allowance/Allowability with Examiner's Amendment/Comment mailed in U.S. Appl. No. 13/399,645, filed Feb. 17, 2012.
Apr. 19, 2013 Office Action Non-Final mailed in U.S. Appl. No. 13/209,957, filed Aug. 15, 2011.
Jun. 14, 2013 Response to Office Action dated Apr. 19, 2013 in U.S. Appl. No. 13/209,957, filed Aug. 15, 2011.
Jul. 11, 2013 Notice of Allowance / Allowability mailed in U.S. Appl. No. 13/209,957, filed Aug. 15, 2011.
Gordillo, et al., *Site percolation in zeolitic frameworks*, Zeolites 15 (1995) 656-659.
Moloy, et al., *High-silica zeolites: A relationship between energetics and internal surface areas*, Microporous & Mesoporous Materials 54 (2002) 1-13.
Nair, *Nanoscopic metal oxide objects via controlled creation and rearrangement of amorphous nanoparticles*, presented Dec. 11, 2007, School of Chemical & Biomolecular Engineering Georgia Institute of Technology, Atlanta, GA 30332-0100.
Skoulidas, et al., *Self-diffusion and transport diffusion of light gases in metal-organic framework materials assessed using molecular dynamics simulations*, J. Phys. Chem. B 109 (2005) 15760-15768.
Chen, et al., *Interwoven metal-organic framework on a periodic minimal surface with extra-large pores*, Science 291 (2001) 1021-1023.
Eddaoudi, et al., *Design and synthesis of metal-carboxylate frameworks with permanent microporosity*, Topics in Catalysis 9 (1999) 105-111.
Foster, et al., *A geometric solution to the largest free-sphere problem in zeolite frameworks*, Microporous & Mesoporous Materials 90(1-3) (2006) 32-38.
Hoshen, et al., *Percolation and cluster distribution. I. Cluster multiple labeling technique and critical concentration algorithm*, Physical Review B 14(8) (1976) 3438.
Keskin, et al., *Efficient methods for screening of metal organic framework membranes/or gas separations using atomically detailed models*, Langmuir 25(19) (2009) 11786-11795.
Li, et al., *Design and synthesis of an exceptionally stable and highly porous metal-organic framework*, Nature 402 (1999) 276-279.
Ockwig, et al., *Reticular chemistry: Occurrence and taxonomy nets and grammar for the design of frameworks*, Acc. Chem. Res. 38(3) (2005) 176-182.

Seki, *Dynamic channels of a porous coordination polymer responding to external stimuli*, Phys. Chem. Chem. Phys. 4(10) (2002) 1968-1971.
Yaghi, et al., *Reticular synthesis and the design of new materials*, Nature 423 (2003) 705-714.
PCT Feb. 24, 2011 International Search Report and Written Opinion mailed in International Patent Application PCT/US2010/060945.
CN Mar. 14, 2014 Notification of the First Office Action mailed in Chinese Patent Application 201080057358.8 (with English Translation).
CN Jul. 28, 2014 Response to First Office Action dated Mar. 14, 2014 filed in Chinese Patent Application 201080057358.8 (with English Translation).
CN Sep. 16, 2014 Notification of the Second Office Action mailed in Chinese Patent Application 201080057358.8 (with English Translation).
JP Nov. 26, 2013 Office Action mailed in Japanese Patent Application 2012-543346 (with English Translation).
JP Jul. 17, 2014 Examiner's Decision of Refusal mailed in Japanese Patent Application 2012-543346 (with English Translation).
KR Feb. 10, 2014 Notice of Submission of Opinion/Office Action mailed in Korean Patent Application 10-2012-7013862 (with English Translation).
Den Exter, M.J., et al., *Separation of permanent gases on the all-silica 8-ring clathrasil DD3R*, (Weitkamp, J., et al., eds. Zeolites and Related Microporous Materials: State of the Art 1994), Studies in Surface Science and Catalysis 84 (1994) 1159-66.
Gies, H., *Studies on clathrasils. IX crystal structure of deca-dodecasil 3R, the missing link between zeolites and clathrasils*, Zeitschrift für Kristallographie 175 (1986) 93-104.
Himeno, Shuji, et al., *Characterization and selectivity for methane and carbon dioxide adsorption on the all-silica DD3R zeolite*, Micropor. Mesopor. Mater. 98 (2007) 62-69.
Tomita, Toshihiro, et al., *Gas separation characteristics of DDR type zeolite membrane*, Micropor. Mesopor. Mater. 68 (2004) 71-75.
Yang, Qi-Liang, et al., *Synthesis of DDR-type zeolite in fluoride medium*, Chinese Journal of Inorganic Chemistry 25(2) (2009) 191-194.
Aguado, Sonia, et al., *Facile synthesis of an ultramicroporous MOF tubular membrane with selectivity towards $CO_2$*, New J. Chem. 35 (2011) 41-44.
Bae, Tae-Hyun, et al., *A high-performance gas-separation membrane containing submicrometer-sized metal-organic framework crystals*, Angew. Chem. Int. Edit. 49 (2010) 9863-66.
Baker, Richard W., *Future directions of membrane gas separation technology*, Ind. Eng. Chem. Res. 41(6) (2002) 1393-411.
Baker, Richard W. and Kaaeid Lokhandwala, *Natural gas processing with membranes: An overview*, Ind. Eng. Chem. Res. 47(7) (2008) 2109-21.
Brar, Tejinder, et al., *Control of crystal size and distribution of zeolite A*, Ind. Eng. Chem. Res. 40 (2001) 1133-39.
Bux, Helge, et al., *Zeolitic imidazolate framework membrane with molecular sieving properties by microwave-assisted solvothermal synthesis*, J. Am. Chem. Soc. 131(44) (2009) 16000-01.
Caro, Jüergen and Manfred Noack, *Zeolite membranes—Recent developments and progress*, Micropor. Mesopor. Mater. 115 (2008) 215-33.
Carreon, Moises A., et al., *Alumina-supported SAPO-34 membranes for $CO_2/CH_4$ separation*, J. Am. Chem. Soc. 130(16) (2008) 5412-13.
Centrone, Andrea, et al., *Growth of metal-organic frameworks on polymer surfaces*, J. Am. Chem. Soc. 132(44) (2010) 15687-91.
Chen, Banglin, et al., *A microporous metal-organic framework for gas-chromatographic separation of alkanes*, Agnew. Chem. Int. Ed. 45 (2006) 1390-93.
Chiu, W. V., et al., *Post-synthesis defect abatement of inorganic membranes for gas separation*, J. Membr. Sci. 377 (2011) 182-90.
Cui, Ying, et al., *Preparation and gas separation performance of zeolite T membrane*, J. Mater. Chem. 14(5) (2004) 924-32.
Cui, Ying, et al., *Preparation and gas separation properties of zeolite T membrane*, Chem. Comm. 17 (2003) 2154-55.

(56) References Cited

OTHER PUBLICATIONS

Favre, Eric, *Carbon dioxide recovery from post-combustion processes: Can gas permeation membranes compete with absorption?*, J. Membr. Sci. 294 (2007) 50-59.
Forster, Paul M., et al., *A high-throughput investigation of the role of pH, temperature, concentration, and time on the synthesis of hybrid inorganic-organic materials*, Angew. Chem. Int. Ed. 44 (2005) 7608-11.
Ge, Qingqin, et al., *High-performance zeolite NaA membranes on polymer-zeolite composite hollow fiber supports*, J. Am. Chem. Soc. 131(47) (2009) 17056-57.
Hao, Ji Hua and Shichang Wang, *Influence of quench medium on the structure and gas permeation properties of cellulose acetate membranes*, J. Appl. Polym. Sci. 68(8) (1998) 1269-76.
Heng, Samuel, et al., *Low-temperature ozone treatment for organic template removal from zeolite membrane*, J. Membr. Sci. 243 (2004) 69-78.
Himeno, Shuji, et al., *Synthesis and permeation properties of a DDR-type zeolite membrane for separation of $CO_2/CH_4$ gaseous mixtures*, Ind. Eng. Chem. Res. 46(21) (2007) 6989-97.
Huang, Aisheng, & Jürgen Caro, *Covalent post-functionalization of zeolitic imidazolate framework ZIF-90 membrane for enhanced hydrogen selectivity*, Angew. Chem. Int. Ed. 50 (2011) 4979-82.
Huang, Aisheng, et al., *Molecular-sieve membrane with hydrogen permselectivity: ZIF-22 in LTA topology prepared with 3-aminopropyltriethoxysilane as covalent linker*, Angew. Chem. Int. Ed. 49 (2010) 4958-61.
Huang, Aisheng and Jürgen Caro, *Cationic polymer used to capture zeolite precursor particles for the facile synthesis of oriented zeolite LTA molecular sieve membrane*, Chem. Mater. 22(15) (2010) 4353-55.
Husain, Shabbir, Mixed Matrix Dual Layer Hollow Fiber Membranes for Natural Gas Separation, Dissertation, Georgia Institute of Technology, Atlanta, GA, 2006, 48-49.
Jee, Sang Eun and David S. Sholl, *Carbon dioxide and methane transport in DDR zeolite: Insights from molecular simulations into carbon dioxide separations in small pore zeolites*, J. Am. Chem. Soc. 131(22) (2009) 7896-7904.
Jie, Xingming, et al., *Gas permeation performance of cellulose hollow fiber membranes made from the cellulose/N-methylmorpholine-N-oxide/$H_2O$ system*, J. Appl. Polym. Sci. 91(3) (2004) 1873-80.
Kanezashi, Masakoto, et al., *Gas permeation through DDR-type zeolite membranes at high temperatures*, AlChE J. 54(6) (2008) 1478-86.
Koros, William J. and Rajiv Mahajan, *Pushing the limits on possibilities for large scale gas separation: Which strategies?*, J. Membr. Sci. 175 (2000) 181-96.
Kuhn, Jelan, et al., *Detemplation of DDR type zeolites by ozonication*, Micropor. Mesopor. Mater. 120 (2009) 12-18.
Kumar, P. et al., *Ordered mesoporous membranes: Effects of support and surfactant removal conditions on membrane quality*, J. Membr. Sci. 279 (2006) 539-47.
Kusakabe, Katsuki, et al., *Formation of a Y-type zeolite membrane on a porous alpha-alumina tube for gas separation*, Ind. Eng. Chem. Res. 36(3) (1997) 649-55.
Lee, Clare, et al., *Thermodynamic and kinetic factors in the hydrothermal synthesis of hybrid frameworks: Zinc 4-cyclohexene-1,2-dicarboylates*, Chem. Comm. (2006) 2687-89.
Li, Shiguang, et al., *Scale-up of SAPO-34 membranes for $CO_2/CH_4$ separation*, J. Membr. Sci. 352 (2010) 7-13.
Li, Yan-Shuo, et al., *Molecular sieve membrane: Supported metal-organic framework with high hydrogen selectivity*, Angew. Chem. Int. Edit. 49 (2010) 548-51.
Li, Zong-Qun, et al., *Fabrication of nanosheets of a fluorescent metal-organic framework $[Zn(BDC)(H_2O)]_n$ (BDC=1,4-benzenedicarboxylate): Ultrasonic synthesis and sensing of ethylamine*, Inorganic Chemistry Communications 11(11) (2008) 1375-77.

Li, Zong-Qun, et al., *Ultrasonic synthesis of the microporous metal-organic framework $Cu_3(BTC)_2$ at ambient temperature and pressure: An efficient and environmentally friendly method*, Mater. Lett. 63 (2009) 78-80.
Lin, Zhoujia, et al., *Chiral induction in the ionothermal synthesis of a 3-D coordination polymer*, J. Am. Chem. Soc. 129(16) (2007) 4880-81.
Lindmark, Jonas and Jonas Hedlund, *Modification of MFI membranes with amine groups for enhanced $CO_2$ selectivity*, J. Mater. Chem. 20(11) (2010) 2219-25.
Liu, Xin-Lei, et al., *An organophilic pervaporation membrane derived from metal-organic framework nanoparticles for efficient recovery of bio-alcohols*, Angew. Chem. Int. Ed. 50(45) (2011) 10636-39.
Liu, Yunyang, et al., *Synthesis and characterization of ZIF-69 membranes and separation for $CO_2/CO$ mixture*, J. Membr. 353 (2010) 36-40.
Liu, Yunyang, et al., *Synthesis of highly c-oriented ZIF-69 membranes by secondary growth and their gas permeation properties*, J. Membr. Sci. 379 (2011) 46-51.
Ma, Bao-Qing, et al., *Microporous pillared paddle-wheel frameworks based on mixed-ligand coordination of zinc Ions*, Inorg. Chem. 44(14) (2005) 4912-14.
Matsuda, H., et al., *Improvement of ethanol selectivity of silicalite membrane in pervaporation by silicone rubber coating*, J. Membr. Sci. 210(2) (2002) 433-37.
McCarthy, Michael C., et al., *Synthesis of zeolitic imidazolate framework films and membranes with controlled microstructures*, Langmuir 26(18) (2010) 14636-41.
Morris, William, et al., *Crystals as molecules: Postsynthesis covalent functionalization of zeolitic imidazolate frameworks*, J. Am. Chem. Soc. 130(38) (2008) 12626-27.
Nair, Sankar, et al., *Separation of close boiling hydrocarbon mixtures by MFI and FAU membranes made by secondary growth*, Micropor. Mesopor. Mater. 48 (2001) 219-28.
Pachfule, Pradip, et al., *Solvothermal synthesis, structure, and properties of metal organic framework isomers derived from a partially fluorinated link*, Cryst. Growth Des. 11 (2011) 1215-22.
Pan, Long, et al., *Microporous metal organic materials: Promising candidates as sorbents for hydrogen storage*, J. Am. Chem. Soc. 126(5) (2004) 1308-09.
Parikh, Atul N., et al., *Non-thermal calcination by ultraviolet irradiation in the synthesis of microporous materials*, Micropor. Mesopor. Mater. 76 (2004) 17-22.
Qiu, Wulin, et al., *Dehydration of ethanol-water mixtures using asymmetric hollow fiber membranes from commercial polyimides*, J. Membr. Sci. 327 (2009) 96-103.
Ranjan, Rajiv and Michael Tsapatsis, *Microporous metal organic framework membrane on porous support using the seeded growth method*, Chem. Mater. xxx(xx) (2009) 000-000.
Sommer, Stefan and Thomas Melin, *Influence of operation parameters on the separation of mixtures by pervaporation and vapor permeation with inorganic membranes. Part 1: Dehydration of solvents*, Chem. Eng. Sci. 60 (2005) 4509-23.
Son, Won-Jin, et al., *Sonochemical synthseis of MOF-5*, Chem. Commun. 47 (2008) 6336-38.
Van Den Bergh, J., et al., *Separation and permeation characteristics of a DD3R zeolite membrane*, J. Membr. Sci. 316 (2008) 35-45.
Van Den Bergh, Johan, et al., *Modeling permeation of $CO_2/CH_4$, $N_2/CH_4$, and $CO_2$/air mixtures across a DD3R zeolite membrane*, J. Phys. Chem. C 114(20) (2010) 9379-89.
Venna, Surendar R. and Moises A. Carreon, *Highly permeable zeolite imidazolate framework-8 membranes for CO2/CH4 separation*, J. Am. Chem. Soc.132(1) (2010) 76-78.
Watanabe, Taku, et al., *Computational identification of a metal organic framework for high selectivity membrane-based $CO_2/CH_4$ separations: $Cu(hfipbb)(H_2hfipbb)_{0.5}$*, Phys. Chem. Chem. Phys. 11 (2009) 11389-94.
Xomeritakis, George, et al., *Transport properties of alumina-supported MFI membranes made by secondary (seeded) growth*, Micropor. Mesopor. Mater. 38 (2000) 61-73.

(56) References Cited

OTHER PUBLICATIONS

Weh, K., et al., *Permeation of single gases and gas mixtures through faujasite-type molecular sieve membrances*, Micropor. Mesopor. Mater. 54 (2002) 27-36.
Xu, Gengsheng, et al., *Preparation of ZIF-8 membranes supported on ceramic hollow fibers from a concentrated synthesis gel*, J. Membr. Sci. 385-386 (2011) 187-93.
Yao, Jianfeng, et al., *Contra-diffusion synthesis of ZIF-8 films on a polymer substrate*, Chem. Commun. 47 (2011) 2559-61.
Yan, Yushan, et al., *Preparation of highly selective zeolite ZSM-5 membranes by a post-synthetic coking treatment*, J. Membr. Sci. 123(1) (1997) 95-103.
Yang, Lisha and Huimin Lu, *Microwave-assisted ionothermal synthesis and characterization of zeolitic imidazolate framework-8*, Chinese J. Chem. 30 (2012) 1040-44.
Yoo, Won Cheol, et al., *High-performance randomly oriented zeolite membranes using brittle seeds and rapid thermal processing*, Angew. Chem. Int. Ed. 49 (2010) 8699-703.
Zhang, Yanfeng, et al., *Blocking defects in SAPO-34 membranes with cyclodextrin*, J. Membr. Sci. 358 (2010) 7-12.
Zheng, Zhenkun, et al., *Synthesis, characterization and modification of DDR membranes grown on alpha-alumina supports*, J. Mater. Sci. 43 (2008) 2499-502.
PCT Jul. 27, 2012 International Search Report and Written Opinion issued in International Patent Application PCT/US2012/025064.
PCT May 25, 2012 International Search Report and Written Opinion issued in International Patent Application PCT/US2012/025080.
PCT Nov. 6, 2012 International Search Report and Written Opinion issued in International Patent Application PCT/US2012/054817.
PCT Feb. 23, 2012 International Search Report and Written Opinion issued in International Patent Application PCT/US2011/047769.
PCT Oct. 18, 2013 International Search Report and Written Opinion issued in International Patent Application PCT/US2013/042075.
Mar. 5, 2013 Office Action mailed for U.S. Appl. No. 13/611,988, filed Sep. 12, 2012.
Jun. 5, 2013 Response to Office Action dated Mar. 5, 2013 for U.S. Appl. No. 13/611,988, filed Sep. 12, 2012.
Jun. 10, 2013 Office Action/Noncompliant Amendment mailed for U.S. Appl. No. 13/611,988, filed Sep. 12, 2012.
Jun. 14, 2013 Response to Office Action/Noncompliant Amendment dated Jun. 10, 2013 for U.S. Appl. No. 13/611,988, filed Sep. 12, 2012.
Sep. 5, 2013 Office Action mailed for U.S. Appl. No. 13/611,988, filed Sep. 12, 2012.
Nov. 5, 2013 Response to Final Office Action dated Sep. 5, 2013 for U.S. Appl. No. 13/611,988, filed Sep. 12, 2012.
Nov. 18, 2013 Notice of Allowability mailed for U.S. Appl. No. 13/611,988, filed Apr. 4, 2011.
Nov. 20, 2013 Notice of Allowability mailed for U.S. Appl. No. 13/399,645, filed Feb. 17, 2012.
Marler, et al., *Studies on clathrasils VIII. Nonasils-[$4^1 5^8$], $88SiO_2 *8M^8 *8M^9 *4M^{20}$ : Synthesis, thermal properties, and crystal structure*, J. Inclusion Phenomena 4(4) (1986) 339-349.
Aksay, et al., *Biometric pathways for assembling inorganic thin films*, Science 273(5277) (1996) 892-898.
Miyata, et al., *Silica films with a single-crystalline mesoporous structure*, Nat. Mater. 3(9) (2004) 651-656.
Yang, et al., *Registered growth of mesoporous silica films on graphite*, J. Mater. Chem. 7(7) (1997) 1285-1290.
JP Jun. 17, 2014 Examiner's Decision of Refusal mailed in Japanese Patent Application 2012-543346 (with English Translation).
CN Mar. 9, 2015 Response to Office Action (with English translation of claims) filed in China Patent Application No. 201180052181.7.
JP Apr. 7, 2015 Office Action mailed in Japan Patent Application No. 2013-536619 (with English translation).
JP Apr. 24, 2015 English translation of Description and Claims for JP Patent Application Laid-Open No. 2002-338229.
JP Apr. 24, 2015 English translation of Description and Claims for JP Patent Application Laid-Open No. 2008-173576.
CN Dec. 2, 2014 Response to Office Action filed in China Patent Application No. 201080057358.8 (with English translation).
CN Mar. 16, 2015 Third Office Action mailed in China Patent Application No. 201080057358.8 (with English translation).
Sep. 1, 2015 Office Action mailed in U.S. App. No. 13/897,939, filed May 20, 2013.
Dec. 1, 2015 Amendment and Response to Office Action dated Sep. 1, 2015 in U.S. Appl. No. 13/897,939, filed May 20, 2013.
JP Dec. 15, 2015 Office Action mailed in Japan Patent Application No. 2013-536619 (with English translation).
Brown, et al., *Interfacial microfluidic processing of metal-organic framework hollow fiber membranes*, Science 345(6192) (2014) 72-75.
Calvo, et al., *Pore size distributions in macroporous membranes*, J. Colloid & Interface Sci. 176(2) (1995) 467-78.
Khare, et al., *A quantitative method for measuring nanocomposite dispersion*, Polymer 51 (2010) 719-29.
Korelskiy, et al., *Characterization of flow-through micropores in MFI membranes by permporometry*, J. Membr. Sci. 417-418 (2012) 183-92, Accepted manuscript (2015).
Zhang, et al., *Unexpected molecular sieving properties of Zeolitic Imidazolate Framework-8*, J. Phys. Chem. Lett. 3(16) (2012) 2130-34.
Feb. 2, 2016 Final Office Action mailed in U.S. Appl. No. 13/897,939, filed May 20, 2013.
Mar. 15, 2016 Amendment and Response to Final Office Action dated Feb. 2, 2016; and First Request for Continued Examination filed in U.S. Appl. No. 13/897,939, filed May 20, 2013.
Mar. 22, 2016 Notice of Allowance / Notice of Allowability mailed in U.S. Appl. No. 13/897,939, filed May 20, 2013.

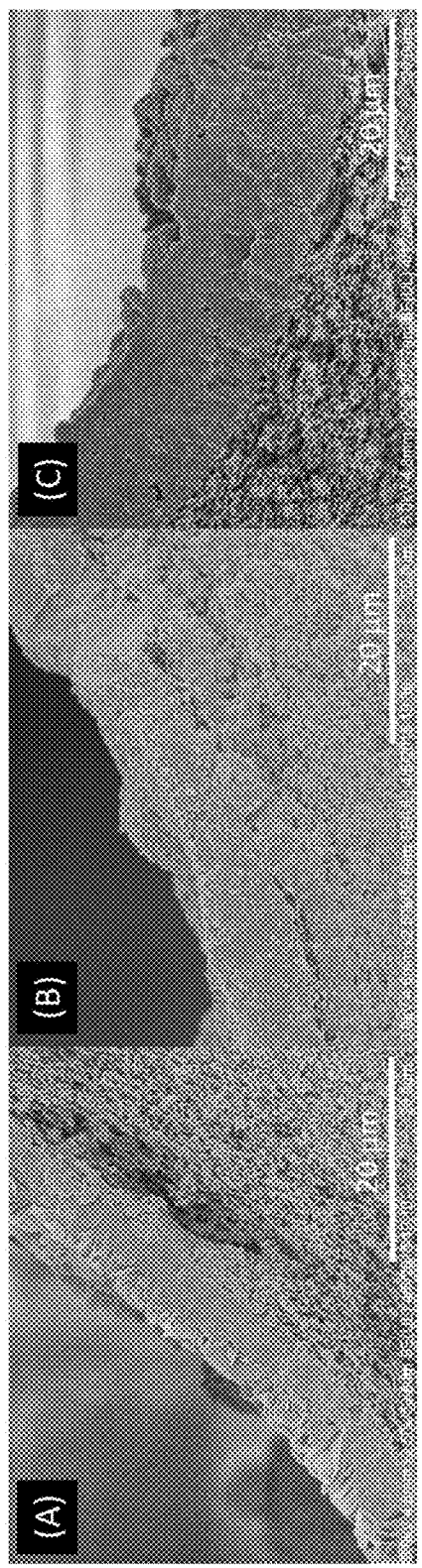

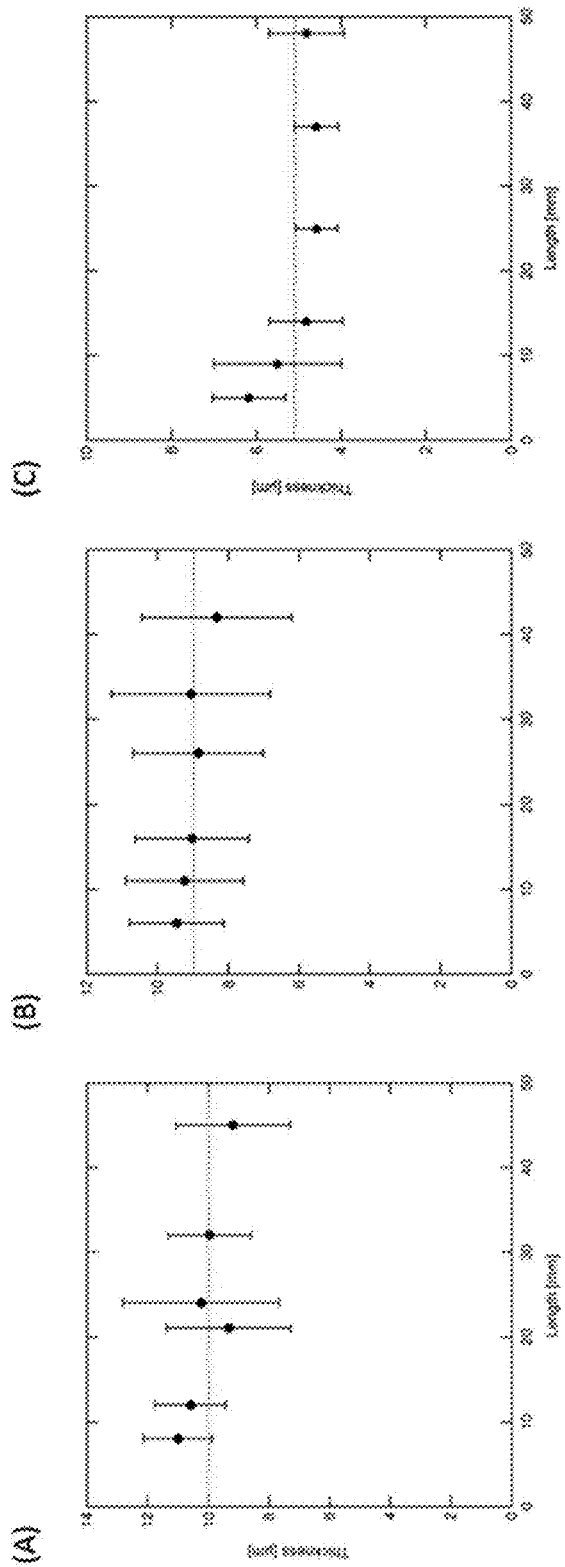

HIGH EFFICIENCY, HIGH PERFORMANCE METAL-ORGANIC FRAMEWORK (MOF) MEMBRANES IN HOLLOW FIBERS AND TUBULAR MODULES

PRIOR RELATED APPLICATIONS

The present application is a continuation-in-part of U.S. patent application Ser. No. 14/231,871, which claims priority to U.S. Provisional Patent Application Ser. No. 61/913, 592, filed on Dec. 9, 2013 for "Flow Processing and Characterization of Metal-Organic Framework (MOF) Membranes in Hollow Fiber and Tubular Modules" and to U.S. Provisional Patent Application Ser. No. 61/820,489, filed on May 7, 2013 for "Flow Processing and Characterization of Metal-Organic Framework (MOF) Membranes in Tubular and Hollow Fiber Modules."

FEDERALLY SPONSORED RESEARCH STATEMENT

Not Applicable ("N/A")

REFERENCE TO MICROFICHE APPENDIX

N/A

FIELD OF INVENTION

This invention relates to a scalable, in situ flow-processing method to synthesize metal-organic framework (MOF) membranes on or inside hollow fiber and tubular modules and to characterize their molecular transport properties, and, in particular, to a high-efficiency, high-performance zeolitic imidazolate framework (ZIF)-8 mixed material that is free of defects.

BACKGROUND OF THE INVENTION

Molecular sieving membranes have generated great interest as high-performance separation systems for production of clean and renewable fuels, building block chemicals, and specialty chemicals. Compared to thermodynamically-driven separation methods, membrane-based processes can significantly reduce the energy and capital costs of separating molecules on a large scale. For example, energy-intensive methods such as cryogenic distillation are commonly used to separate hydrocarbons because of their quite similar thermodynamic properties. Membranes composed of molecular sieving materials such as zeolites,[1] layered zeolites,[2] or metal-organic frameworks[3] (MOFs) have intrinsic advantages over polymeric membranes such as a simultaneously high permeability and selectivity. Despite their performance limitations, polymeric membranes have continued to dominate industrial membrane separations due to their relative ease of processing into morphologies such as hollow fibers.[4] The greatest scientific challenge facing molecular sieving membranes is the lack of an easily scalable, reliable, and benign fabrication process.[5] This limitation has been particularly severe for zeolite membranes, which are typically fabricated by hydrothermal synthesis on high-cost support materials.

While substantive progress is being made in gradually reducing the barriers to economical zeolitic membranes,[6-7] the advent of metal-organic framework (MOF) molecular sieves has created potential for more scalable membrane fabrication processes under relatively benign conditions.[8]

MOFs consist of metal centers connected by coordination bonds to organic linker molecules, and have been used to grow crystalline membranes through techniques similar to those developed for zeolitic membranes. The zeolitic imidazolite framework (ZIF) subclass of MOFs is of particular interest for membrane fabrication, because of its tunable pore size and chemistry,[9] and relatively good thermal and chemical stability.[10-11] In an early demonstration of scalable ZIF membrane processing, we recently demonstrated the growth of ZIF-90 membranes on the outer surfaces of porous polymeric poly(amide-imide) (e.g., TORLON®) hollow fibers (about 250 μm outer diameter) by a seeded growth process[12] at mild conditions (65° C. in methanol solutions). Molecular sieving membranes on the inner surfaces of the hollow fibers are much more challenging to grow but better suited for scalable fabrication and industrial uses, due to the ability to be bundled in close proximity while avoiding membrane-membrane contact points and interfaces that lead to defects during synthesis.

It has been shown that free-standing MOF films and spheroids can be synthesized at the interfaces between two immiscible solvents.[13] However, the growth of defect-controlled membranes on the inner surfaces of microscale hollow fibers (50-300 μm inner (bore) diameter) is a key, and more challenging, advance. As the bore size (and hence volume) is decreased to microscopic dimensions, the likelihood of reactant depletion and local inhomogeneity increase, leading to loss of control over membrane continuity and defect density.[14]

Thus, an Interfacial Microfluidic Membrane Processing (IMMP) approach for preparing defect-controlled and defect-free molecular sieving membranes on the inner surfaces of microscale hollow fibers is needed to improve performance in gas and liquid separations.

SUMMARY OF THE INVENTION

Zeolite and MOF membranes are typically synthesized in a reactor, and then removed for washing and mounting in a separate module. However, in this invention, the inventors demonstrate an in situ flow process to synthesize a membrane on or inside hollow fiber and tubular modules at a controlled location, and to subsequently activate the membrane and measure separation properties in situ without having to remove the membrane. Furthermore, damage to membranes during module construction and handling are eliminated. Lastly, this reactor cell design is capable of providing continuous flow in the bore and shell side of the hollow fiber or tubular module to allow for reagent recycling and to homogenize membrane thickness along the length. By using a single module for synthesis and characterization, membrane growth variables and post-treatments can be controlled accurately. This device also allows in situ characterization of the permeation properties of the module after each treatment step to determine cause and effect.

In other words, this reactor cell design facilitates a scalable and generalizable method of processing molecular sieving membranes (specifically, ZIF-8 membranes) referred to as an Interfacial Microfluidic Membrane Processing (IMMP) approach. The IMMP approach combines three key concepts: first, a two-solvent interfacial approach that can be tuned to achieve positional control over membrane formation (at inner and outer surfaces, as well as inside the bulk, of the porous fiber); second, supply, replenishment, and recycling of reactants at microfluidic conditions in the hollow fiber bore; and third, membrane synthesis in situ directly in the membrane module, which also functions as a membrane synthesis reactor.

In the present invention, the inventors demonstrate an isothermal and initial heating IMMP approach that leads to a mechanism of ZIF-8 membrane growth in hollow fibers that elucidates the roles of reactant transport, film crystallization, and the hollow fiber support microstructure. The inventors also demonstrate how a mechanistic understanding of ZIF-8 hollow fiber membrane formation can be used to engineer a higher-throughput, higher-selectivity ZIF-8 membrane that is free of defects for propane/propylene separations. Further, the inventors present detailed binary and ternary mixed gas permeation measurements to highlight the excellent separation characteristics of these defect-controlled and defect-free ZIF-8 hollow fiber membranes.

In an embodiment, a reactor cell for flow processing molecular sieving membranes comprises a hollow fiber having a first end and a second end, wherein a length of the first end is supported by and sealed into the first hole and a length of the second end is supported by and sealed into the second hole; wherein the first and second ends of the hollow fiber are capped with a capping solution, wherein a molecular sieving membrane that is uniform and at least 95% free of defects is grown on an inner bore surface of the hollow fiber. In an embodiment, the molecular sieving membrane is at least about 97% free of defects and wherein any defects are less than about 20 nm in diameter, length or width. In an embodiment, the molecular sieving membrane is at least about 97% free of defects and wherein any defects are less than about 10 nm in diameter, length or width.

In an embodiment, the lengths of the first and second ends of the hollow fiber are sealed into the first and second holes with an adhesive.

In an embodiment, the capping solution is about 8 wt % to about 10 wt % poly(dimethylsiloxane) (PDMS) in heptane.

In an embodiment, a method of making a reactor cell comprises the steps of: fabricating a reactor chamber extending into the reactor module from the upper surface of the reactor module; fabricating an O-ring groove with an inner dimension slightly larger than and offset from the outer dimension of the reactor chamber; fabricating the first hole extending into the reactor chamber from the first surface and the second hole opposing the first hole and extending into the reactor chamber from the second surface; fabricating a third hole extending into the reactor chamber from a third surface and a fourth hole opposing the third hole and extending into the reactor chamber from a fourth surface; supporting and sealing the length of the first end of the hollow fiber in the first hole and the length of the second end of the hollow fiber into the second hole; capping the first and second ends of the hollow fiber with a capping solution; fabricating the reactor module cover to fit on the upper surface of the reactor module and fastening the reactor module cover to the seal the reactor chamber; fluidly connecting a bore solution to the first inlet; fluidly connecting a shell solution to the second inlet; and growing a molecular sieving membrane that is uniform and at least about 95% free of defects on an inner bore surface of the hollow fiber.

In an embodiment, the bore solution contains a limited $Zn^{+2}$ concentration ranging from about 0.005 to about 0.1 mol/L $Zn^{+2}$ in 1-octanol. In an embodiment, the bore solution contains a limited $Zn^{+2}$ concentration ranging from about 0.01 to about 0.03 mol/L $Zn^{+2}$ in 1-octanol. In an embodiment, the bore solution is about 0.018 mol/L $Zn^{+2}$ in 1-octanol. In an embodiment, the shell solution contains an excess mIm ligand concentration ranging from about 0.5 to about 10 mol/L 2-methyl imidazole (mIm) in deionized water.

In an embodiment, the shell solution contains an excess mIm ligand concentration ranging from about 1.2 to about 1.6 mol/L 2-methyl imidazole (mIm) in deionized water. In an embodiment, the shell solution is about 1.37 mol/L mIm in deionized water. In an embodiment, the method further comprises the step of gently stirring the shell solution to prevent formation of local concentration gradients. In an embodiment, the shell solution is stirred at about 40 rpm to about 80 rpm.

In an embodiment, the method of making the reactor cell further comprises the steps of flowing the bore solution at a first flow rate for a first period, wherein a first temperature is increased to a second temperature during a portion of the first period; stopping the first flow rate of the bore solution for a second period; flowing the bore solution at a second flow rate for a third period; and stopping the second flow rate of the bore solution for a fourth period. In an embodiment, the second temperature is decreased to a third temperature during a portion of the first period.

In an embodiment, the first and second flow rates are about 1 μL/hour to about 1000 μL/hour per individual hollow fiber. In an embodiment, the first and second flow rates are about 10 μL/hour to about 100 μL/hour per individual hollow fiber.

In an embodiment, the first period is about 1 hour to about 3 hours, the second period is about 3 hours to about 4 hours, the third period is about 10 minutes to about 30 minutes, and the fourth period is about 3 hours to about 4 hours.

In an embodiment, the method of making the reactor cell further comprises the step of rinsing the membrane in solvents selected from the group consisting of 1-octanol, heptanes, hexane, methanol and deionized water.

In an embodiment, a method of using the reactor cell comprises the steps of: fluidically connecting a feed mixture to the first inlet; fluidically connecting a sweep gas to the second inlet; collecting a separated mixture from the first outlet; and collecting permeate from the second outlet.

In an embodiment, the feed mixture to the reactor cell is selected from the group consisting of hydrogen/hydrocarbons, hydrogen/propane, propylene/propane and butenes/butanes. In an embodiment, the feed mixture to the reactor cell is selected from the group consisting of hydrogen/propane, propylene/propane and butenes/butanes. In an embodiment, the feed mixture to the reactor cell comprises about 2 mol % to about 95 mol % i-butane, about 2 mol % to about 95 mol % n-butane and mixtures thereof.

In an embodiment, an operating temperature for the reactor cell is from about 30° C. to about 95° C. or any value there between.

In an embodiment, an operating pressure for the reactor is from about 1 bar to about 14 bar or any value there between.

These and other objects, features and advantages will become apparent as reference is made to the following detailed description, preferred embodiments, and examples, given for the purpose of disclosure, and taken in conjunction with the accompanying drawings and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature and objects of the present invention, reference should be made to the following detailed disclosure, taken in conjunction with the accompanying drawings, in which like parts are given like reference numerals, and wherein:

FIG. 27A illustrates an exemplary cross-sectional SEM image of a ZIF-8 membrane grown on a polyamide-imide (e.g., TORLON®) hollow fiber after 2 hours of continuous membrane growth (Step 1) using isothermal IMMP approach;

FIG. 27B illustrates an exemplary cross-sectional SEM image of a ZIF-8 membrane grown on a polyamide-imide (e.g., TORLON®) hollow fiber after 2 hours of continuous membrane growth (Step 1) and 3.5 hours of static membrane growth (Step 2) using isothermal IMMP approach;

FIG. 27C illustrates an exemplary cross-sectional SEM image of a ZIF-8 membrane grown on a polyamide-imide (e.g., TORLON®) hollow fiber after 2 hours of continuous membrane growth (Step 1), 3.5 hr of static membrane growth (Step 2) and 20 minutes of second continuous membrane growth followed by 3.5 hours of second static membrane growth (Step 3) using isothermal IMMP approach;

FIG. 32A illustrates a chart of Length (mm) vs Thickness (μm) for a ZIF-8 membrane grown on a polyamide-imide (e.g., TORLON®) hollow fiber using isothermal IMMP approach with the red dotted lines indicating the average thickness of about 10.0 μm for the ZIF-8 membrane;

FIG. 32B illustrates a chart of Length (mm) v.s Thickness (μm) for a ZIF-8 membrane grown on a modified polyamide-imide (e.g., TORLON®) hollow fiber with the red dotted lines indicating the average thickness of about 9.1 μm for the ZIF-8 membrane;

FIG. 32C illustrates a chart of Length (mm) v.s Thickness (μm) for a ZIF-8 membrane grown on a modified polyamide-imide (e.g., TORLON®) hollow fiber using initial heating IMMP approach with the red dotted lines indicating the average thickness of about 5 μm for the ZIF-8 membrane;

DETAILED DESCRIPTION OF EMBODIMENTS OF THE INVENTION

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

In this invention, the inventors demonstrate an in situ flow process to synthesize a membrane on or inside a hollow fiber or tubular membrane module at a controlled location, and to subsequently activate the membrane and measure separation properties in situ without having to remove the membrane. By using a single module for synthesis and characterization, membrane growth variables and post-treatments can be controlled accurately. This device also allows in situ characterization of the permeation properties of the module after each treatment step to determine cause and effect.

Hollow Fiber or Tubular Membrane Module Detail

In an embodiment of the present invention, a membrane was synthesized on or inside a hollow fiber or tubular membrane module. A side perspective view of a hollow fiber or tubular membrane module 100 is depicted in FIG. 1A. As shown in FIG. 1A, the hollow fiber or tubular membrane module 100 comprises a shell 105 and a bore 110.

Figure 1B:
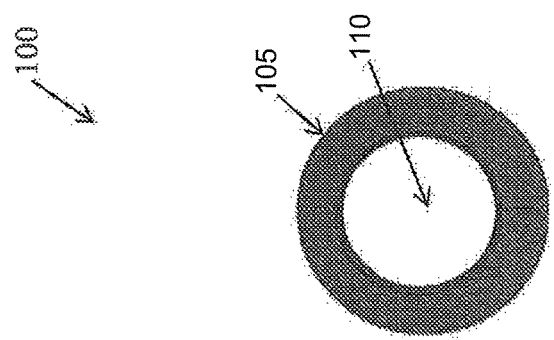
FIG. 1B illustrates a cross-sectional view of a hollow fiber or tubular membrane module showing location of a bore and a shell.
Figure 1A:
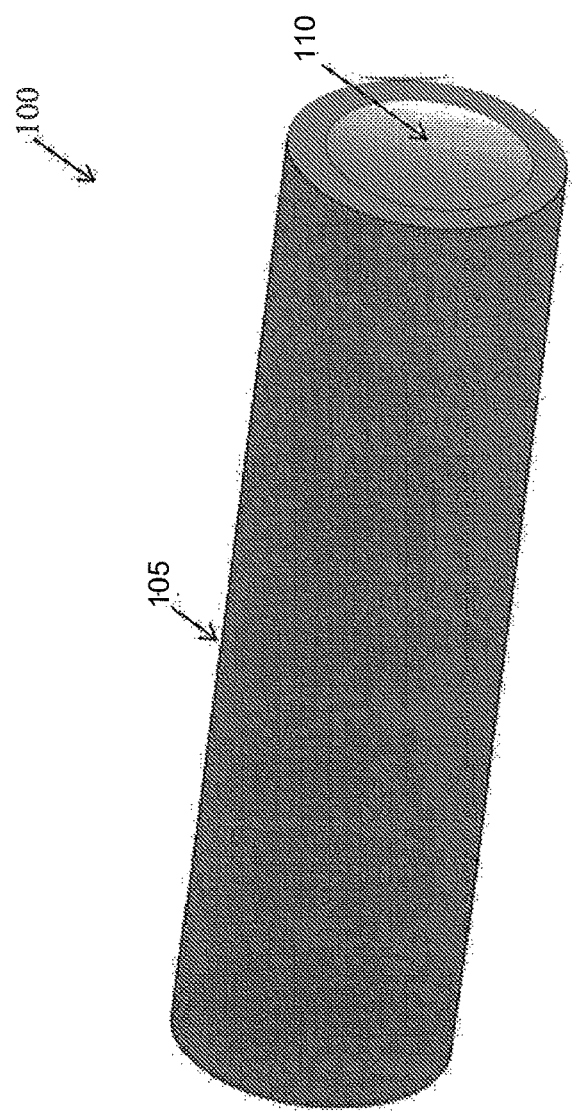
FIG. 1A illustrates a side perspective view of a hollow fiber or tubular membrane module showing location of a bore and a shell.

A cross-sectional view of a hollow fiber or tubular membrane module 100 is depicted in FIG. 1B. As shown in FIG. 1B, the hollow fiber or tubular membrane module 100 comprises a shell 105 and a bore 110. In an embodiment, the hollow fiber or tubular module may have an inner (bore) diameter of about 50 μm to about 5000 μm. In an embodiment, the hollow fiber or tubular module may have an inner (bore) diameter of about 50 μm to about 300 μm.

Design Considerations/Machining Detail for Reactor Cell

A reactor cell of the present invention may be cubic-, rectangular-, cylindrical- or cylindrical-like shaped (e.g., elliptical base), and the like. In an embodiment, a reactor module 200 was fabricated to have a base shape and a first height, and a reactor module cover 420 was fabricated to have the same base shape as the reactor module 200 and a second height. In an embodiment, the base shape may be selected from the group consisting of square, rectangular, circular and ellipse.

Suitable materials for the reactor module and/or cover include any metal, or any plastic compatible with an adhesive (e.g., epoxy), alcohol solvents and water. In an embodiment, the metal may be selected from the group consisting of stainless steel, stainless steel alloys such as MONEL® (Special Metals Corp.) and HASTALLOY® (Haynes International, Inc.), and the like. In an embodiment, the plastic may be selected from the group consisting of polyether ketone (PEEK), polymethylene (e.g., DELRIN® (DuPont Co.)), polytetrafluorethylene (PTFE) (e.g., TEFLON® (Du- Pont Co.)), and the like. In an embodiment, stainless steel 304 was used to fabricate the reactor module 200 and cover 420.

Figure 2:
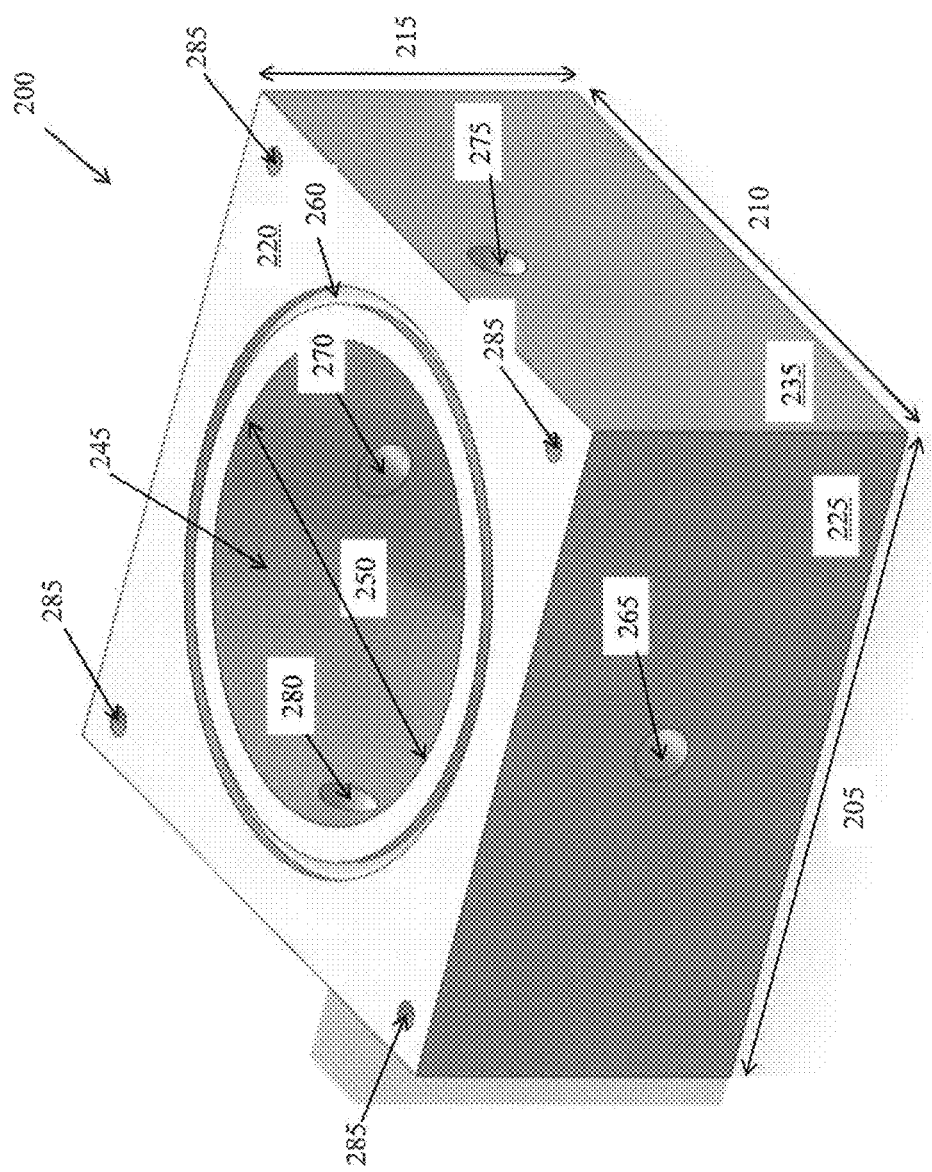
FIG. 2 illustrates an upper, right front perspective view of a reactor according to an embodiment of the present invention.
Figure 3:
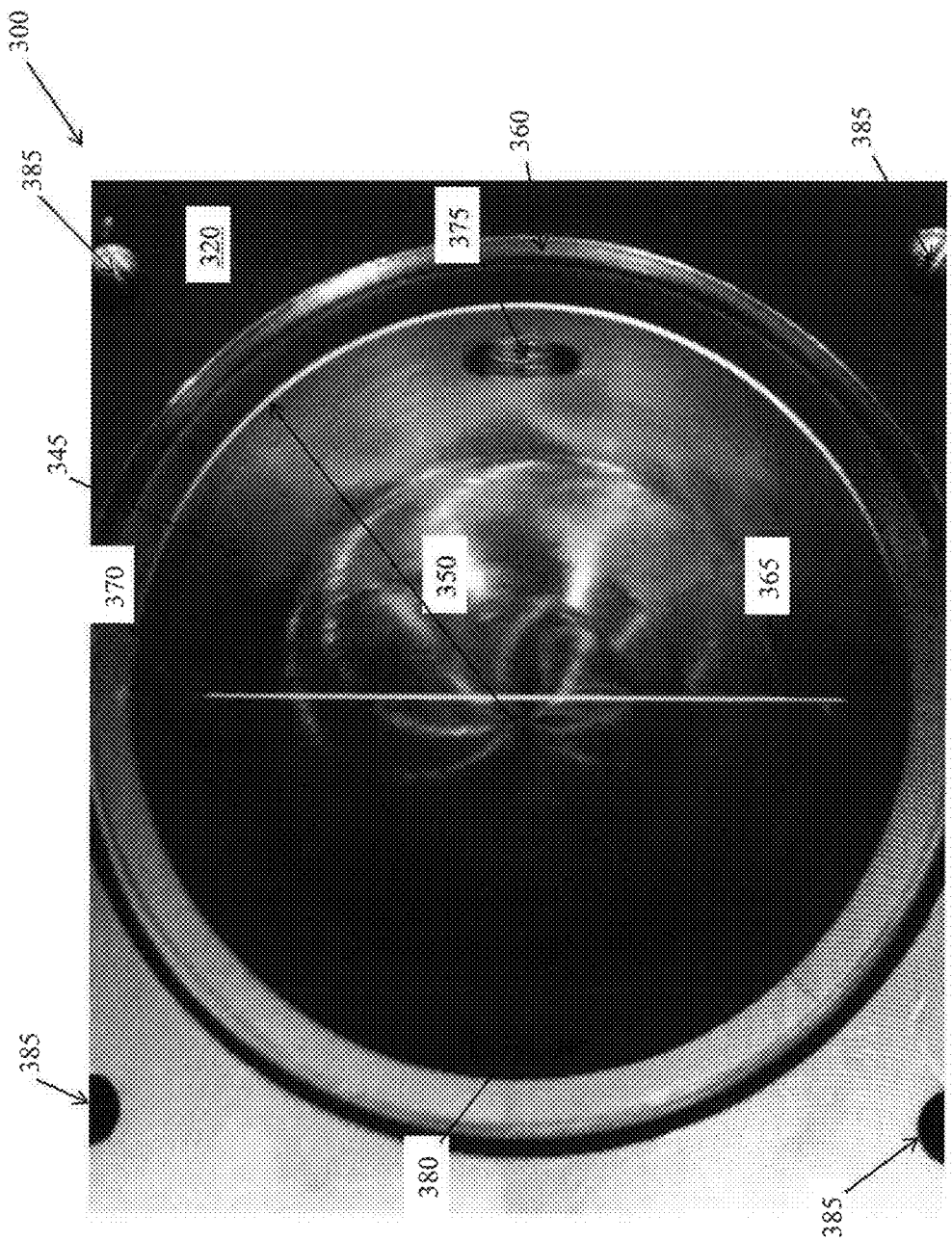
FIG. 3 illustrates a photograph of a polyamide-imide (e.g., TORLON®) hollow fiber epoxy-sealed inside a reactor according to an embodiment of the present invention.
Figure 4:
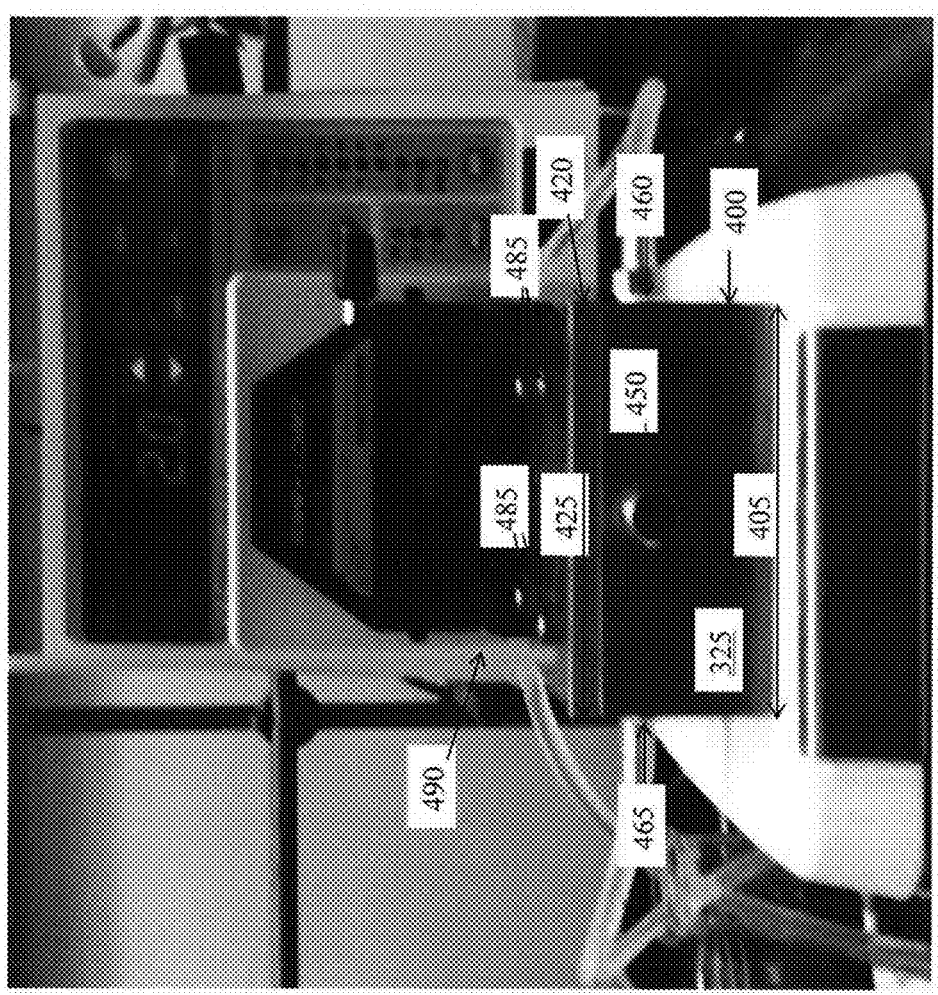
FIG. 4 illustrates a photograph of a reactor connected to cycling peristaltic pump according to an embodiment of the present invention.

Although a rectangular reactor module 200 and cover 420 are depicted in FIGS. 2-4, a person of ordinary skill in the art could easily adapt these teachings to cubic, cylindrical and cylindrical-like reactor modules and covers. Accordingly, although the rectangular reactor module 200 and cover 420 are discussed in detail below, this discussion should not be interpreted to exclude cubic, cylindrical and cylindrical-like reactor modules and covers.

Although the reactor module and cover were machined from metal blocks, a person of ordinary skill in the art (POSITA) could easily adapt these teaching to other suitable methods of fabricating parts. In an embodiment, the fabrication method may be selected from machining, molding, printing and combinations thereof. For example, if a plastic material is used, the reactor module and cover may be molded by compression or injection molding or printed on a 3-D printer as customary in the art. Accordingly, although machining is discussed in detail below, this discussion should not be interpreted to exclude molding and printing techniques.

An upper, right front perspective view of a reactor module 200 is depicted in FIG. 2. As shown in FIG. 2, the reactor module 200 has a first length 205, a second length 210 and a third length 215. Further, the reactor module 200 has an upper surface 220, a first side surface 225, a second side surface 230 (not shown), a third side surface 235 and a fourth side surface 240 (not shown). The reactor module 200 may be constructed from a metal or a plastic as discussed above. In an embodiment, the reactor module 200 was constructed from stainless steel 304.

The reactor module 200 has a reactor chamber 245 with a reactor chamber diameter 250 and reactor chamber depth 255 (not shown) extending into the reactor module 200 from the upper surface 220. Further, the reactor module 200 has an O-ring groove 260 extending into the reactor module 200 from the upper surface 220 and surrounding the reactor chamber 245.

In an embodiment, the reactor chamber may be cylindrical. In such cylindrical embodiment, the inner diameter of the O-ring groove 260 is slightly larger than and offset from the reactor chamber diameter 250.

In an embodiment, the reactor chamber may not be cylindrical. For such non-cylindrical embodiments, an O-ring groove with an inner dimension slightly larger than and offset from an outer dimension of the reactor chamber may be machined in the upper surface of the reactor module.

In an embodiment, the reactor module 200 has a temperature probe chamber 290 (not shown) with a temperature probe diameter 295 (not shown) and a temperature probe depth (not shown) extending into the reactor module 200 from the upper 220 or first side 225, second side 230, third side 240, fourth side 245 surface. Suitable temperature probes 490 include resistance temperature detectors (RTDs), thermocouples, thermometers, and the like.

The reactor module 200 has a plurality of holes 285 extending into the reactor module 300 material from the upper surface 225 to attach a reactor module cover (not shown). In an embodiment, if the temperature probe chamber 290 extends into the reactor module 200 from the upper surface 220, the reactor module cover 420 will have a temperature probe hole with a temperature probe diameter 295 extending through the reactor module cover 420 and aligning with the temperature probe diameter 295 of the temperature probe chamber 290 in the reactor module 200. The reactor module cover 420 may be constructed from a metal or a plastic as discussed above. In an embodiment, the reactor module 200 was constructed from stainless steel 304.

The reactor module 200 has a first hole 265 extending into the reaction chamber 245 from a first side surface 225, a second hole 270 extending into the reaction chamber 245 from a second side surface 230 (not shown), a third hole 275 extending into the reaction chamber 245 from a third side surface 235, and a fourth hole 280 extending into the reaction chamber 245 from a fourth side surface 240 (not shown).

In an embodiment, the first 265 and second 270 holes may extend only partially into the first 225 and second 230 side surfaces, respectively, of the reactor chamber 245 such that a first and second smaller hole may extend into the reaction chamber 245 to accept a hollow fiber or tubular membrane module 100 as shown in FIG. 3. In an embodiment, the hollow fiber or tubular membrane module 100 may be held (and sealed) in place in the first and second smaller holes with an adhesive such as an epoxy. In an embodiment, the first 265, second 270, third 275 and fourth 280 holes are threaded to accept various fittings as are customarily used in the art.

In an embodiment, the third 275 and fourth 280 holes extending into the third 235 and fourth 240 side surfaces of the reactor module 200 (i.e., surfaces perpendicular to the mounted hollow fiber or tubular membrane module 100) may be slightly offset either vertically or horizontally from each other to facilitate mixing during flow conditions.

For example, a laboratory-scale reactor module 300 was constructed from a rectangular stainless steel block with a first length 305 of about 3-inches, a second length 310 of about 3-inches and a third length 315 of about 1.5-inches as depicted in FIGS. 3-4. A reactor chamber 345 with reactor chamber diameter 350 of about 2-inches and a depth of about 1.38-inches was machined into the center of the stainless steel block.

Next, first 365, second 370, third 375 and fourth 380 holes were drilled for ⅛-inch NPT fittings through the first 325 (not shown), second 330 (not shown), third 335 (not shown) and fourth 340 (not shown) side surfaces of the stainless steel block. Although ⅛-inch NPT fittings were used, a POSITA could easily adapt this teaching to other fittings. Accordingly, although the ⅛-inch NPT fittings are disclosed, this disclosure should not be interpreted to exclude other fittings.

The first 365 and second 370 holes extended only partially into the first 325 and second 330 side surfaces, respectively, of the reactor chamber 345 such that a first and second smaller holes with a diameter of about 0.5 mm extended into the reaction chamber 345 to accept a hollow fiber or tubular membrane module 100 as shown in FIG. 3. In an embodiment, the first 365 and second 370 holes extended into the first 325 and second 330 side surfaces, respectively, at a height of about 1-inch such that about 0.1-inch wall remained and second smaller holes with a diameter of about 0.02-inch were drilled through the 0.1-inch wall to create an aperture for mounting the hollow fiber or tubular membrane module 100. These smaller holes may be used to support the hollow fiber or tubular membrane module 100. The hollow fiber or tubular membrane module 100 may be mounted (and sealed) in place in the first and second smaller holes with an adhesive such as an epoxy.

Although the smaller holes were used to support the hollow fiber or tubular membrane, a person of ordinary skill in the art (POSITA) could easily adapt these teachings to use an insert to support the hollow fiber or tubular membranes(s) or to bundle the hollow fiber or tubular membranes such that the smaller holes are unnecessary. Accordingly, although smaller holes are discussed in detail above, this discussion should not be interpreted to exclude other techniques of supporting the hollow fiber or tubular membrane.

The third 375 and fourth 380 holes extending into the third 335 and fourth 340 side surfaces, respectively, of the reactor module 300 (i.e., surfaces perpendicular to the mounted hollow fiber or tubular membrane module 100) were offset vertically from each other by about ⅛ to ¼-inch to facilitate mixing during flow conditions. In an embodiment, the third 375 and fourth 380 holes extended into the third 335 and fourth 340 sides, respectively, at a height of about 1⅛-inch such that the third 375 and fourth 380 holes extended into the reactor chamber 345.

In an embodiment (not shown), the first hole 365 may extend into the reactor chamber 345 from the first side surface 325, the second hole 370 opposing the first hole 365 may extend into the reactor chamber 345 from the second surface 330, the third hole 375 may extend into the reactor chamber 345 from the first surface 325 and the fourth hole 380 opposing the third hole 375 may extend into the reactor chamber 345 from the second surface 330.

In an embodiment (not shown), the first hole 365 may extend into the reactor chamber 345 from the first side surface 325, the second hole 370 opposing the first hole 365 may extend into the reactor chamber 345 from the second surface 330, the third hole 375 may extend into the reactor chamber 345 from an upper surface of a reactor module cover 420 and the fourth hole 380 opposing the third hole 375 extends into the reactor chamber 345 from a bottom surface of the reactor chamber 345.

Although a few possible alternative configurations for an inlet (i.e., third hole 375) and an outlet (i.e., fourth hole 380) for an outer (shell) side solution have been discussed above, a POSITA could easily adapt this teaching to other designs. For example, the inlet and the outlet of the outer (shell) side solution may be positioned to create turbulent flow.

As depicted in FIG. 4, the reactor module 400 must be airtight to be used to measure gas and liquid permeation. To provide an airtight seal, an O-ring groove 360 with a diameter of about 2¼-inches and cross-section of about 0.06-inches (AS568-035) was machined in the upper surface 320 of the reactor module 300 to receive an O-ring (see FIG. 3).

In an embodiment, the reactor chamber may not be cylindrical. For such non-cylindrical embodiments, an O-ring groove with an inner dimension slightly larger than and offset from an outer dimension of the reactor chamber may be machined in the upper surface of the reactor module.

A plurality of threaded holes 385 were machined into each corner of the upper surface 320 of the reactor module 300, 400 about 0.35-inches away from the O-ring groove 360 to receive a plurality of 10-32 hexagonal screws 485 as shown in FIGS. 3-4. Although 10-32 hexagonal screws were used to secure a reactor module cover 420 (see FIG. 4) to the reactor module 300, a POSITA could easily adapt this teaching to other fasteners. Accordingly, although the 10-32 hexagonal screws are discussed in detail, this discussion should not be interpreted to exclude other fasteners.

A temperature probe chamber 290 with temperature probe diameter 295 was machined in the reactor module 300, 400 outside of the O-ring groove 360 to receive a temperature probe 490 as shown in FIGS. 2-4. As shown in FIG. 4, the temperature probe 490 (e.g., heat probe, thermometer) is inserted in the temperature probe chamber 290. Suitable temperature probes 490 include heat probe, resistance temperature detectors (RTDs), thermocouples, thermometers, and the like.

A rectangular block was used to fabricate a reactor module cover 420. A photograph of a reactor module 400 and cover 420 is depicted in FIG. 4. As shown in FIG. 4, the reactor module cover 420 has a first length 425 of about 3-inches, a second length 430 (not shown) of about 3-inches and a third length 435 (not shown) of about ¼-inch. A plurality of holes (not shown) was machined in the reactor module cover 420 extending through the cover 420 and aligning with the diameters of the threaded holes 385 in the reactor module 400. In an embodiment, the reactor module cover 420 was constructed from stainless steel 304.

A temperature probe hole (not shown) was machined in the reactor module cover 420 extending through the cover 420 and aligning with the temperature probe diameter 295 of the temperature probe chamber 290 in the reactor module 400. As illustrated in FIG. 4, the temperature probe 490 (e.g., heat probe, thermometer) is inserted in the temperature probe hole (not shown) of the cover 420 and into the temperature probe chamber 290 (not shown) of the reactor module 400. Suitable temperature probes 490 include heat probes, resistance temperature detectors (RTDs), thermocouples, thermometers, and the like.

The reactor module cover 420 provides a flange-seal by tightening the cover 420 onto the reactor module 400 via the plurality of 10-32 hexagonal screws 485.

Temperature Control of Reactor Cell/Module

The reactor module 400 may be heated and/or cooled to a temperature between about 0° C. and about 200° C. As shown in FIG. 4, the laboratory-scale reactor module 400 was placed on a stir plate, and heated to about 30° C. with a temperature probe 490. In an embodiment, the temperature probe 490 was set at about 30° C. and inserted into the temperature probe chamber 290 of the reactor module 400.

Although a temperature probe 490 was used to heat the reactor module 400, a POSITA could easily adapt this teaching to other heating and/or cooling methods. Accordingly, although the temperature probe heating method is discussed in detail, this discussion should not be interpreted to exclude other heating and/or cooling methods. For example, suitable heaters include temperature probes, hot plates, heating coils, enclosure heaters, silicone rubber heaters, polyester heaters, polyimide heaters, strip heaters, band heaters, tubular heaters, cartridge heaters, and the like. For example, suitable coolers include liquid baths, cooling coils, enclosure coolers, thermoelectric coolers, thermoelectric chillers, heat sinks, fans, and the like.

The temperature of the reactor module 400 may be set with a temperature probe 490 or measured with a thermometer. Although a temperature probe 490 was used, a POSITA could easily adapt this teaching to other combinations of heaters (discussed above) and temperature probes. Suitable temperature probes 490 include resistance temperature detectors (RTDs), thermocouples, thermometers, and the like.

Mounting/Sealing Hollow Fiber in Reactor Cell/Module

A length of a hollow fiber or tubular membrane module 100 may be threaded through the first and second smaller holes in the reactor module 200, 300. In an embodiment, a porous polyamide-imide (e.g., TORLON® (Solvay Advanced Polymers)) hollow fiber 100 with a length of about 4-inches was threaded through the first and second smaller holes of the reactor module 200, 300.

The hollow fiber or tubular membrane module 100 may be mounted (and sealed) in place in the first and second smaller holes with an adhesive such as an epoxy (e.g., transluscent epoxy (3M)). In an embodiment, the hollow fiber 100 was held (and sealed) in place in the first and second smaller holes with a small drop of epoxy on the shell of each fiber where the fiber passes through the aperture. After the epoxy was allowed to cure for about 90 minutes, the excess fiber ends were removed with tweezers, taking care not to crush or block the fiber ends. In an embodiment, a plurality of hollow fibers 100 may be mounted (and sealed) using this same method.

To ensure that the mounted hollow fiber(s) 100 was/were properly sealed and that the ends were not crushed or blocked, the reactor module 400 should be tested for use as a permeation cell by measuring the leak rate and the $N_2$ permeances of the mounted fiber(s), as discussed below.

Performance as Permeation Cell

The reactor module 400 was tested for use as a permeation cell by measuring the leak-rate and the permeance of a known standard. Using a porous polyamide-imide (e.g., TORLON®) hollow fiber as a standard, a $N_2$ permeance of 53,000 G.P.U., which is consistent with the reported values in the literature, was measured with the reactor cell 400.[12,16] Based on flow-based leak tests, the leak-rate was determined to be less than 0.1 psi/hour.

Constant Flow Synthesis of ZIF-8 Membranes

Using a macroporous polyamide-imide (e.g., TORLON®) hollow fiber and the material ZIF-8 as an archetype for a hollow fiber or tubular membrane synthesis, a series of constant flow membrane synthesis experiments were performed. Several examples of ZIF-8 membrane fabrication using this reactor module 400 are described below, and their results are shown in the SEM micrographs of FIGS. 5-8.

Performance in Membrane Synthesis: Static Conditions

Starting with a seeded polyamide-imide (e.g., TORLON®) hollow fiber 100 mounted in the reactor module 400,[12] an aqueous synthesis gel consisting of about 0.22 g Zinc nitrate hexahydrate ($Zn^{+2}$) in about 40 mL of deionized water (DI) (about 0.018 mol/L) and about 9 g 2-methyl imidazole (mIm) in about 80 mL deionized water (DI) (about 1.37 mol/L) was poured on the outer (shell) side surface 105 of the hollow fiber 100. After 6 hours at 30° C., the shell solution was removed and the hollow fiber 100 was thoroughly rinsed with deionized water (DI) and methanol.

Figure 5B:
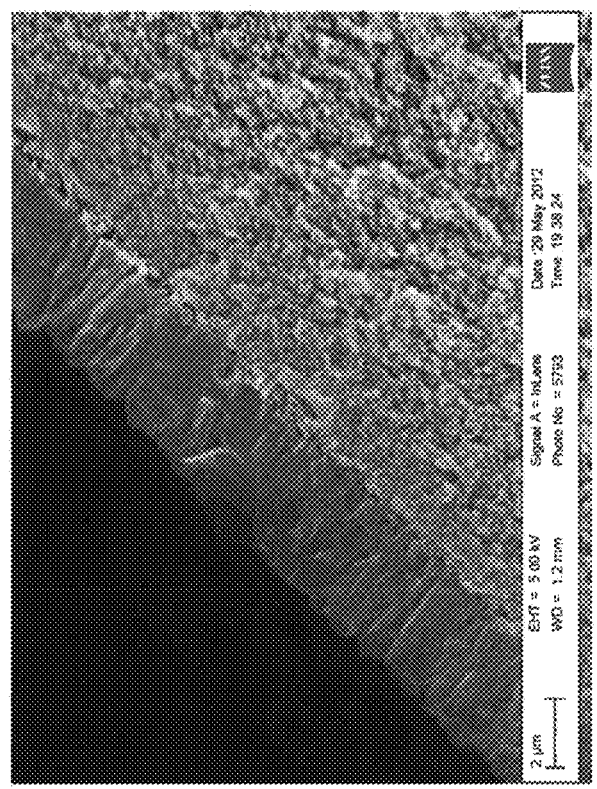
FIG. 5B illustrates a top-view of a SEM micrograph of a ZIF-8 membrane grown on outer (shell) side surface of a seeded polyamide-imide (e.g., TORLON®) hollow fiber.
Figure 5A:
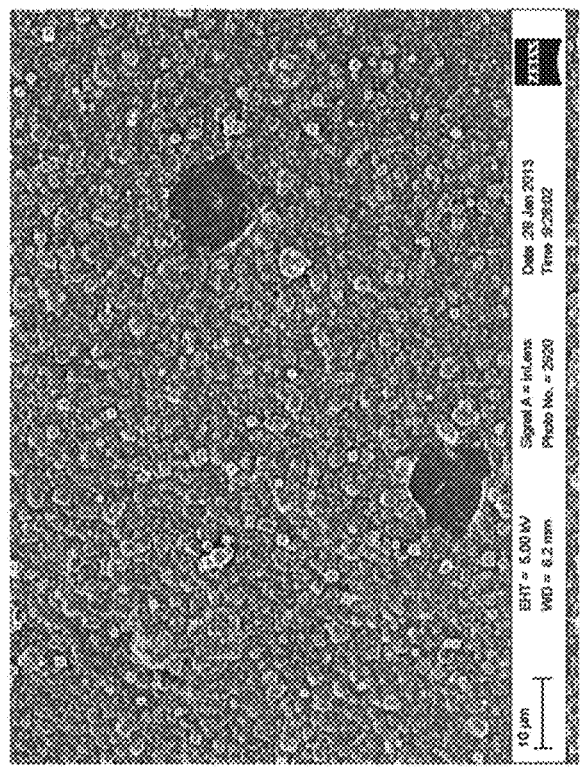
FIG. 5A illustrates a cross-sectional view of a SEM micrograph of a ZIF-8 membrane grown on an outer (shell) side surface of a seeded polyamide-imide (e.g., TORLON®) hollow fiber.

A cross-sectional view of a SEM micrograph of a ZIF-8 membrane grown on an outer (shell) side surface of a seeded polyamide-imide (e.g., TORLON®) hollow fiber is shown in FIG. 5A; and a top view of a SEM micrograph of the ZIF-8 membrane grown on the outer (shell) side surface 105 of the seeded polyamide-imide (e.g., TORLON®) hollow fiber is shown in FIG. 5B. Based upon FIGS. 5A-5B, the ZIF-8 membrane is formed on the outer (shell) side surface 105 of the hollow fiber 100. Cross-sectional images of ZIF-8 inner surface membrane were examined using Hitachi SU 8010 scanning electron microscope after a thin layer of gold was sputtered onto the cross-sectional surface. To obtain a clean cut, the hollow fibers were soaked with a hexane solution for about 30 minutes followed by dipping into liquid nitrogen.

Performance in Membrane Synthesis: Flow Conditions

Reactions that are performed under flowing conditions are easier to control and allow recycling; therefore, ZIF-8 membranes were grown by flowing reagents through the bore 110 of the hollow fiber 100 (see FIGS. 6-7).

First, an aqueous $Zn^{+2}$ solution containing about 0.22 g Zinc nitrate hexahydrate ($Zn^{+2}$) in about 40 mL deionized water (DI) (about 0.018 mol/L) was flowed through the bore 110 at 2 mL/min while an aqueous mIm solution containing 9 g mIm in about 80 mL deionized water (DI) (about 1.37 mol/L) was poured on the outer (shell) side surface 105. The reaction was stopped after 6 hours and the hollow fiber 100 was rinsed with deionized water (DI) and methanol.

Figure 6B:
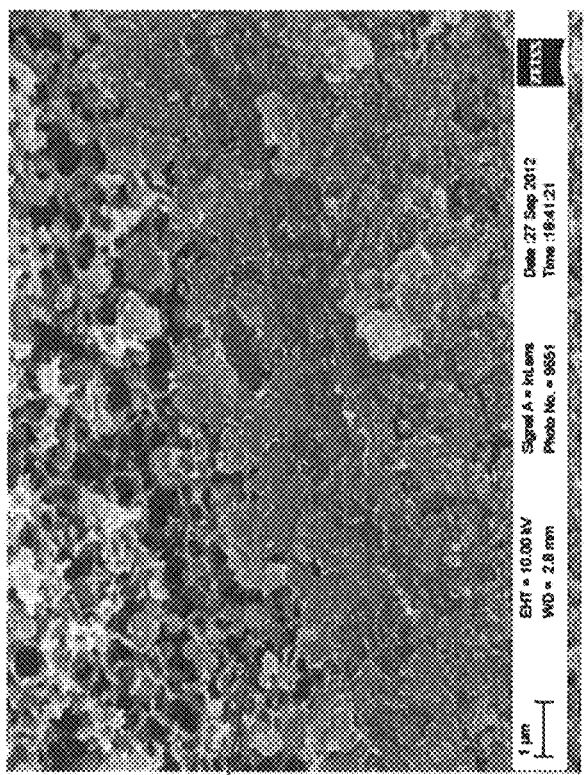
FIG. 6B illustrates a detailed cross-sectional view of a SEM micrograph of a ZIF-8 membrane grown on a polyamide-imide (e.g., TORLON®) hollow fiber under aqueous flow conditions.
Figure 6A:
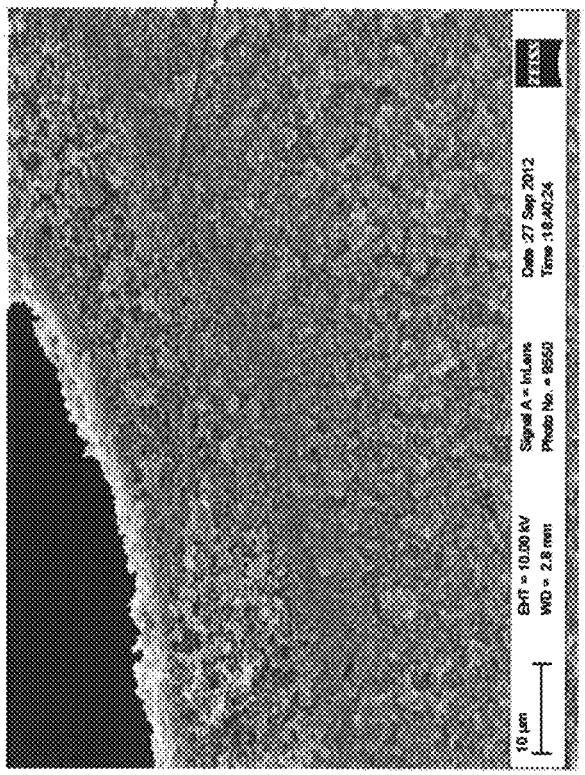
FIG. 6A illustrates a cross-sectional view of a SEM micrograph of a ZIF-8 membrane grown on a polyamide-imide (e.g., TORLON®) hollow fiber under aqueous flow conditions.

A cross-sectional view of a SEM micrograph of a ZIF-8 membrane grown under aqueous flow conditions is shown in FIG. 6A; and a detailed (10x) cross-sectional view of the SEM micrograph of the ZIF-8 membrane grown under aqueous flow conditions is shown in FIG. 6B. Based upon FIGS. 6A-6B, the ZIF-8 membrane is formed on the inner (bore) side surface 110 of the hollow fiber 100.

To determine the effect of solvent, the aforementioned experiment was repeated using a different solvent (i.e., 1-octanol).

Second, a $Zn^{+2}$/1-octanol solution containing about 0.22 g Zinc nitrate hexahydrate ($Zn^{+2}$) in about 40 mL 1-octanol (about 0.018 mol/L) was flowed through the bore 110 at 2 mL/min while a mIm/1-octanol solution containing about 9 g mIm in about 80 mL 1-octanol (about 1.37 mol/L) was poured on the outer (shell) side surface 105. The reaction was stopped after 6 hours and the hollow fiber 100 was rinsed with deionized water (DI) and methanol.

Figure 7B:
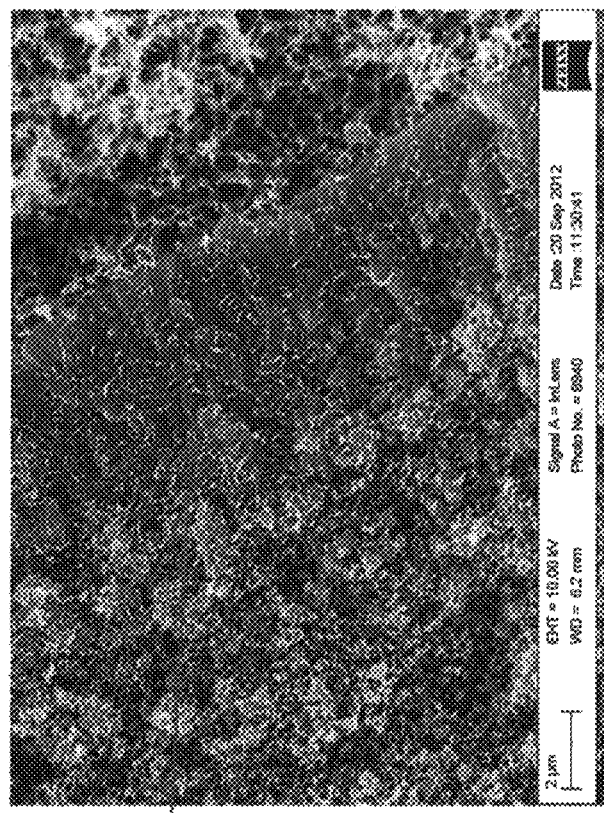
FIG. 7B illustrates a detailed cross-sectional view of a SEM micrograph of ZIF-8 membrane grown on a polyamide-imide (e.g., TORLON®) hollow fiber under 1-octanol flow conditions.
Figure 7A:
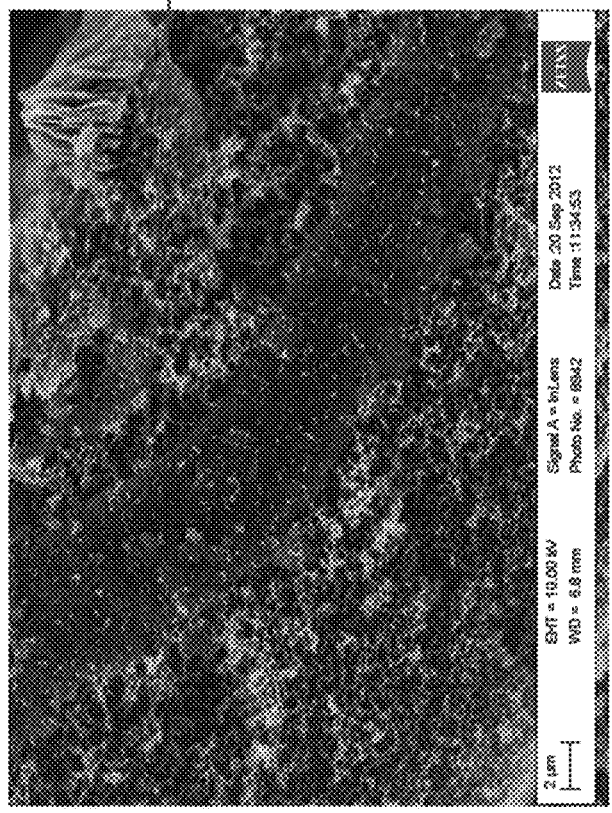
FIG. 7A illustrates a cross-sectional view of a SEM micrograph of a ZIF-8 membrane grown on a polyamide-imide (e.g., TORLON®) hollow fiber under 1-octanol flow conditions.

A cross-sectional view of a SEM micrograph of a ZIF-8 membrane grown under 1-octanol flow conditions is shown in FIG. 7A; and a detailed (10x) cross-sectional view of the SEM image of the ZIF-8 membrane grown under 1-octanol flow conditions is shown in FIG. 7B. Based upon FIGS. 7A-7B, the ZIF-8 membrane is formed on the inner (bore) side surface 110 of the hollow fiber 100.

Accordingly, for both the aqueous (see FIG. 6) and 1-octanol (see FIG. 7) flow systems, the ZIF-8 membrane growth was observed in the inner (bore) side surface 110 of the hollow fiber 100 instead of on the outer (shell) side surface 105.

Performance in Membrane Synthesis: Interfacial Synthesis

The next experiment involved using interfacial synthesis technique whereby immiscible solvents are used as a means to physically separate the organic and inorganic precursors. Specifically, a $Zn^{+2}$/1-octanol solution containing about 0.22 g Zinc nitrate hexahydrate ($Zn^{+2}$) in about 40 mL 1-octanol (about 0.018 mol/L) was flowed at 2 mL/min through the bore 110 while an aqueous mIm solution containing about 9 g mIm in about 80 mL deionized water (DI) (about 1.37 mol/L) was poured into the reactor chamber 345 immersing the outer (shell) side surface 105 of the hollow fiber 100. The reaction was stopped after 6 hours and the hollow fiber 100 was flushed with neat 1-octanol, heptane, and deionized water (DI).

To determine the effect of flow rate, the aforementioned experiment was repeated using a slower flow rate (1 µL/min).

Figure 8B:
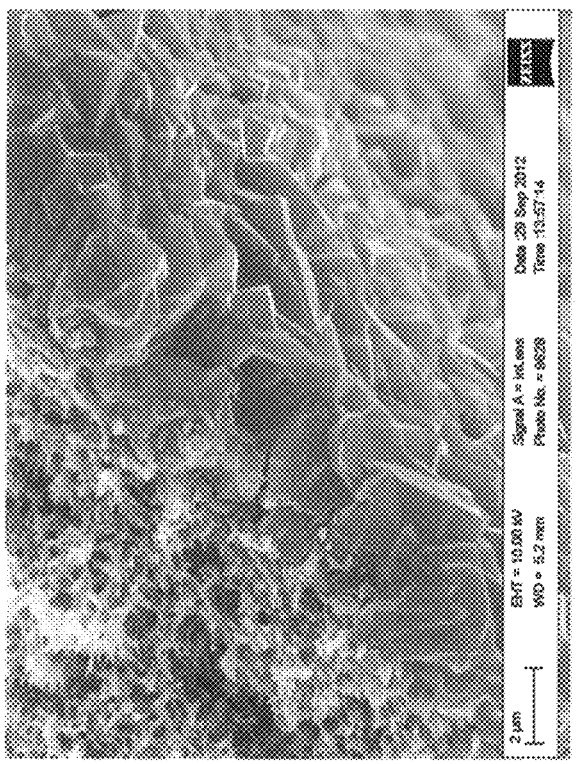
FIG. 8B illustrates a cross-sectional view of a SEM micrograph of a ZIF-8 membrane grown on a polyamide-imide (e.g., TORLON®) hollow fiber using the IMMP approach with 1 μL/min flow rate of a $Zn^{+2}$/1-octanol bore solution and an aqueous mIm shell solution according to an embodiment of the present invention.
Figure 8A:
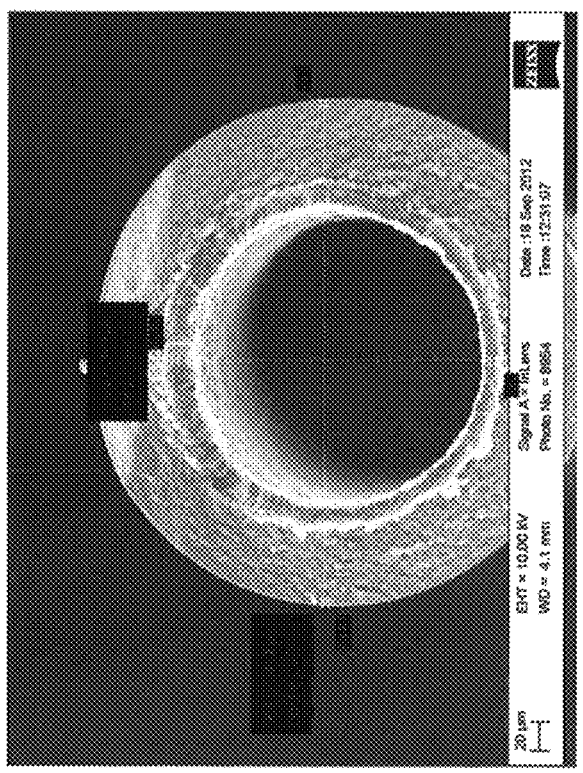
FIG. 8A illustrates a cross-sectional view of a SEM micrograph of a ZIF-8 membrane grown on a polyamide-imide (e.g., TORLON®) hollow fiber using an Interfacial Microfluidic Membrane Processing (IMMP) approach with 2 mL/min flow rate of a $Zn^{+2}$/1-octanol bore solution and an aqueous 2-methyl imidazole (mIm) shell solution according to an embodiment of the present invention.

A cross-sectional view of a SEM micrograph of a ZIF-8 membrane grown under 1-octanol flow conditions of 2 mL/min bore flow rate, using an interfacial system is shown in FIG. 8A; and a cross-sectional view of the SEM micrograph of the ZIF-8 membrane grown under 1-octanol flow conditions of 1 µL/min bore flow rate, using the interfacial system is shown in FIG. 8B.

Accordingly, for the interfacial system, both the 2 mL/min (see FIG. 8A) and 1 µL/min (see FIG. 8B) bore flow rates, the ZIF-8 membrane growth was observed in the interior (bore) side surface 110 of the hollow fiber 100 instead of on the outer (shell) side surface 105.

Table 1 shows the measurement of single-component gas permeation properties of three of the ZIF-8 membranes using the reactor module 400. The entire process of membrane formation and permeation measurement can be done in situ within the same pre-fabricated reactor module 400, thereby avoiding the difficulties associated with previous membrane fabrication processes.

TABLE 1

Measurement of Single-Component Gas Permeation Properties for In-Situ grown ZIF-8 Membrane

| Example | Support | Flow Rate | Thickness (µm) | Permeance (G.P.U.) $N_2$ | $SF_6$ | Selectivity $N_2/SF_6$ |
|---|---|---|---|---|---|---|
| ZIF-8_Outer (see FIGS. 5A-5B) | Torlon Tube | Static | 3 | 800 | 430 | 1.9 |
| ZIF-8_Inner_1 (see FIG. 8A) | Torlon Tube | 2 mL/min | 5-15 | 240 | 100 | 2.4 |
| ZIF-8_Inner_2 (see FIG. 8B) | Torlon Tube | 1 µL/min | 2-3 | 320 | 60 | 5.3 |

Figure 9:
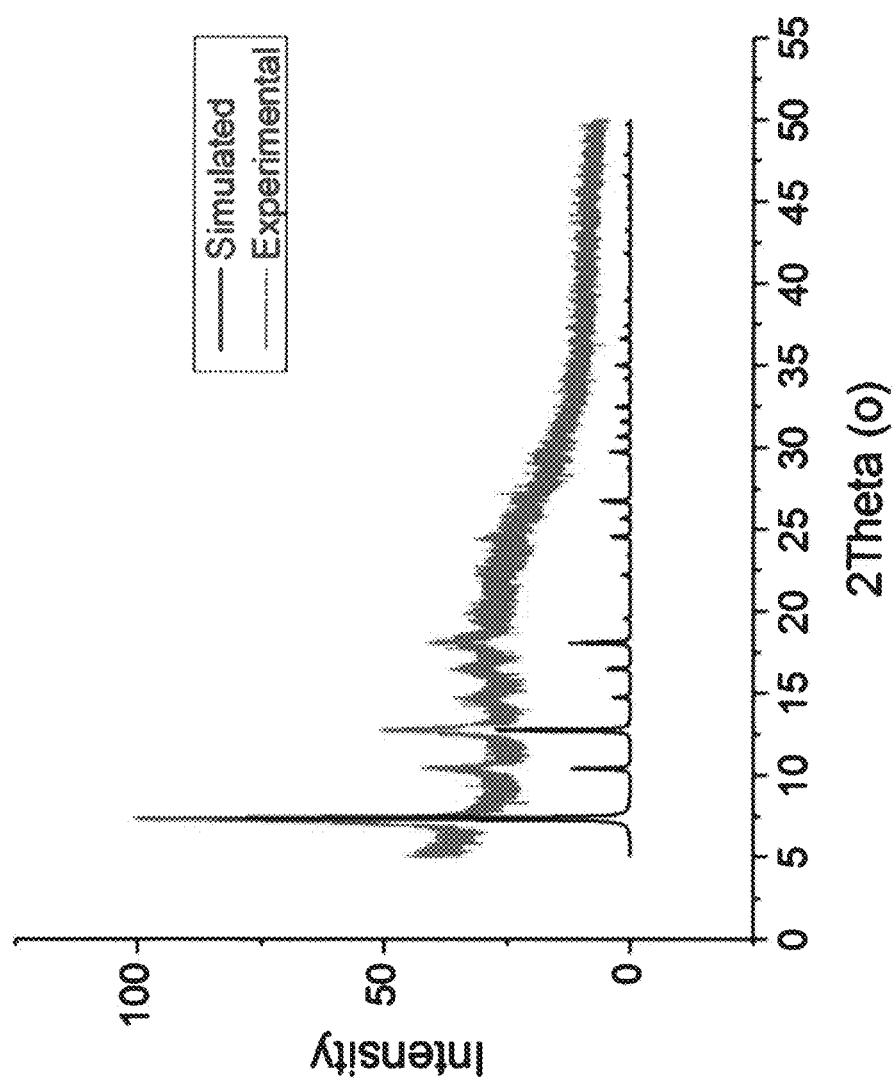
FIG. 9 illustrates a X-ray Diffraction (XRD) chart of 2Theta (°) vs. Intensity for simulated and experimental ZIF-8 membranes, confirming structure of supported ZIF-8 membranes.

An X-ray Diffraction (XRD) chart of 2Theta (°) vs. intensity for simulated and experimental ZIF-8 membranes, confirming the structure of supported ZIF-8 membranes is shown in FIG. 9. XRD patterns were measured on a PANalytical X'Pert Pro diffractometer at room temperature using Cu Kα radiation of λ=0.154 nm and a scanning range of 5-40° 2θ.

Figure 10:
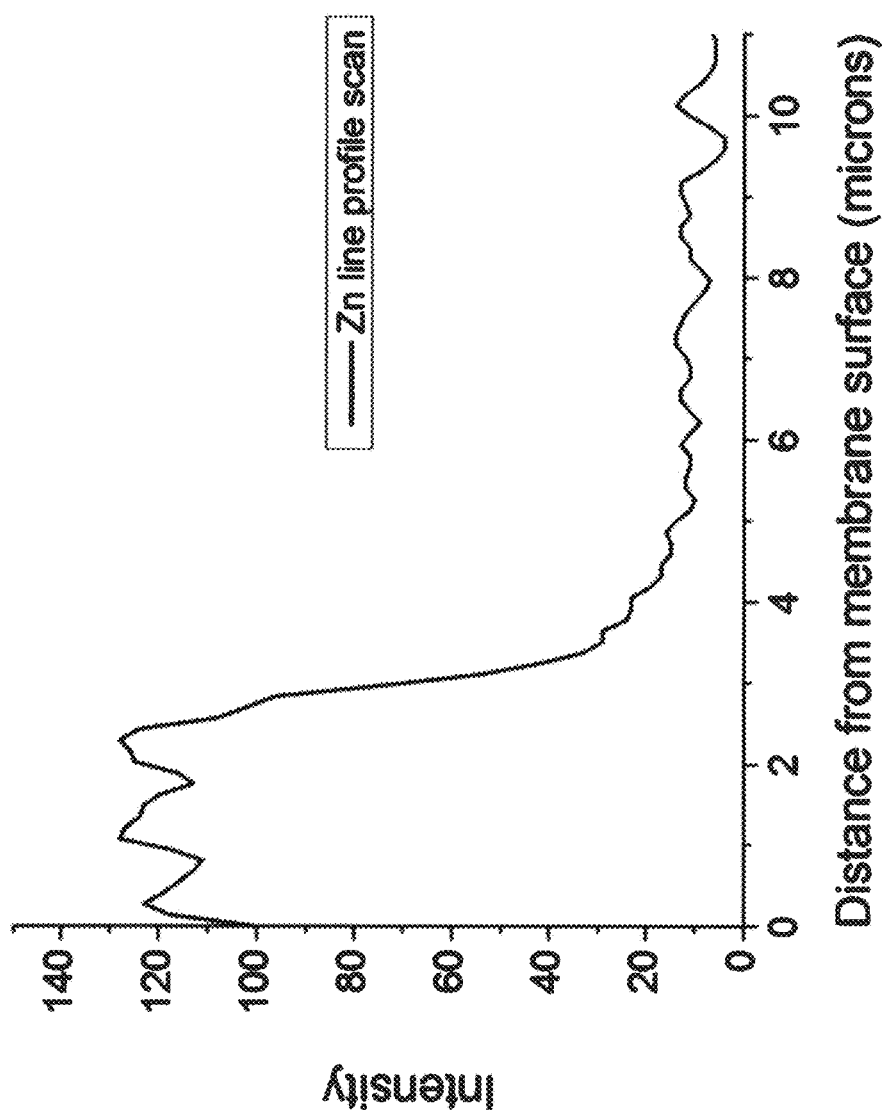
FIG. 10 illustrates an Energy Dispersive X-ray Spectroscopy (EDS) Zinc line profile scan chart of Distance from membrane surface (μm (microns)) vs. Intensity, depicting thickness of membrane to be ~3 μm.

An EDS Zinc line profile scan of distance from membrane surface (µm (microns)) vs. intensity, depicting the thickness of the ZIF-8 membrane to be about 3 µm is shown in FIG. 10.

Performance in Membrane Synthesis: Static, Continuous and Pulsed Flow Conditions In an embodiment, ZIF-8 membranes were grown by flowing reagents through the bore 110 of the hollow fiber 100 (see FIGS. 6-7, 18B-18C) under static, continuous and pulsed flow conditions. See FIGS. 11-12 & 18A.

First, a $Zn^{+2}$/1-octanol solution containing about 0.22 g Zinc nitrate hexahydrate ($Zn^{+2}$) in about 40 mL 1-octanol (about 0.018 mol/L) was continuously flowed through the bore 110 at about 60 µL/hour while an aqueous mIm solution containing about 9 g mIm in about 80 mL deionized water (DI) (about 1.37 mol/L) was poured on the outer (shell) side surface 105. The reaction was stopped after about 9 hours and the hollow fiber 100 was rinsed with 1-octanol, heptanes, deionized water (DI) and methanol.

Second, a $Zn^{+2}$/1-octanol solution containing about 0.22 g Zinc nitrate hexahydrate ($Zn^{+2}$) in about 40 mL 1-octanol (about 0.018 mol/L) was held static in the bore 110 while an aqueous mIm solution containing about 9 g mIm in about 80 mL deionized water (DI) (about 1.37 mol/L) was poured on the outer (shell) side surface 105. The reaction was stopped after about 9 hours and the hollow fiber 100 was rinsed with 1-octanol, deionized water (DI), heptanes and methanol.

Figure 11:
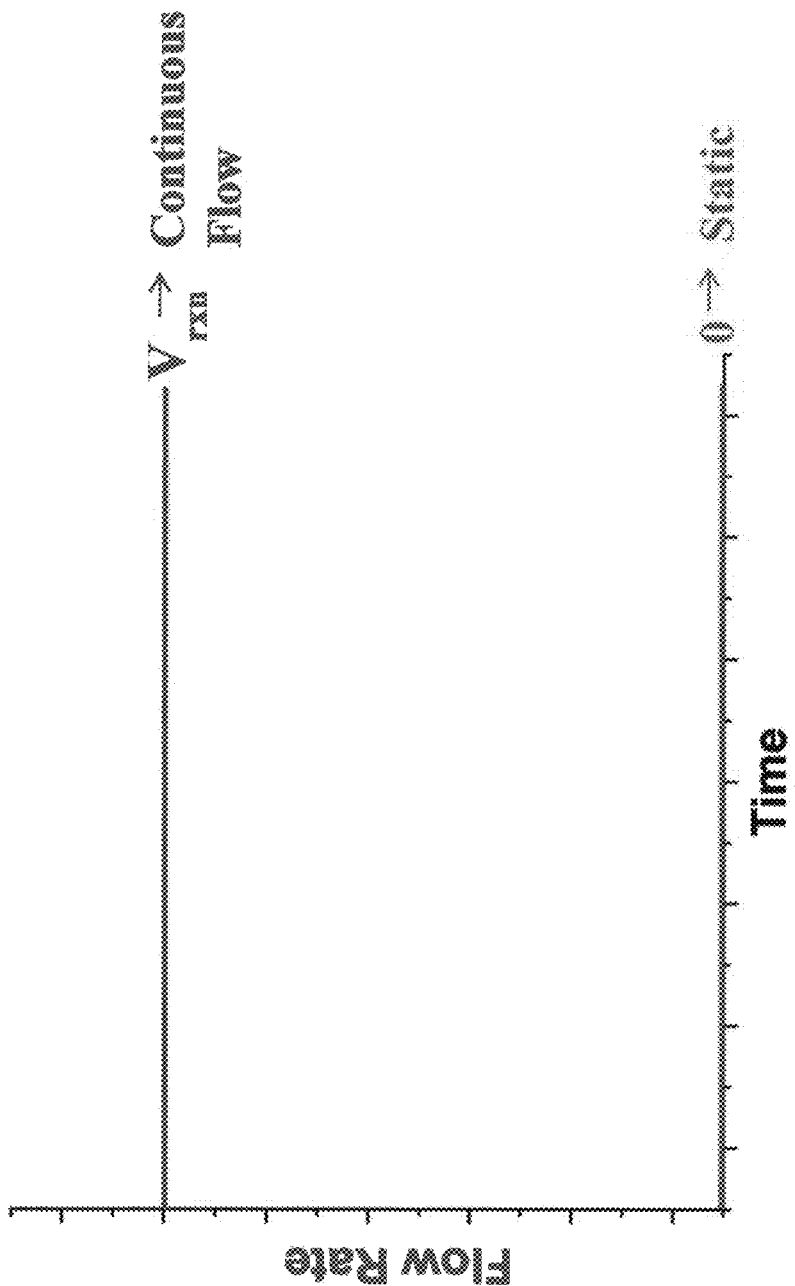
FIG. 11 illustrates a chart of Time vs. Flow Rate for static and continuous flow conditions, showing static growth conditions.

A chart of Time vs. Flow Rate static and continuous flow through the bore 110 of the hollow fiber 100 is illustrated in FIG. 11. No continuous ZIF-8 membrane was formed on the inside of the bore 110 of the hollow fiber 100 under static conditions. In contrast, a continuous ZIF-8 membrane was formed on the inside of the bore 110 of the hollow fiber 100 by continuously flowing bore solution at about 60 µL/hour, however, the membrane had a low $H_2/C_3H_8$ selectivity.

Figure 12:
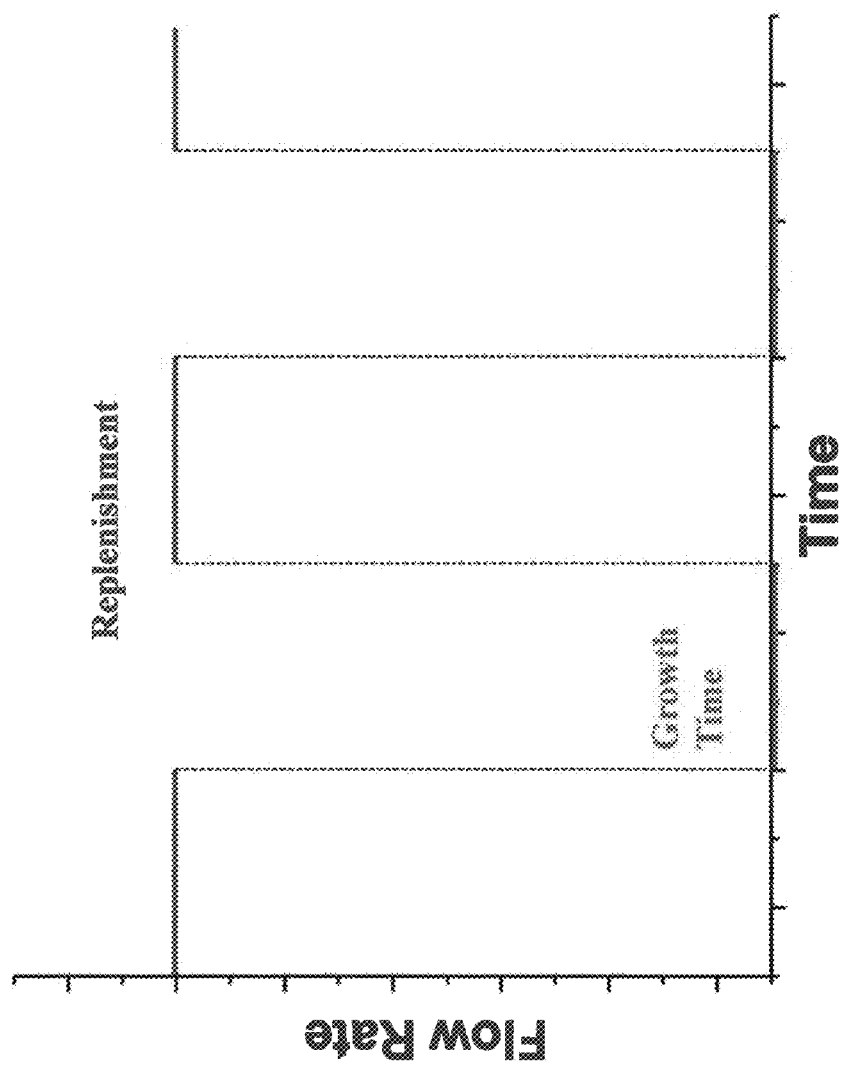
FIG. 12 illustrates a chart of Time vs. Flow Rate for pulsed flow conditions, showing growth and replenishment conditions.
Figure 13:
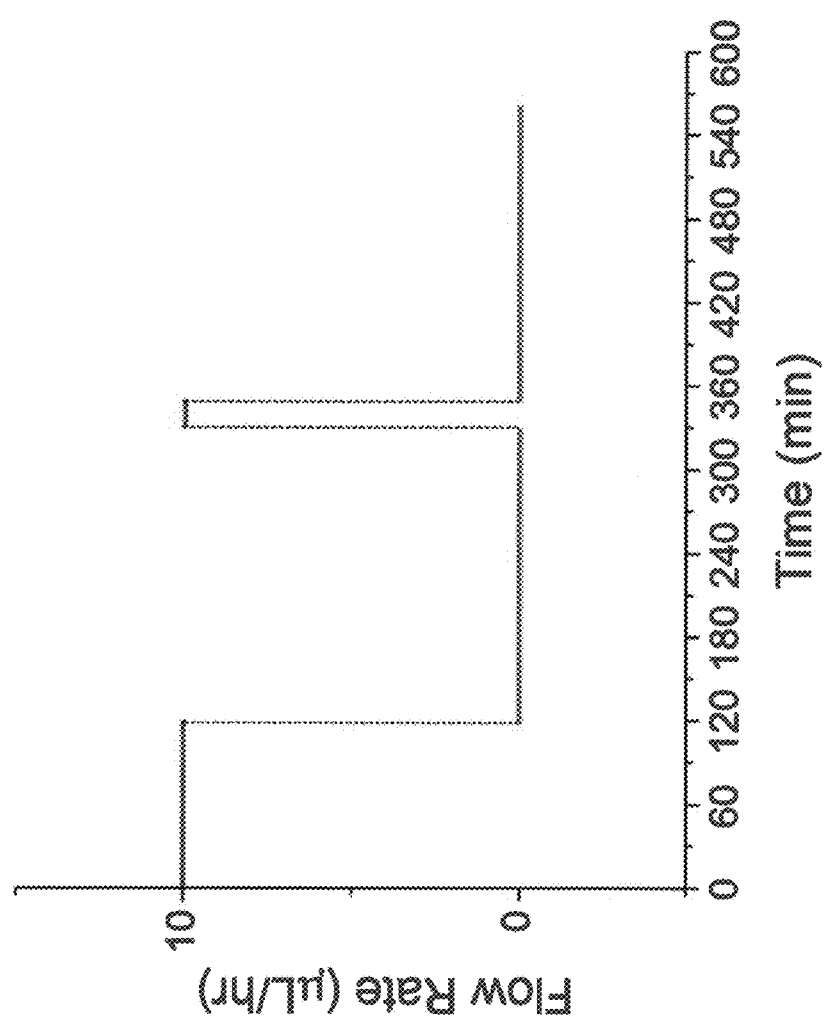
FIG. 13 illustrates a chart of Time (min.) vs. Flow Rate OIL/hour) for pulsed flow conditions, showing growth, static growth and replenishment conditions.

A chart of Time vs. Flow Rate for pulsed flow conditions through the bore 110 of the hollow fiber 100 is illustrated in FIG. 12. Under pulsed flow conditions, a ZIF-8 membrane was formed on the inside of the bore 110 of the hollow membrane 100, and, further, the pulsed-flow membrane had a higher $H_2/C_3H_8$ selectivity than the continuous-flow membrane discussed above.

To further test the effect of flow conditions, the aforementioned experiment was repeated using a one phase aqueous solvent system, a single phase organic solvent system (1-octanol), and a biphasic interfacial solvent system (aqueous/1-octanol), respectively.

First, an aqueous $Zn^{+2}$ solution containing about 0.22 g Zinc nitrate hexahydrate ($Zn^{+2}$) in about 40 mL deionized water (DI) (about 0.018 mol/L) was flowed through the bore 110 at about 10 µL/hour while an aqueous mIm solution containing about 9 g mIm in about 80 mL deionized water (DI) (about 1.37 mol/L) was poured on the outer (shell) side surface 105. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step. The reaction was stopped after about 9 hours and the hollow fiber 100 was rinsed with deionized water (DI) and methanol.

Second, a $Zn^{+2}$/1-octanol solution containing about 0.022 g Zinc nitrate hexahydrate ($Zn^{+2}$) in about 40 mL 1-octanol (about 0.018 mol/L) was flowed through the bore 110 at about 10 µL/hour while a mIm/1-octanol solution containing about 9 g mIm in about 80 mL 1-octanol (about 1.37 mol/L) was poured on the outer (shell) side surface 105. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step. The reaction was stopped after about 9 hours and the hollow fiber 100 was rinsed with 1-octanol, deionized water (DI), heptanes and methanol.

Third, a $Zn^{+2}$/1-octanol solution containing about 0.11 g Zinc nitrate hexahydrate ($Zn^{+2}$) in about 40 mL 1-octanol (about 0.018 mol/L) was flowed through the bore 110 at about 10 µL/hour while an aqueous mIm solution containing about 9 g mIm in about 80 mL deionized water (DI) (about 1.37 mol/L) was poured on the outer (shell) side surface 105. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step. The reaction was stopped after about 9 hours and the hollow fiber 100 was rinsed with 1-octanol, deionized water (DI), heptanes and methanol.

Figure 18A:
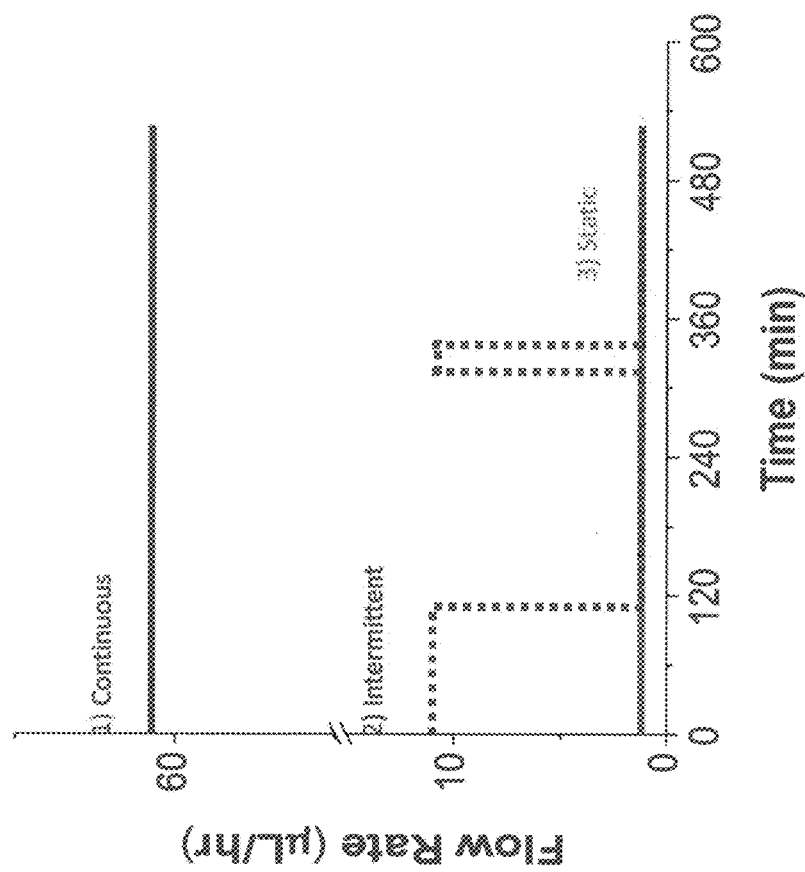
FIG. 18A illustrates a chart of Time (minutes) vs. Flow Rate OIL/hour), showing static, continuous and intermittent flow conditions used to synthesize ZIF-8 membranes on the inner (bore) side surface of a polyamide-imide (e.g., TORLON®) hollow fibers as in Example 1.

A chart of Time vs. Flow Rate summarizing the examined static, continuous and pulsed flow conditions through the bore 110 of the hollow fiber 100 is illustrated in FIG. 18A.

Figure 18C:
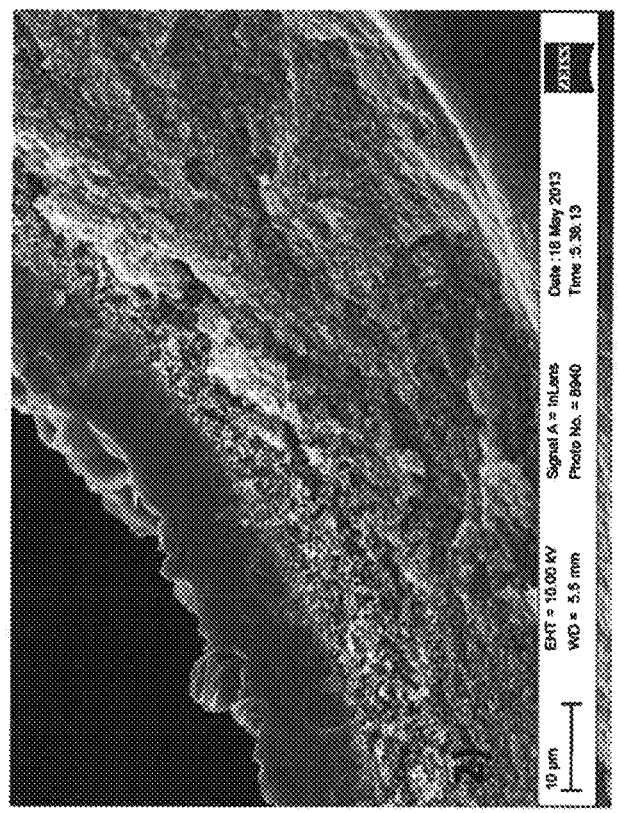
FIG. 18C illustrates a cross-sectional view of a SEM micrograph of a ZIF-8 membrane grown in a polyamide-imide (e.g., TORLON®) hollow fiber using the IMMP approach with a continuous flow of a $Zn^{+2}$/1-octanol bore solution, depicting a continuous ZIF-8 membrane (about 3 μm thick) on the inner (bore) side surface of the hollow fiber.
Figure 18B:
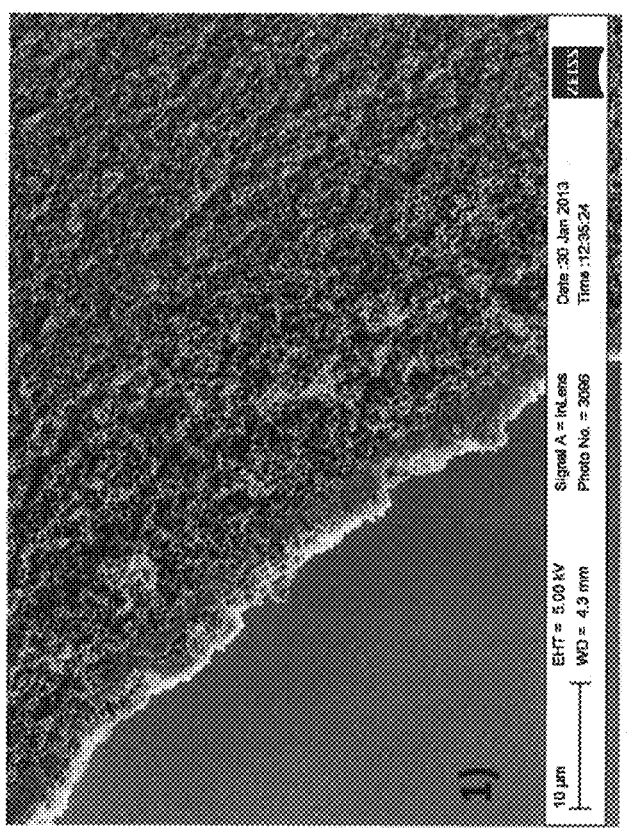
FIG. 18B illustrates a cross-sectional view of a SEM micrograph of a ZIF-8 membrane grown in a polyamide-imide (e.g., TORLON®) hollow fiber using the IMMP approach with a static flow of a $Zn^{+2}$/1-octanol bore solution, depicting a discontinuous particle coating on the inner (bore) side surface of the hollow fiber.

A cross-sectional view of a SEM micrograph of a ZIF-8 membrane grown in a polyamide-imide (e.g., TORLON®) hollow fiber with a static flow of a $Zn^{+2}$/1-octanol bore solution is illustrated in FIG. 18B. As shown in FIG. 18B, static growth conditions produce dense, non-continuous coatings of ZIF-8 particles in the inner (bore) side surface 110 of the hollow fiber 100. This is due to the lack of sufficient $Zn^{2+}$ ions available in the microscale bore of the hollow fiber 100 to sustain the film growth after the initial nucleation and growth of ZIF-8 crystals at the inner (bore) side surface 110 of the hollow fiber 100.

Figure 15:
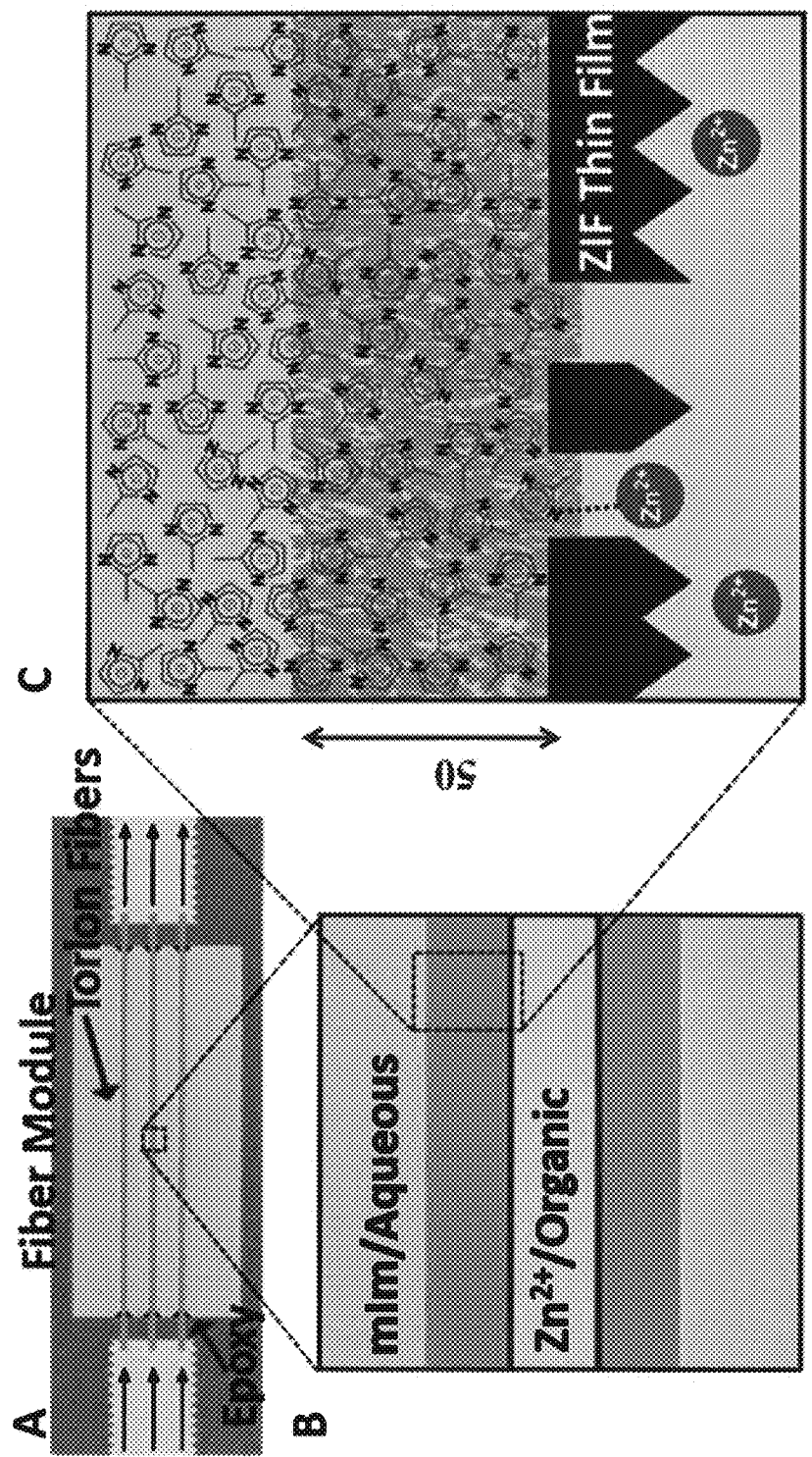
FIG. 15 illustrates a schematic of the IMMP approach: (A) depicts a side view of a plurality of hollow fibers (orange) mounted in a reactor cell, (B) depicts an exploded side view of hollow fiber support during synthesis, showing $Zn^{2+}$ ions being supplied by a 1-octanol solution (light red) flowing through the bore of the hollow fiber and methylimidazole linkers being supplied on the outer (shell) side of the hollow fiber in an aqueous solution (light blue), and (C) depicts a further exploded view of hollow fiber support during synthesis, showing the membrane forming on the inner surface of the hollow fiber by reaction of the two precursors to form a polycrystalline ZIF-8 layer (dark blue)

A cross-sectional view of a SEM micrograph of a ZIF-8 membrane grown on a polyamide-imide (e.g., TORLON®) hollow fiber with continuous flow of a $Zn^{+2}$/1-octanol bore solution is illustrated in FIG. 18B. As shown in FIG. 18C, continuous flow growth conditions produced a thin, continuous membrane (about 3 μm thickness) that was formed in the inner (bore) side surface 110 of the hollow fiber 100. This is due to the relatively rapid transport of reactants to the interface under continuous flow, leading to rapid formation and closure of the ZIF-8 layer. The growing membrane itself becomes a barrier between the two immiscible solvents, and confines the liquid-liquid interface into the gaps and interstices between the ZIF-8 crystals. See FIG. 15.

Figure 18D:
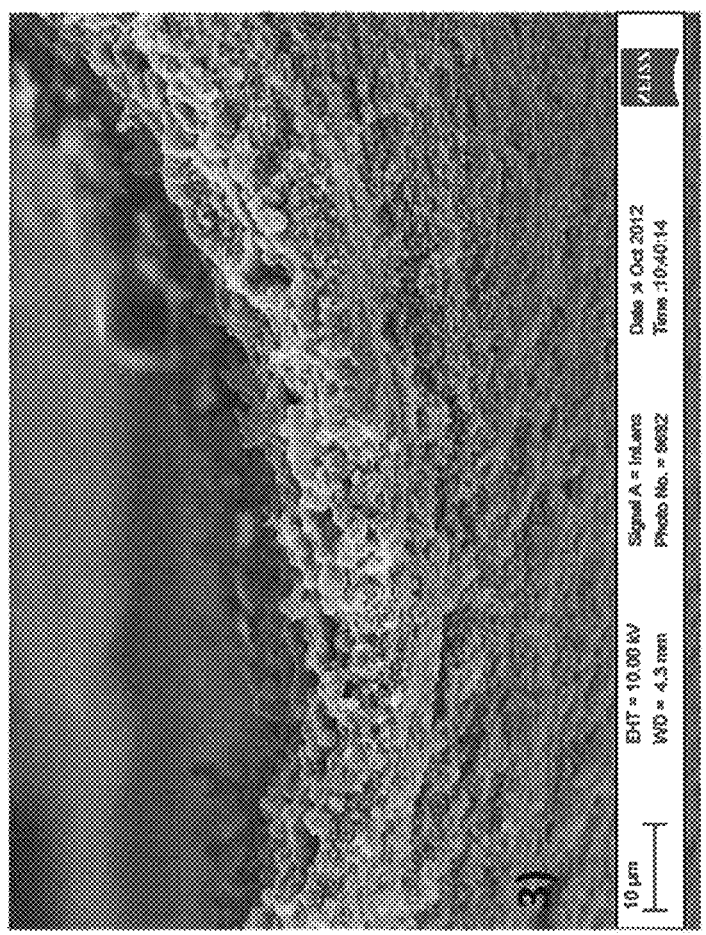
FIG. 18D illustrates a cross-sectional view of a SEM micrograph of a ZIF-8 membrane grown in a polyamide-imide (e.g., TORLON®) hollow fiber using the IMMP approach with an intermittent flow of a $Zn^{+2}$/1-octanol bore solution, depicting a continuous ZIF-8 membrane (about 8 μm thick) on the inner (bore) side surface of the hollow fiber.

A cross-sectional view of a SEM micrograph of a ZIF-8 membrane grown on a polyamide-imide (e.g., TORLON®) hollow fiber with intermittent flow of a $Zn^{+2}$/1-octanol bore solution is illustrated in FIG. 18D. As shown in FIG. 18D, intermittent flow growth conditions produced a thicker, continuous membrane (about 8 μm thickness) that was formed in the inner (bore) side surface 110 of the hollow fiber 100. The flow profile included an initial continuous growth step, followed by a static growth step interrupted by a brief reactant replenishment step. In an embodiment, the flow profile included an initial continuous growth step of about 10 μL/hour of a $Zn^{+2}$/1-octanol bore solution for about 2 hours, followed by a static growth step of about 0 μL/hour of the bore solution for about 3.5 hours, followed by a replenishment step of about 10 μL/hour of bore solution for about 20 minutes and followed by another static growth step of about 0 μL/hour of bore solution for about 3.5 hours. See FIG. 18A: flow profile 2.

Figure 17B:
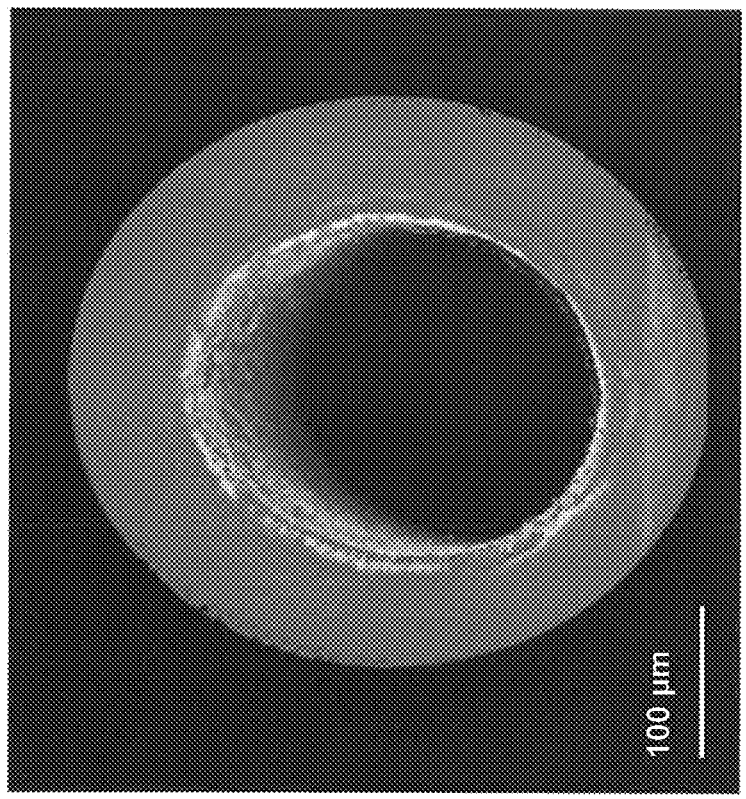
FIG. 17B illustrates an EDS elemental maps of carbon (red) and superimposed zinc (green) showing the localization of the ZIF-8 membrane on the inner (bore) side surface of the polyamide-imide (e.g., TORLON®) hollow fiber as in Example 1.
Figure 17A:
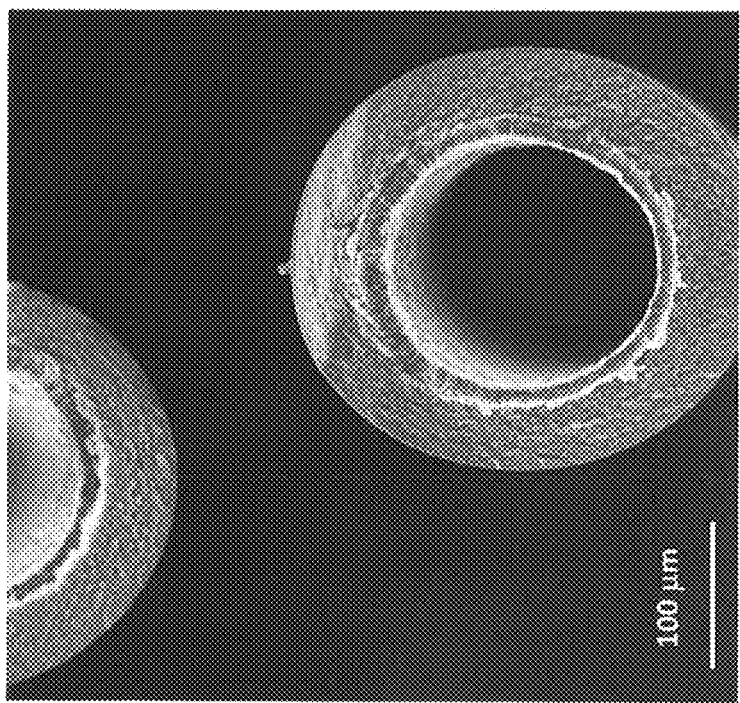
FIG. 17A illustrates a cross-sectional view of a SEM micrograph of a ZIF-8 membrane grown in polyamide-imide (e.g., TORLON®) hollow fiber on the inner (bore) side surface by manipulating the location of the two reactants (i.e., zinc nitrate hexahydrate and mIm) and the two solvents (i.e., deionized water (DI) and 1-octanol) as in Example 1.
Figure 19:
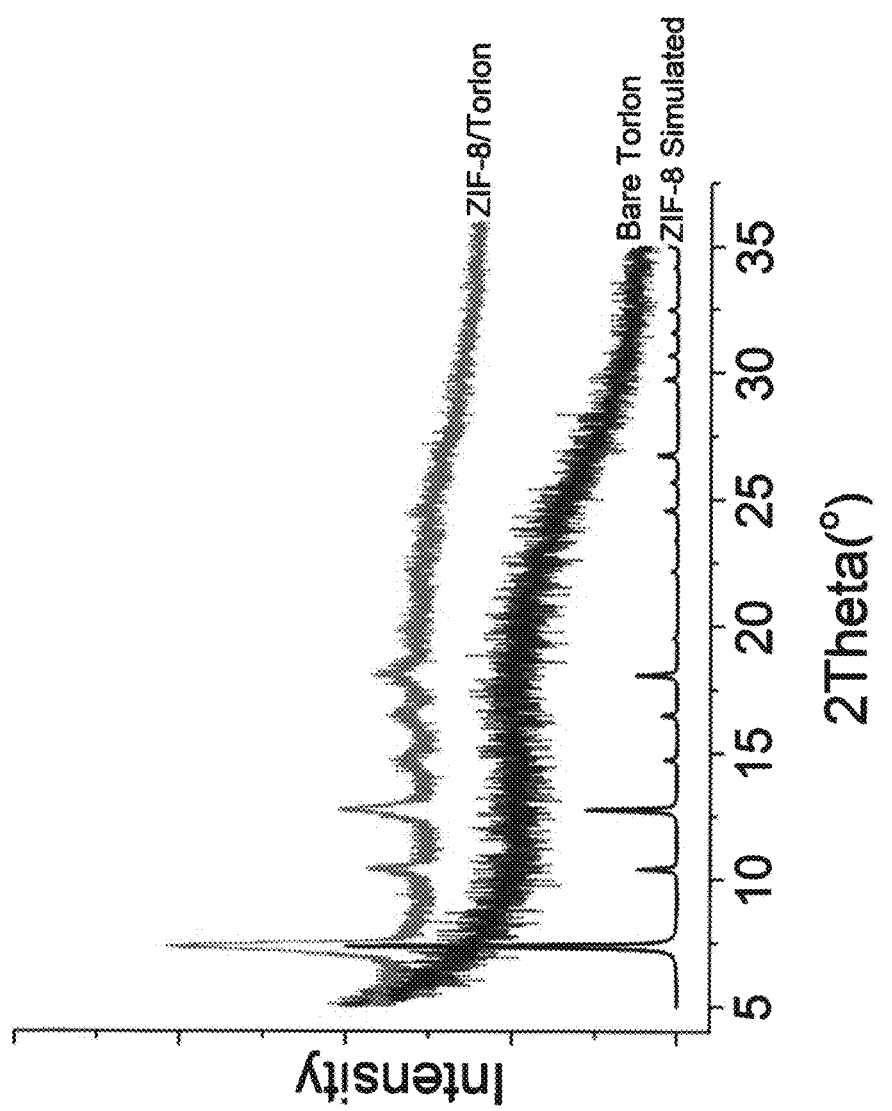
FIG. 19 illustrates an XRD pattern confirming crystal structure of ZIF-8 membrane grown on a polyamide-imide (e.g., TORLON®) hollow fiber using the IMMP approach with intermittent flow of a $Zn^{+2}$/1-octanol bore solution as in Example 1.
Figure 20B:
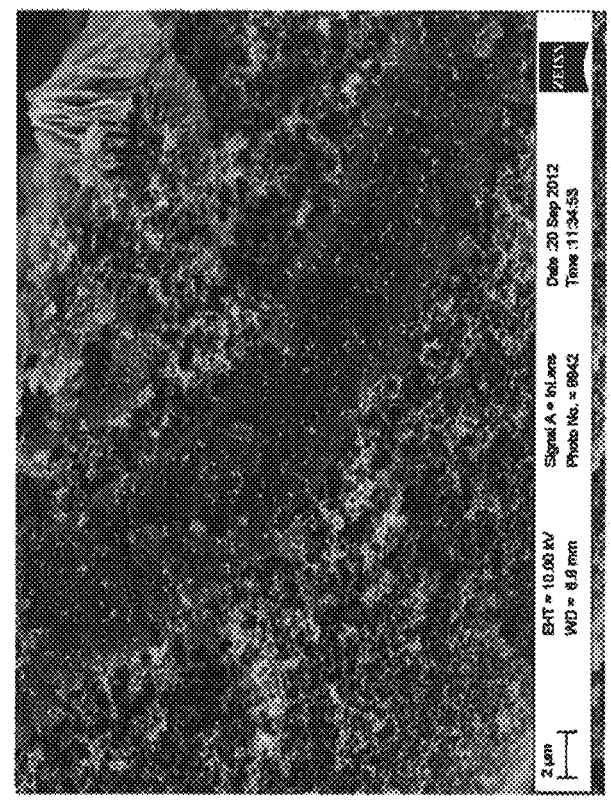
FIG. 20B illustrates a cross-sectional view of a SEM micrograph of a ZIF-8 membrane grown in a polyamide-imide (e.g., TORLON®) hollow fiber closer to an inner (bore) side surface by manipulating the location of the two reactants (i.e., zinc nitrate hexahydrate and mIm) and the two solvents (i.e., DI and 1-octanol) as in Example 3.
Figure 20A:
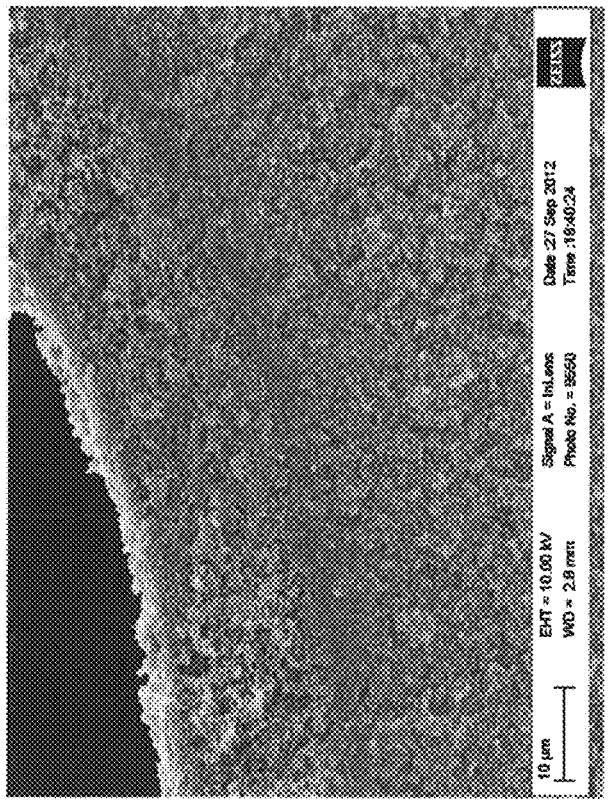
FIG. 20A illustrates a cross-sectional view of a SEM micrograph of a ZIF-8 membrane grown in a polyamide-imide (e.g., TORLON®) hollow fiber closer to an inner (bore) side surface by manipulating the location of the two reactants (i.e., zinc nitrate hexahydrate and mIm) and the two solvents (i.e., DI and 1-octanol) as in Example 2.
Figure 20D:
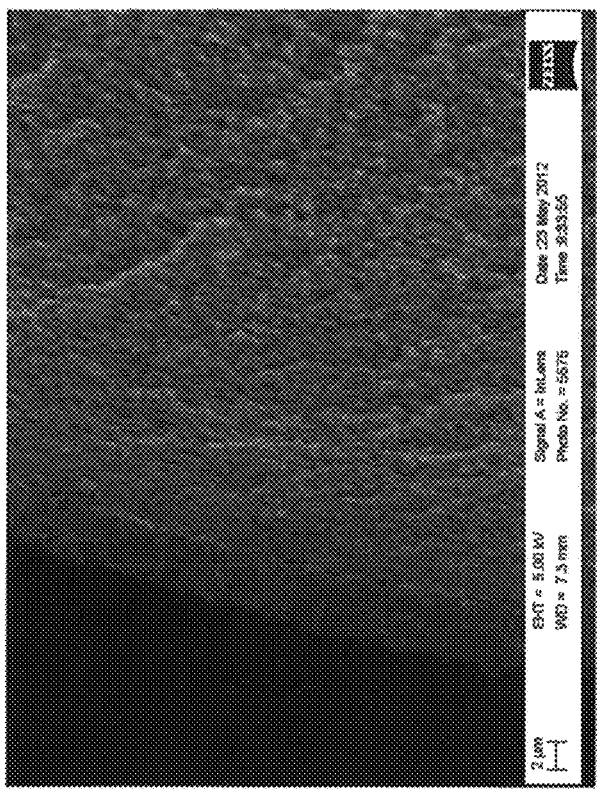
FIG. 20D illustrates a cross-sectional view of a SEM micrograph of a ZIF-8 membrane grown in a polyamide-imide (e.g., TORLON®) hollow fiber closer to an outer (shell) side surface by manipulating the location of the two reactants (i.e., zinc nitrate hexahydrate and mIm) and the two solvents (i.e., DI and 1-octanol) as in Example 5.
Figure 20C:
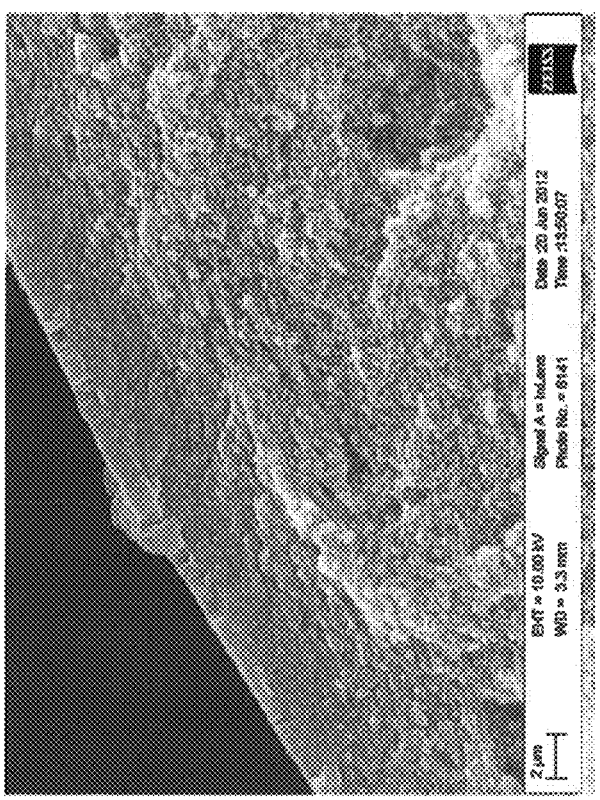
FIG. 20C illustrates a cross-sectional view of a SEM micrograph of a ZIF-8 membrane grown in a polyamide-imide (e.g., TORLON®) hollow fiber closer to an outer (shell) side surface by manipulating the location of the two reactants (i.e., zinc nitrate hexahydrate and mIm) and the two solvents (i.e., DI and 1-octanol) as in Example 4.
Figure 21A:
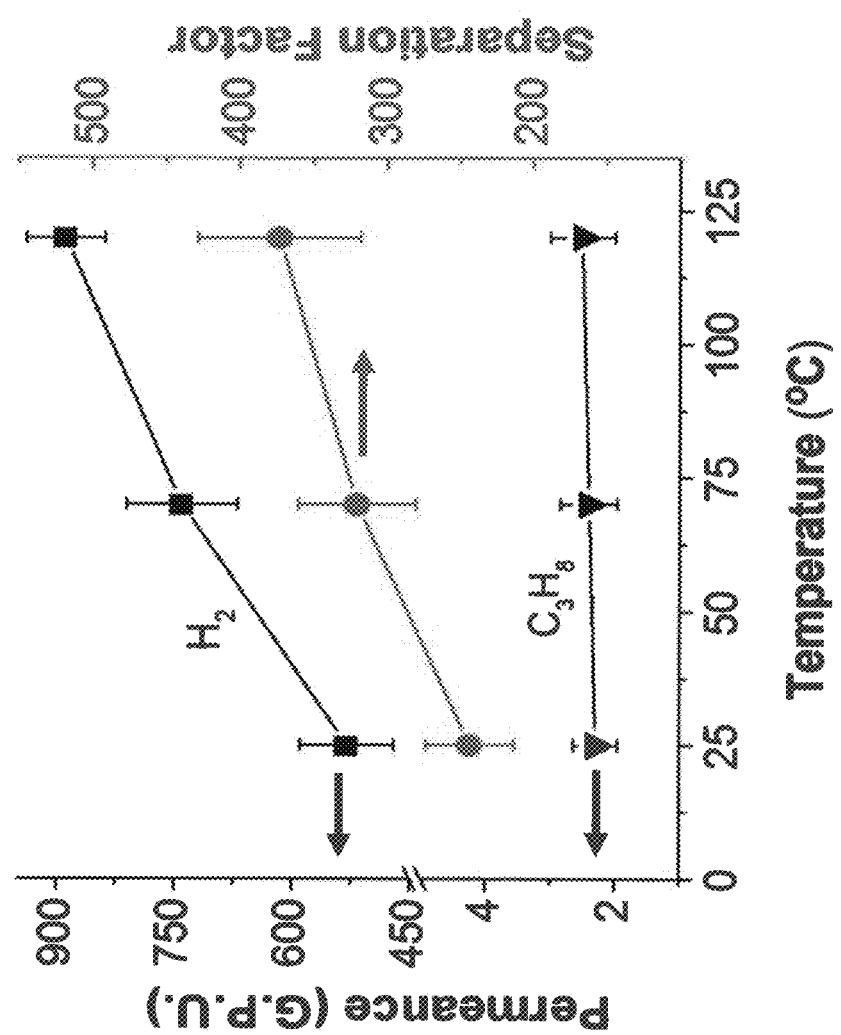
FIG. 21A illustrates a chart of Temperature (° C.) vs. Permeance (G.P.U.) and Separation Factor, showing binary $H_2/C_3H_8$ permeation characteristics for an equimolar feed mixture on a ZIF-8 membrane grown in a polyamide-imide (e.g., TORLON®) hollow fiber using the IMMP system and capping ends of the hollow fiber with poly(dimethylsilozane) (PDMS)
Figure 21B:
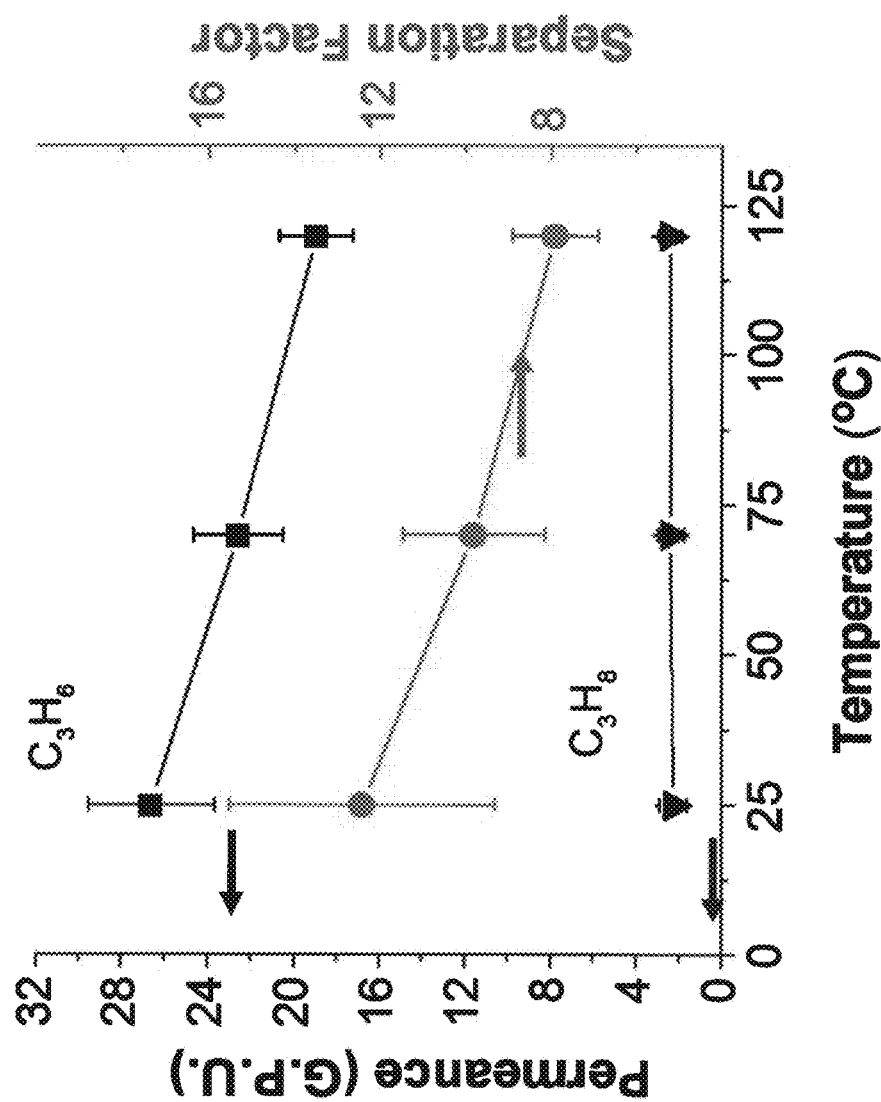
FIG. 21B illustrates a chart of Temperature (° C.) vs. Permeance (G.P.U.) and Separation Factor, showing binary $C_3H_6/C_3H_8$ permeation characteristics for an equimolar feed mixture on a ZIF-8 membrane grown in a polyamide-imide (e.g., TORLON®) hollow fiber using the IMMP system and capping ends of the hollow fiber with PDMS.
Figure 22A:
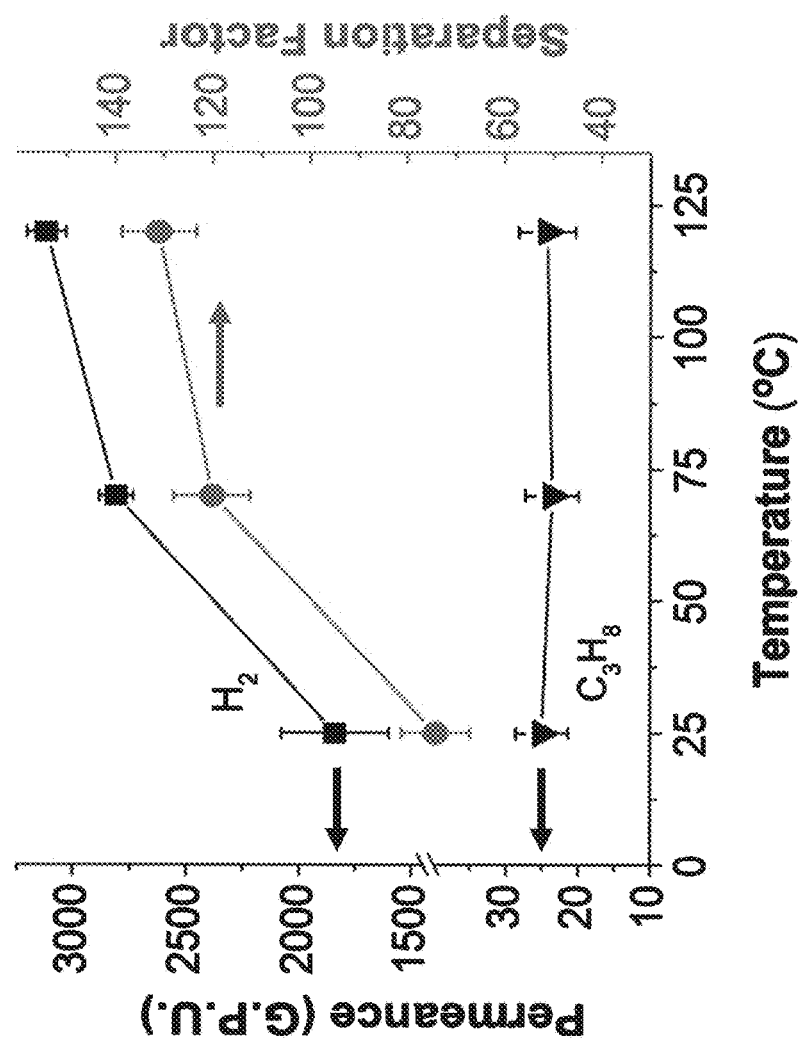
FIG. 22A illustrates a chart of Temperature (° C.) vs. Permeance (G.P.U.) and Separation Factor, showing binary permeation characteristics for an equimolar $H_2/C_3H_8$ feed mixture on a ZIF-8 membrane grown in polyamide-imide (e.g., TORLON®) hollow fiber using the IMMP system.
Figure 22B:
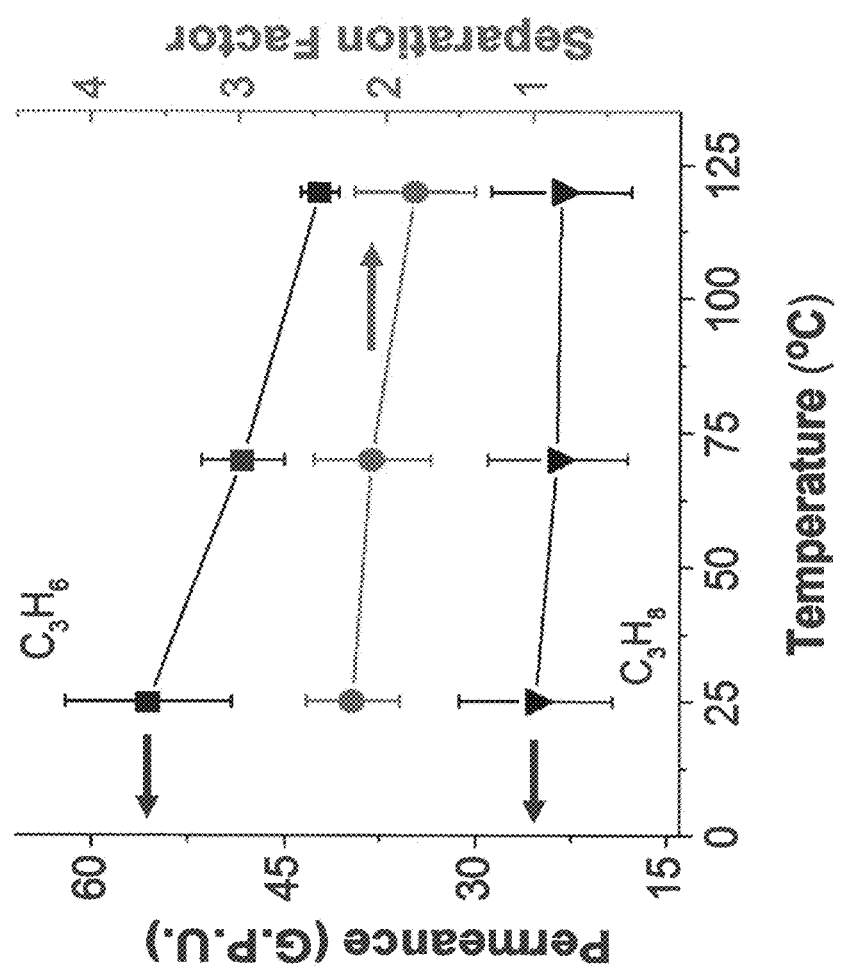
FIG. 22B illustrates a chart of Temperature (° C.) vs. Permeance (G.P.U.) and Separation Factor, showing binary permeation characteristics for an equimolar $C_3H_6/C_3H_8$ feed mixture on a ZIF-8 membrane grown in polyamide-imide (e.g., TORLON®) hollow fiber using the IMMP system.

Additionally, FIG. 17A shows lower-magnification images of ZIF-8 membranes formed on two hollow fibers 100; and FIG. 17B shows the zinc elemental mapping, confirming the localization of the membrane to the inner (bore) side surface 110 of the hollow fiber 100. X-ray diffraction confirmed the ZIF-8 crystal structure of the film. See FIG. 19.

Performance in Membrane Synthesis: Pulsed Flow Synthesis

Table 2 shows measurement of gas and liquid permeation properties for various supported ZIF-8 membranes.

TABLE 2

Measurement of Gas and Liquid Permeation Properties

| | | Thickness | Permeance (G.P.U.) | | | | | | |
|---|---|---|---|---|---|---|---|---|---|
| Reference | Support | (μm) | $H_2$ | $CO_2$ | $CH_4$ | $C_3H_8$ | $C_6H_{14}$ | $C_6H_{12}$ | $C_6H_6$ |
| Y. Pan | YSZ Tube | 2.5 | 4400 | 1200 | 360 | 4 | | | |
| Y. Pan | $Al_2O_3$ Disk | 2.5 | 1100 | 390 | 240 | 2 | | | |
| AJB | Torlon ® | 8 | 2900 | 500 | 270 | 60 | 2600 | 600 | 290 |

Figure 14:
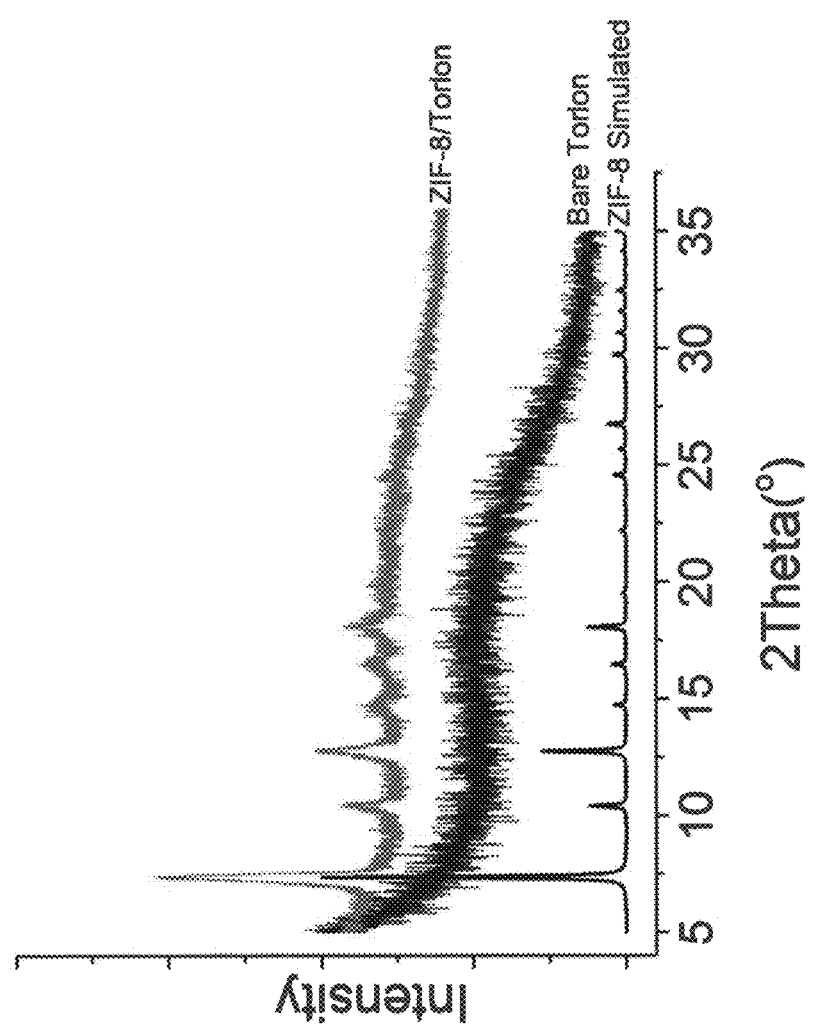
FIG. 14 illustrates a X-ray Diffraction (XRD) chart of 2Theta (°) vs. Intensity for simulated and experimental ZIF-8 membranes on polyamide-imide (e.g., TORLON®) hollow fiber, confirming formation and structure of supported ZIF-8 membranes on inner (bore) side surface of hollow fiber.

A X-ray Diffraction (XRD) chart of 2Theta (°) vs. intensity for simulated and experimental ZIF-8 membranes and polyamide-imide (e.g., TORLON®) hollow fiber, confirming formation and structure of supported ZIF-8 membranes on the bore 110 of the hollow fiber 100 is shown in FIG. 14. XRD patterns were measured on a PANalytical X'Pert Pro diffractometer at room temperature using Cu Kα radiation of λ=0.154 nm and a scanning range of 5-40° 2θ.

Performance in Membrane Synthesis: Pulsed Flow and Stirred Synthesis

Table 3 shows the single-component gas permeation properties of a ZIF-8 membrane measured in situ using the reactor module 400 and gently stirring the outer (shell) side 105 solution.

TABLE 3

Measurement of Single-Component Gas Permeation Properties for grown ZIF-8 Membrane

| Sample | Support | Flow Rate | Thickness (μm) | Permeance (G.P.U.) | | | Selectivity |
|---|---|---|---|---|---|---|---|
| | | | | $H_2$ | $CH_4$ | $C_3H_8$ | $H_2/C_3H_8$ |
| ZIF-8_10 μL/hour Pulsed | Torlon ® | 10 μL/hour | 8 | 4200 | 400 | 35 | 120 |

Table 4 shows measurement of gas permeation properties of a ZIF-8 membrane when the mixture feed consisted of a 1:1 $H_2/C_3H_8$ mixture.

TABLE 4

Measurement of Mixed Gas Permeation Properties

| Sample | Support | Thickness (μm) | Permeance (G.P.U.) $H_2$ | $C_3H_8$ | Selectivity $H_2/C_3H_8$ |
|---|---|---|---|---|---|
| Y. Pan | YSZ Tube | 2.5 | 2000 | 4 | 470 |
| ZIF-8_1010 μL/hour | Torlon ® | 8 | 2250 | 26.4 | 85 |

Y. Pan, et al., J. MEMBR. SCI. 421 (2012) 292.

Pulsed-Flow Synthesis of ZIF-8 Membranes

Using a macroporous polyamide-imide (e.g., TORLON®) hollow fiber and the material ZIF-8 as an archetype for a hollow fiber or tubular membrane synthesis, a series of pulsed flow membrane synthesis experiments were performed. Table 5 shows combinations of precursor solutions and locations (bore/shell) tested to synthesize ZIF-8 membranes using a reactor module 400. Several examples of ZIF-8 membrane fabrication using the reactor module 400 are described below, and their results are shown in the SEM micrographs of FIGS. 17A-17B, 18A-18D and 20A-20D. For the experiments, a temperature probe 490 set at 30° C. was inserted into the reactor module 400 during membrane growth.

TABLE 5

Combinations of Precursor Solutions Tested to Synthesize ZIF-8 Membranes Using IMMP Approach

| Example | Bore Solution | Shell Solution | Molar Ratio $Zn^{+2}$/mIm | Membrane Location |
|---|---|---|---|---|
| 1 (see FIGS. 17A-17B and 18A-18D) | 0.018 mol/L $Zn^{+2}$ in 1-octanol | 1.37 mol/L mIm in DI | 75 | Bore (inner surface) |
| 2 (see FIG. 20A) | 0.018 mol/L $Zn^{+2}$ in 1-octanol | 1.37 mol/L mIm in DI | 75 | In fiber, closer to bore surface |
| 3 (see FIG. 20B) | 0.018 mol/L $Zn^{+2}$ in 1-octanol | 1.37 mol/L mIm in DI | 75 | In fiber, closer to bore surface |
| 4 (see FIG. 20C) | 1.37 mol/L mIm in DI | 0.018 mol/L $Zn^{+2}$ in 1-octanol | 75 | Shell (outer surface) |
| 5 (see FIG. 20D) | 1.37 mol/L mIm in DI | 0.018 mol/L $Zn^{+2}$ in 1-octanol | 75 | Shell (outer surface) |

Example 1

First, about 10 mL of neat 1-octanol solvent was flowed through a bore 110 using a syringe pump.

Second, about 3 mL of a $Zn^{+2}$/1-octanol solution containing 0.11 g Zinc nitrate hexahydrate ($Zn^{+2}$) in about 40 mL 1-octanol (about 0.018 mol/L) was flowed through the bore 110 of a horizontal hollow fiber 100 at a flow rate of about 10 μL/hour. In an embodiment, a limited $Zn^{+2}$/1-octanol solution containing about 0.005 mol/L to about 0.1 mol/L $Zn^{+2}$ in 1-octanol may be used. In an embodiment, a limited $Zn^{+2}$/1-octanol solution containing about 0.01 mol/L to about 0.03 mol/L $Zn^{+2}$ in 1-octanol may be used. Increasing the $Zn^{+2}$ concentration to about 0.03 mol/L leads to reduction of the membrane thickness and increase in crystal nucleation.

About 70 mL of an aqueous mIm solution containing about 9 g mIm in about 80 mL dionized water (DI) (about 1.37 mol/L) was slowly poured into the reactor module 400, immersing the outer (shell) side surface 105 of the hollow fiber 100. In an embodiment, an excess aqueous mIm solution containing about 0.5 mol/L to about 10 mol/L mIm in deionized water (DI) may be used, provided that the mIm concentration is in excess. In an embodiment, an excess aqueous mIm solution containing about 1.2 mol/L to about 1.6 mol/L mIm in deionized water (DI) may be used.

The aqueous mIm (shell) solution was gently stirred at about 60 rpm to prevent the formation of local concentration gradients. In an embodiment, the aqueous mIm solution may be stirred at about 40 rpm to about 80 rpm.

After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step. In an embodiment, the bore solution flows at a first flow rate for a first period, the bore solution is stopped for a second period, the bore solution flows at a second flow rate for a third period and the bore solution is stopped for a fourth period. In an embodiment, the first and second flow rate is about 10 μL/hour to about 100 μL/hour. In an embodiment, the first period is about 1 hour to about 3 hours, the second period is about 3 hours to about 4 hours, the third period is about 10 minutes to about 30 minutes and the fourth period is about 3 hours to about 4 hours.

To stop the reaction, about 10 mL of neat 1-octanol solvent was pushed through the bore 110 while the outer (shell) side surface 105 was soaked in about 70 mL of neat DI (and replaced three times) to remove the excess $Zn^{+2}$. Next, about 10 mL heptanes were pushed through the bore 110 while the outer (shell) side surface 105 was soaked in about 70 mL heptanes to remove the 1-octanol. Next, about 10 mL of hexane was pushed through the bore 110 while the outer (shell) side surface 105 was soaked in hexane to remove the heptanes. Then, about 20 mL methanol was flowed through the bore 110 while the outer (shell) side surface 105 was soaked in about 70 mL methanol to remove the DI. The reactor module 400 was allowed to air dry at least 4 days before permeation testing.

Example 2

First, about 10 mL DI was first flowed through the bore 110 followed by about 3 mL of an aqueous $Zn^{+2}$ (bore) solution (about 0.018 mol/L). About 70 mL of an aqueous mIm solution (about 1.37 mol/L) was added to the outer (shell) side surface 105 (i.e., slowly poured into the reactor module 400 and was gently stirred at about 60 rpm to prevent the formation of local concentration gradients) while the aqueous $Zn^{+2}$ (bore) solution was flowed at about 10 μL/hour for about 2 hours. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step.

To stop the reaction, about 20 mL DI was flowed through the bore 110 while the outer (shell) side surface 105 was soaked in about 70 mL of neat DI (and replaced three times) to remove the excess $Zn^{+2}$. Then, about 20 mL methanol was flowed through the bore 110 while the outer (shell) side surface 105 was soaked in about 70 mL methanol to remove the DI. The reactor cell 400 was allowed to air dry at least 4 days before permeation testing.

Example 3

First, about 10 mL 1-octanol was first flowed through the bore 110 followed by about 3 mL of a $Zn^{+2}$/1-octanol (bore) solution (about 0.018 mol/L). About 70 mL of an mIm/1-octanol solution (about 1.37 mol/L) was added to the outer (shell) side surface 105 while the $Zn^{+2}$/1-octanol (bore) solution was flowed at about 10 µL/hour for about 2 hours. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step.

To stop the reaction, about 10 mL neat 1-octanol solvent was pushed through the bore 110 while the outer (shell) side surface 105 was soaked in about 70 mL of neat 1-octanol solvent. Then, about 10 mL of heptanes were pushed through the bore 110 while the outer (shell) side surface 105 was soaked in about 70 mL of heptanes to remove the 1-octanol. Then, about 10 mL of hexane was pushed through the bore 110 while the outer (shell) side surface 105 was soaked in about 70 mL of hexane to remove the heptanes. Then, about 10 mL of methanol was pushed through the bore 110 while the outer (shell) side surface 105 was soaked in about 70 mL of methanol. The reactor module 400 was allowed to air dry at least 4 days before permeation testing.

Example 4

First, about 10 mL neat 1-octanol solvent was flowed through the bore 110 followed by about 3 mL of mIm/1-octanol (bore) solution (about 1.37 mol/L).

Second, about 70 mL of an aqueous $Zn^{+2}$ solution (about 0.018 mol/L) was added to the outer (shell) side surface 105 while the mIm/octanol (bore) solution was flowed at about 10 µL/hour for about 2 hours. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step.

To stop the reaction, about 10 mL of neat 1-octanol solvent was pushed through the bore 110 while the outer (shell) side surface 105 was soaked in about 70 mL of neat DI (and replaced three times) to remove the excess $Zn^{+2}$. Next, about 10 mL heptanes were pushed through the bore 110 while the outer (shell) side surface 105 was soaked in about 70 mL heptanes to remove the 1-octanol. Next, about 10 mL of hexane was pushed through the bore 110 while the outer (shell) side surface 105 was soaked in hexane to remove the heptanes. Then, about 20 mL methanol was flowed through the bore 110 while the outer (shell) side surface 105 was soaked in about 70 mL methanol to remove the DI. The reactor module 400 was allowed to air dry at least 4 days before permeation testing.

Example 5

First, about 10 mL DI was flowed through the bore 110 followed by about 3 mL of an aqueous mIm solution (about 1.37 mol/L).

Second, about 70 mL of a $Zn^{+2}$/1-octanol solution (about 0.018 mol/L) was added to the outer (shell) side surface 105 while the aqueous mIm (bore) solution was flowed at about 10 µL/hour for about 2 hours. After about 2 hours of bore solution flow, the pump was stopped for about 3.5 hours to provide a static growth step. After about 3.5 hours, the pump was continued for about 20 minutes. After about 20 minutes, the pump was stopped for another 3.5 hours to provide another static growth step.

The reaction was stopped by flowing about 20 mL DI through the bore 110 and exchanging the outer (shell) side surface 105 solution with neat 1-octanol solvent. Then, about 10 mL heptanes were flowed through the bore 110 while the outer (shell) side surface 105 was soaked in about 70 mL of heptanes. Then, about 10 mL hexane was flowed through the bore 110 while the outer (shell) side surface 105 was soaked in about 70 mL of hexane. Then, about 20 mL methanol was flowed through the bore 110 while the outer (shell) side surface 105 was soaked in about 70 mL of methanol.

Capping of Hollow Fiber Ends

A capping solution containing poly(dimethylsiloxane) (PDMS) (e.g., SYLGARD® 184 (Corning)) in a solvent may be used as a filler material to cap both ends of the hollow fiber 100. In an embodiment, a capping solution containing about 9 wt % PDMS in heptane was heated at about 90° C. with vigorous stirring for about 4 hours to thermally crosslink the PDMS. In an embodiment, a capping solution of about 8 wt % to 10 wt % PDMS in heptane may be used.

After cooling to about 25° C., about 2 µL droplet was applied from a pipette to each hollow fiber 100 end, using capillary action. Immediately upon applying the sealing solution, Argon gas was immediately flowed through the inner (bore) side 110 and followed by curing at about 120° C. for about 2 hours.

Performance of ZIF-8 Membranes Made Using IMMP Reactor Cell/Module

Figure 16:
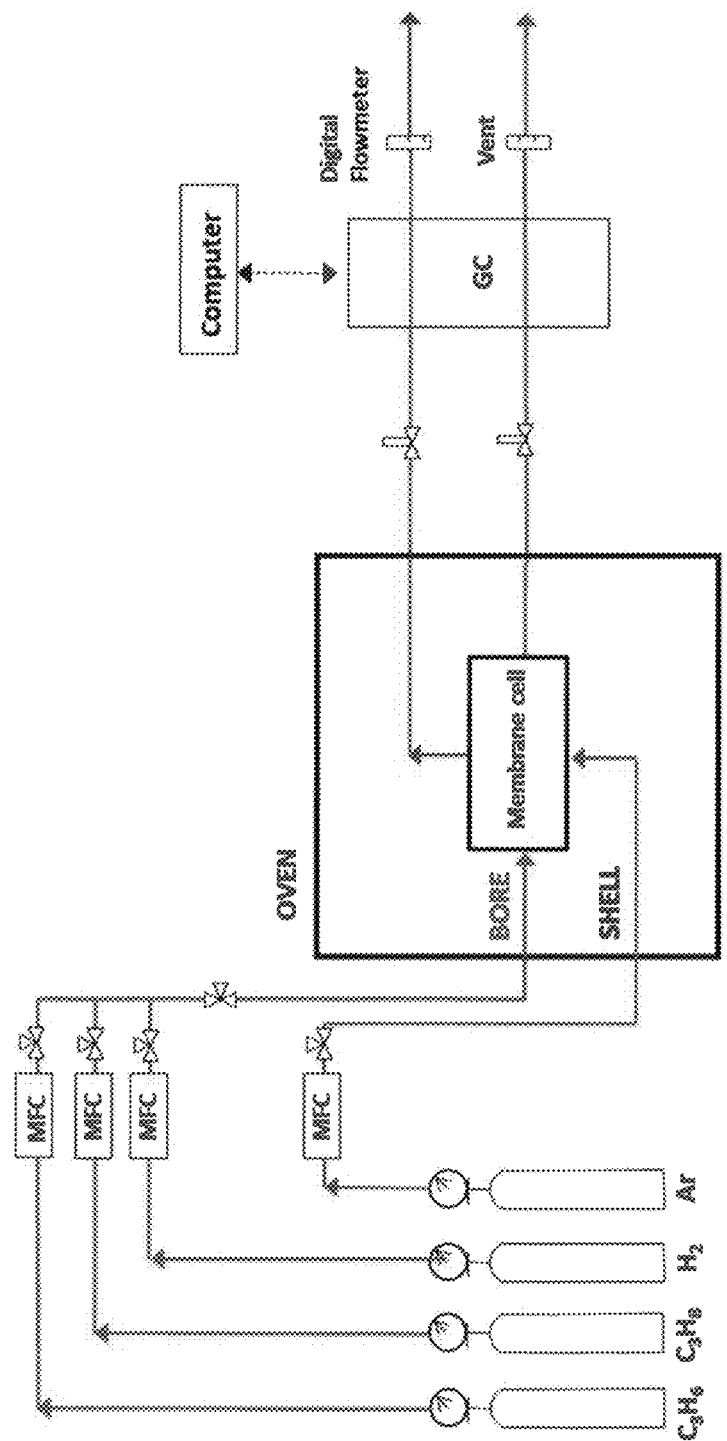
FIG. 16 illustrates a schematic of steady-state gas permeation measurement apparatus, with the reactor cell functioning as the permeation cell.

The separation properties of the ZIF-8 membrane grown on the inner bore of the polyamide-imide (e.g., TORLON®) hollow fiber 100 were characterized by hydrogen ($H_2$)/propane ($C_3H_8$) and propylene ($C_3H_6$)/propane ($C_3H_8$) binary equimolar mixture permeation as a function of temperature, with the reactor module 400 directly acting as a permeation cell. See FIG. 16. In an embodiment, the feed mixture may be selected from the group consisting of hydrogen/hydrocarbons, hydrogen/propane, propylene/propane and butenes/butanes.

A steady-state Wicke Kallenbach technique was used to test binary $H_2/C_3H_8$ and $C_3H_6/C_3H_8$ mixtures. Specifically, 1:1 feed mixtures were flowed through a bore 110 of the ZIF-8 membrane grown on the polyamide-imide (e.g., TORLON®) hollow fiber 100 at about 20 mL/min while an argon sweep gas was flowed across an outer (shell) side surface 105 of the hollow fiber 100 at about 20 mL/minute. See e.g., FIGS. 21A-21B, 22A-22B and 23A-23B. In FIGS. 21A-21B, 22A-22B and 23A-23B, the error bars were estimated from characterization of three independent ZIF-8 membrane samples.

A gas chromatograph with TCD and FID detectors was used to determine the composition of permeate. At least 3

GC injections were collected (median permeance values were reported) at each temperature after waiting 30 minutes for steady-state conditions.

The ZIF-8 membranes in polyamide-imide (e.g., TORLON®) hollow fibers 100 were formed using the reaction conditions of Example 1 under intermittent flow conditions (see FIG. 18A: flow profile 2). The as-made ZIF-8 membranes on polyamide-imide (e.g., TORLON®) hollow fibers 100 exhibited clear molecular sieving properties: high $H_2$ permeances, sharp $H_2/C_3H_8$ separation factors as high as 125 at 120° C. (see FIG. 22A), and strong temperature dependence of $H_2$ permeance with temperature, indicating activated molecular transport through the ZIF-8 pores. Further, the example ZIF-8 membrane on polyamide-imide (e.g., TORLON®) hollow fiber 100 proved to be robust showing no decline in permeation properties after six weeks of testing and multiple heating/cooling cycles.

While the permeation properties were dominated by molecular sieving, the $C_3$ isomer (especially $C_3H_8$) permeances were much larger than those expected from previous studies[8, 17-20] and prevented a high $C_3H_6/C_3H_8$ separation factor. See FIG. 23B. It was hypothesized that the high $C_3$ isomer permeances were due to both molecular transport through the ZIF-8 membrane as well as due to bypassing of the ZIF-8 membrane by the feed molecules through the ends of the fiber. See FIG. 24A.

Figure 24A:
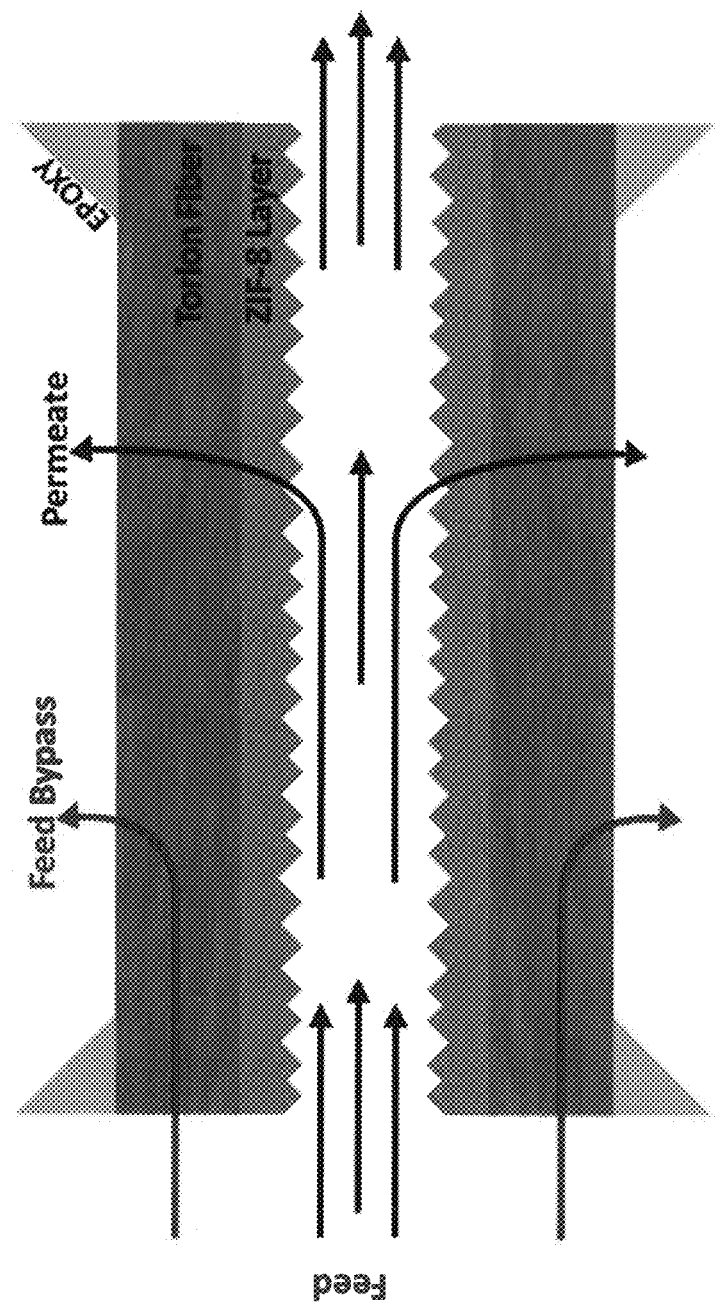
FIG. 24A illustrates a schematic showing feed gas molecules bypassing the ZIF-8 membrane through the hollow fiber ends.
Figure 24B:
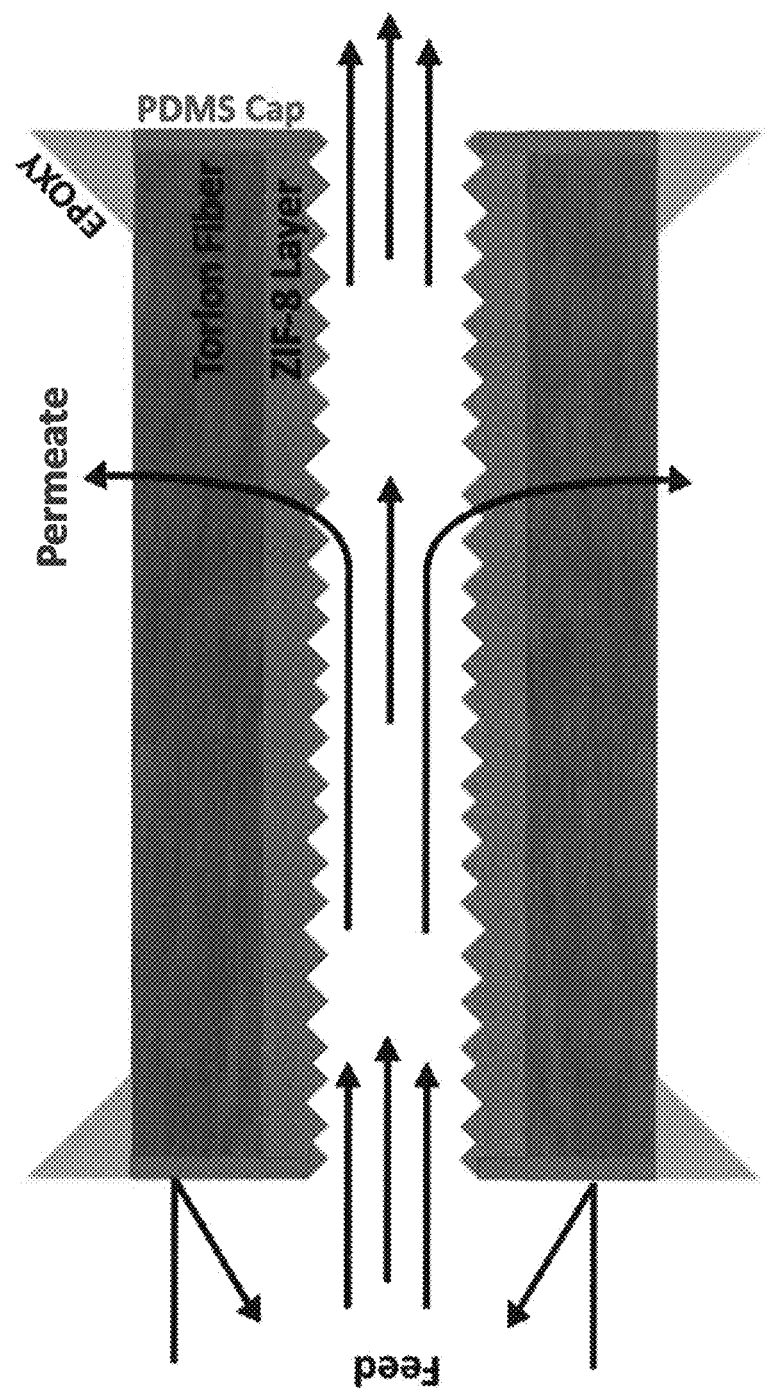
FIG. 24B illustrates a schematic showing suppression of the bypass effect in FIG. 24A by capping the hollow fiber ends with a PDMS film.
Figures 25A, 25B:
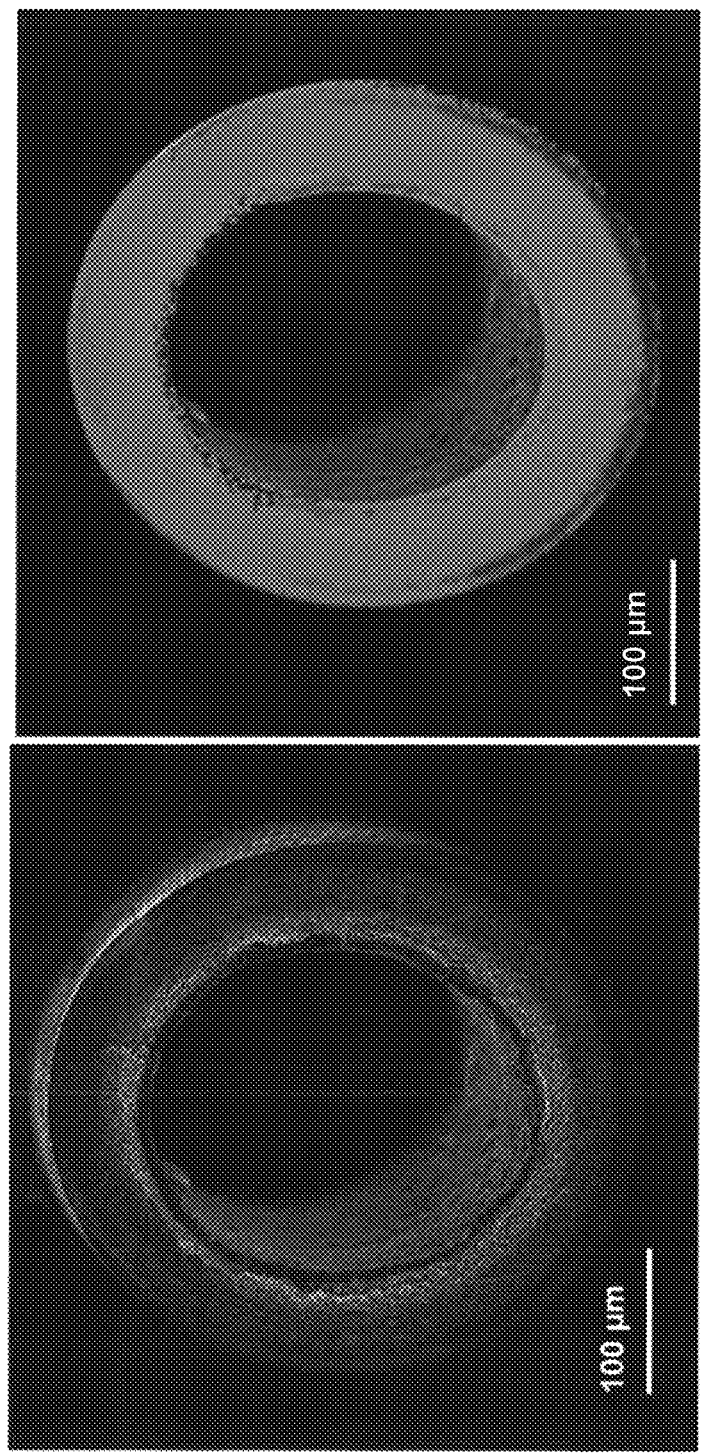
FIG. 25A illustrates a SEM cross-section image of the inner-surface ZIF-8 membrane after end-capping by penetration of PDMS.
FIG. 25B illustrates an EDS elemental map of Si (red) showing the penetration of PDMS into the pores of a polyamide-imide (e.g., TORLON®) hollow fiber.

To suppress this membrane bypass, the inventors include a capping step to the IMMP approach, accomplished by applying a controlled amount of a solution containing poly(dimethylsiloxane) (PDMS) to the ends of the mounted hollow fibers 100. See FIG. 24B. The PDMS solution is readily absorbed by capillary action into the hollow fiber 100, and blocks the pores of the hollow fiber 100 support. See FIGS. 25A and 25B. SEM cross-sectional imaging (see FIG. 25A) and EDX mapping (see FIG. 25B) indicated that the fiber matrix is completely covered by PDMS while the bore remains unblocked. Since the permeances of the feed gases through PDMS are 3 orders of magnitude lower than through the macroporous hollow fiber 100 support, the $C_3H_8$ flux should decrease substantially after capping. After curing the PDMS-sealed hollow fibers 100, the $H_2/C_3H_8$ separation factor is now much higher (370 at 120° C.) (see FIG. 21A) and the $C_3H_6/C_3H_8$ separation factor is also higher (12 at 25° C.) (see FIG. 21B), consistent with previously reported ZIF-8 membranes with low defect densities.[8, 17-20] Notably, the $C_3H_8$ permeance decreased by a factor of 10 after capping. This indicates that most of the propane was previously bypassing the ZIF-8 layer and that the addition of the capping step to the IMMP largely shuts down this non-selective permeation path. The permeate stream contains 92% $C_3H_6$/8% $C_3H_8$, which is a significant upgrade from the equimolar feed stream.

Performance of Bundle of ZIF-8 Membranes Made Using IMMP Reactor Cell/Module

In large-scale gas separations with hollow fiber membranes, high membrane areas per unit module volume are achieved by bundling large numbers of fibers in the permeation module. The present invention has the advantage of being inherently a modular approach that should allow independent processing of membranes in each fiber constituting a bundle.

To demonstrate this concept, the inventors applied reactor module 400 to the simultaneous processing of three polyamide-imide (e.g., TORLON®) hollow fiber 100 supports. The processing conditions were identical to the case of the single-fiber membranes, except that the total feed solution initially introduced to the bore and the flow rate on the bore side was increased by a factor of 3 so that the flow rate through individual hollow fibers 100 was maintained constant in relation to the single-fiber membrane fabrication described earlier. The ends of the hollow fibers 100 were capped in a similar manner as described earlier.

Figure 23A:
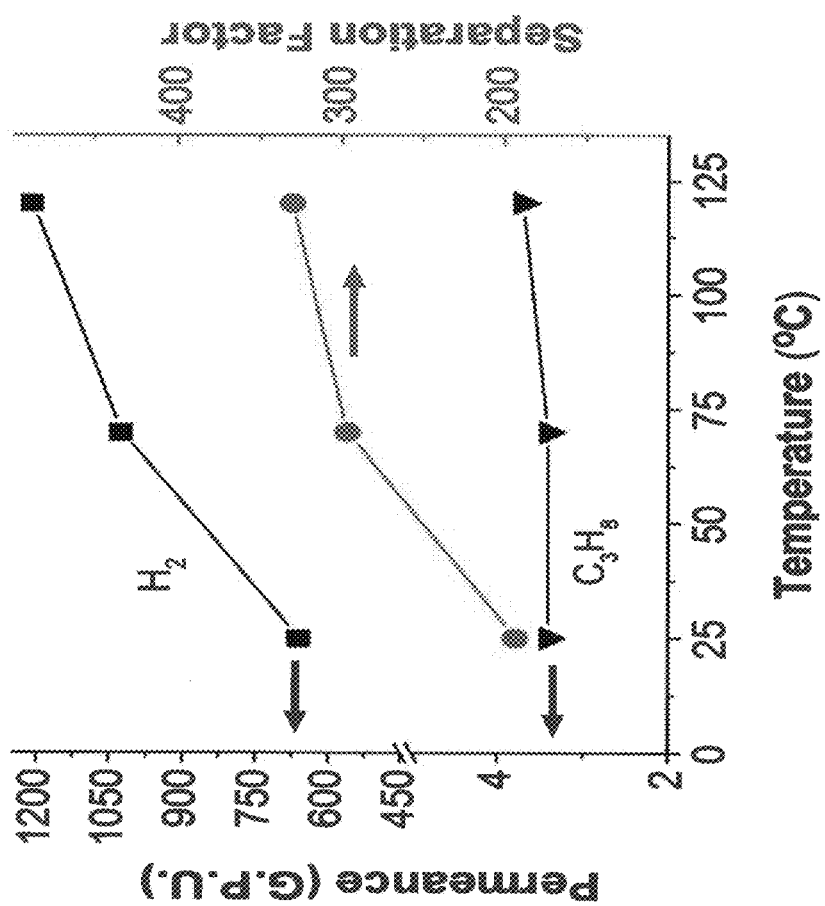
FIG. 23A illustrates a chart of Temperature (° C.) v. Permeance (G.P.U.) and Separation Factor, showing binary permeation characteristics for an equimolar $H_2/C_3H_8$ feed mixture on ZIF-8 membranes grown simultaneously in three (3) polyamide-imide (e.g., TORLON®) hollow fiber using the IMMP system and sealing the ends of the fibers with PDMS.
Figure 23B:
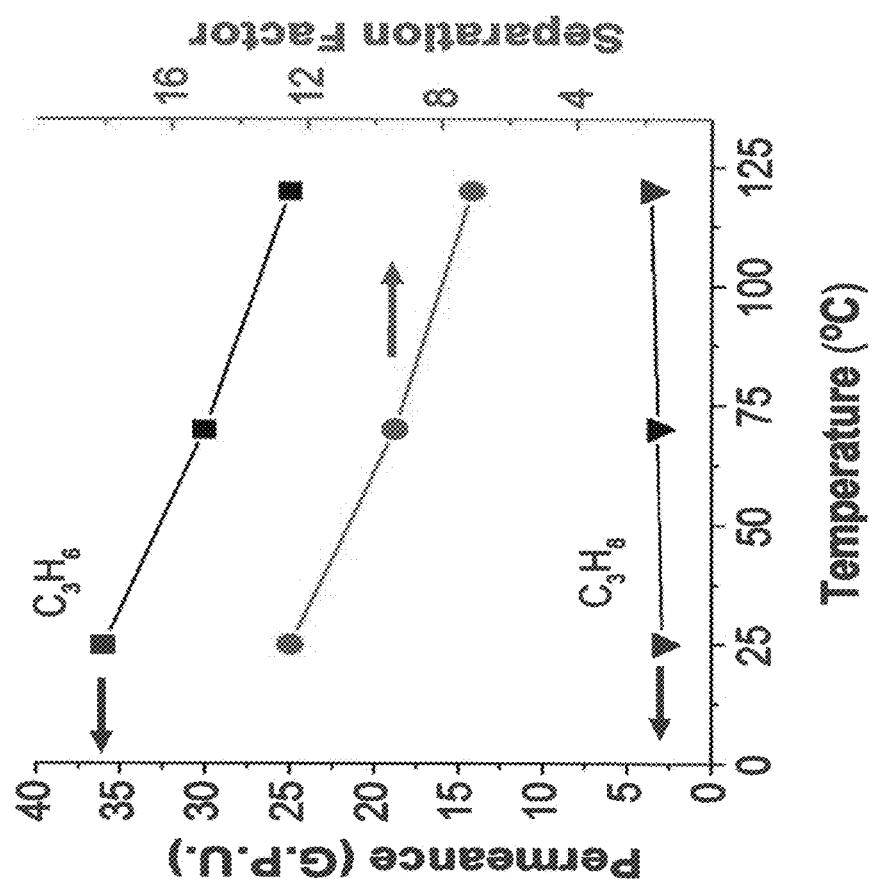
FIG. 23B illustrates a chart of Temperature (° C.) v. Permeance (G.P.U.) and Separation Factor, showing binary permeation characteristics for an equimolar $C_3H_6/C_3H_8$ feed mixture on ZIF-8 membranes grown simultaneously in three (3) polyamide-imide (e.g., TORLON®) hollow fiber using the IMMP approach and sealing the ends of the fibers with PDMS.

FIGS. 23A and 23B show that the $H_2/C_3H_8$ and $C_3H_6/C_3H_8$ separation behavior is near-identical to the single-fiber membranes (see FIGS. 21A and 21B), thereby clearly demonstrating the potential for scalability of the IMMP approach. The inventors also note that the separation factor values of the ZIF-8 membranes are very sensitive to the small permeance of $C_3H_8$ (~2.5 G.P.U. in the present invention). With further improvements in the capping methods (e.g., using less permeable polymers than PDMS) and optimization of the ZIF-8 membrane growth conditions, the small $C_3H_8$ permeance can be further reduced and the separation factor further increased, leading to a highly attractive membrane platform for hydrocarbon separations. Given the overall importance of tunable ZIF materials for a range of hydrocarbon separations, the membrane processing approach reported here overcomes many of the limitations of current processes and moves significantly towards realizing scalable molecular sieving MOF membranes.

Improved Membrane Synthesis Using IMMP Reactor Cell/Module

Using a macroporous polyamide (e.g., TORLON®) hollow fiber and the material ZIF-8 as an archetype for hollow fiber and tubular membrane synthesis, a series of isothermal and initial heating membrane synthesis experiments were performed. Several examples of ZIF-8 membrane fabrication using this reactor module 400 are described below, and their results are shown in SEM micrographs of FIGS. 27A-27F, 30C and 31A-31C.

Figures 26A, 26B:
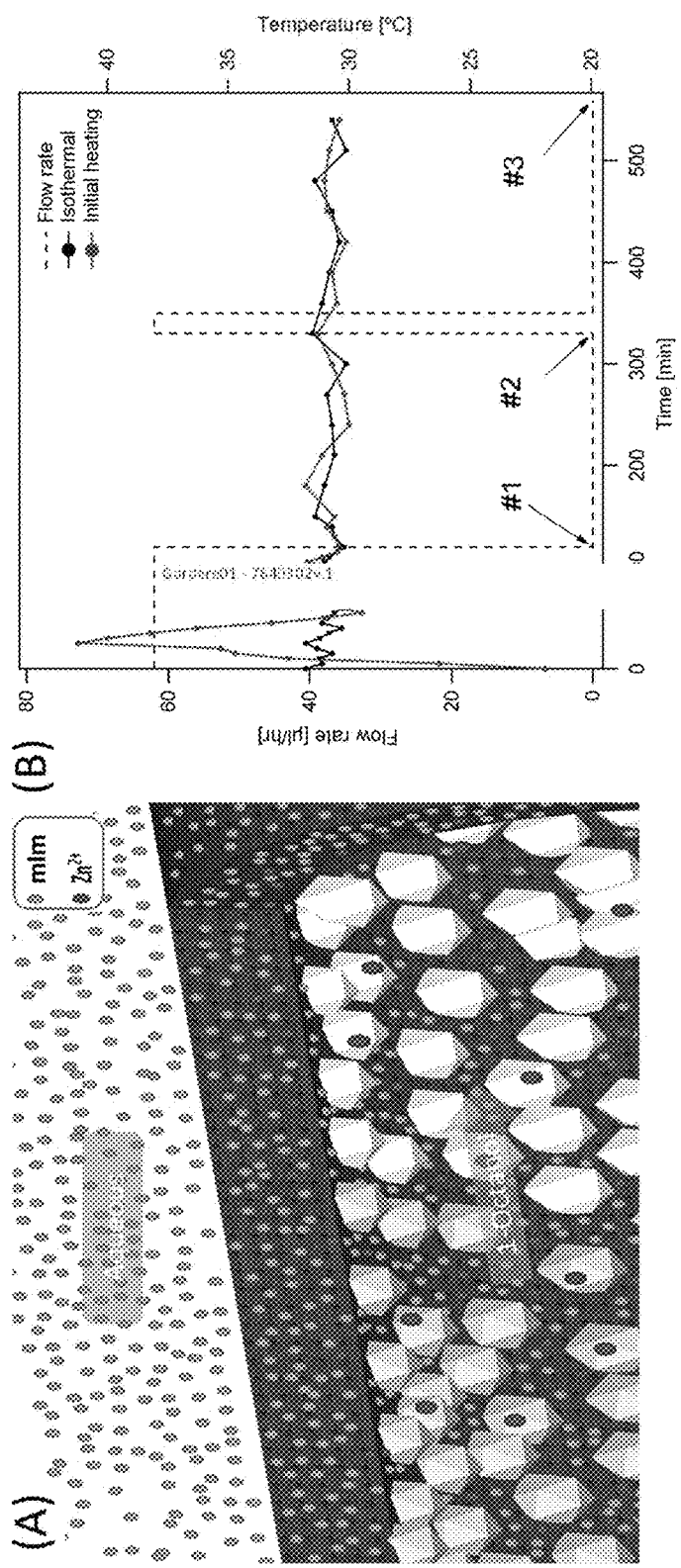
FIG. 26A illustrates a schematic of the Interfacial Microfluidic Membrane Processing (IMMP) approach, showing two feed streams for a ZIF-8 membrane on a polyamide-imide (e.g., TORLON®) hollow fiber.
FIG. 26B illustrates a chart of Time vs. Flow rate (µl/hr) and Temperature (° C.), showing bore flow rate and two different temperature profiles (isothermal and initial heating) for the IMMP approach to synthesize ZIF-8 membranes on an inner surface of polyamide imide (e.g., TORLON®) hollow fibers with the numbered temporal locations (#1, #2, and #3) indicating the times where the ZIF-8 membrane growth were arrested.
Figures 27D, 27E, 27F:
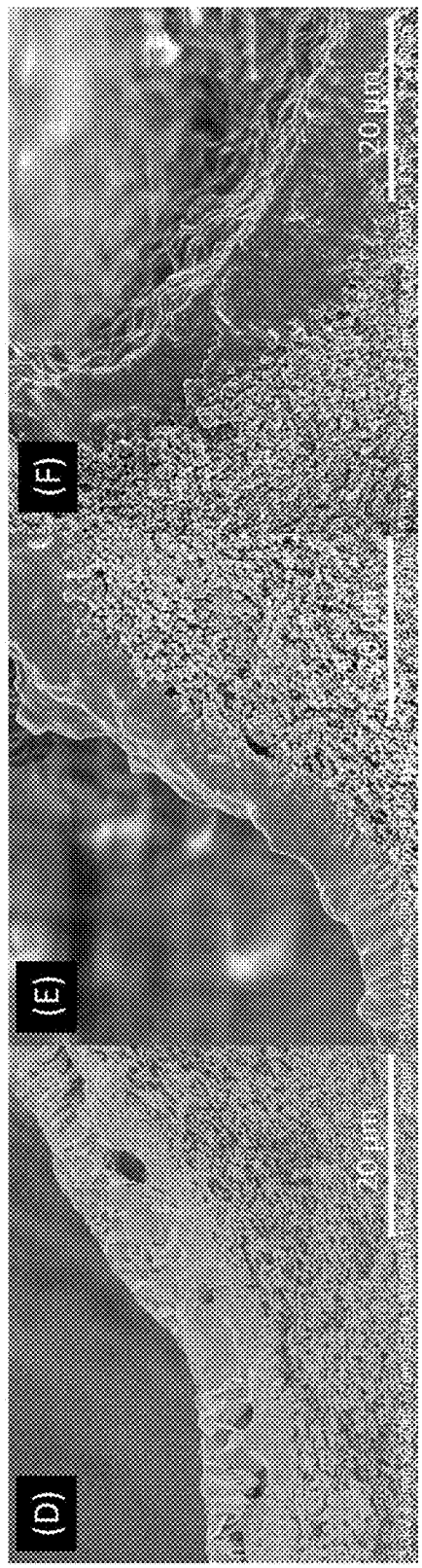
FIG. 27D illustrates an exemplary cross-sectional SEM image of a ZIF-8 membrane grown on a polyamide-imide (e.g., TORLON®) hollow fiber after 2 hours of continuous membrane growth (Step 1 using initial heating IMMP approach.
FIG. 27E illustrates an exemplary cross-sectional SEM image of a ZIF-8 membrane grown on a polyamide-imide (e.g., TORLON®) hollow fiber after 2 hours of continuous membrane growth (Step 1) and 3.5 hours of static membrane growth (Step 2) using initial heating IMMP approach.
FIG. 27F illustrates an exemplary cross-sectional SEM image of a ZIF-8 membrane grown on a polyamide-imide (e.g., TORLON®) hollow fiber after 2 hours of continuous membrane growth (Step 1), 3.5 hours of static membrane growth (Step 2) and 20 minutes of second continuous membrane growth followed by 3.5 hours of second static membrane growth (Step 3) using initial heating IMMP approach.

FIG. 26A shows a schematic of the IMMP reactor module 400 for ZIF-8 membrane fabrication on the inner bore side surface 110 of the polyamide imide (e.g., TORLON®) hollow fibers. The formation of a ZIF-8 membrane is achieved by contacting the two reactant streams (i.e., $Zn^{2+}$ ions dissolved in 1-octanol on the inner bore side surface 110, and 2-methylimidazole (mIm) dissolved in deionized water (DI) on the outer (shell) side surface 105) across the polyamide-imide (e.g., TORLON®) hollow fiber support. In these experiments, the two solvents are chosen to be immiscible, thereby allowing a sharp interface between the two phases. The use of a large excess of mIm (e.g., mIm/$Zn^{+2}$ concentration ratio=75) allows the $Zn^{2+}$ to act as a limiting reactant, thereby leading to ZIF-8 film formation on the inner surface.

The temporal flow profile in the bore side is shown in FIG. 26B. It comprises four steps: about 120 minutes of membrane formation under a continuous flow of about 62 µL/hour of a $Zn^{2\pm}$/octanol solution (Step 1), about 210 minutes of membrane growth under static conditions (Step 2), about 20 minutes of $Zn^{2\pm}$/octanol solution replenishment at a continuous flow of about 62 µL/hour (Step 3), and a final 210 minutes of static membrane growth (Step 4).

Two different temperature profiles are also shown in FIG. 26B, as discussed further below. They comprise an isothermal profile (e.g., about 30° C.) and an initial heating profile (e.g., increased linearly from about 22° C. to about 42° C. in about 25 minutes and decreased from 42° C. to 30° C. in about 60 minutes), as discussed further below.

Membrane Formation Process Using IMMP Reactor Module/Cell

To investigate the membrane formation process, the inventors repeated the IMMP approach multiple times and arrested the ZIF-8 membrane growth at three different points as indicated by the numbered temporal locations (i.e., arrest points #1, #2 and #3) in FIG. 26B.

Starting with a polyamide-imide (e.g., TORLON®) hollow fiber mounted in the IMMP reactor module 400,[12] a $Zn^{+2}$/1-octanol solution containing about 0.22 g Zinc nitrate hexahydrate ($Zn^{+2}$) in about 40 mL 1-octanol (about 0.018 mol/L) was flowed through the bore 110 of the hollow fiber 100 while an aqueous mIm solution containing about 9 g of mIm in about 80 mL deionized water (DI) (about 1.37 mol/L) was poured into the reactor chamber 345 immersing the outer (shell) side surface 105 of the hollow fiber 100 while stirring the solution at about 60 rpm for about 120 minutes to provide a continuous membrane growth step.

The temperature of the reactor module 400 was maintained at about 31.0±0.5° C. throughout the IMMP process. See FIG. 26B.

For each arrest point #1, #2 and #3, about 10 mL of neat 1-octanol was pushed through the bore side 110 of the hollow fiber 100 while exchanging the shell side 105 solution with about 70 mL neat methanol (MeOH) and replaced three times.

After the 120 minutes of continuous membrane growth step (arrest point #1), the flow rate of the $Zn^{+2}$/1-octanol solution through the bore 110 of the hollow fiber 100 was stopped for about 210 minutes to provide a static membrane growth step.

After the 210 minutes of static membrane growth step (arrest point #2), the flow rate of the $Zn^{+2}$/1-octanol solution through the bore 110 of the hollow fiber 100 was continued for about 20 minutes to provide a second continuous membrane growth step.

After the 20 minutes of second continuous membrane growth step, the flow rate of about 0.6 mL/hour through the bore 110 of the hollow fiber 100 was stopped for about 210 minutes to provide a second static membrane growth step.

After the 210 minutes of second static membrane growth step (arrest point #3), the reaction was stopped.

To stop the reaction, about 10 mL of neat 1-octanol solvent was pushed through the bore 110 while the outer (shell) side surface 105 was soaked in about 70 mL of neat DI (and replaced three times) to remove the excess $Zn^{+2}$. Next, about 10 mL heptanes were pushed through the bore 110 while the outer (shell) side surface 105 was soaked in about 70 mL heptanes to remove the 1-octanol. Next, similar procedure was performed with a more volatile hexane solution. Then, about 10 mL hexane was pushed through the bore 110 while outer (shell) side surface 105 was soaked in about 70 mL hexane to remove the heptanes. Finally, about 20 mL of MeOH was pushed through the bore 110 while the outer (shell) side surface 105 was soaked in about 70 mL methanol to remove the DI. The membrane was dried at about room temperature (e.g., about 25° C.) for about 2 days.

Binary propylene ($C_3H_6$)/propane ($C_3H_8$) permeation measurements were conducted in situ for each arrest point #1, #2 and #3, and, finally, after completion of the IMMP process, the ZIF-8 membrane on the polyamide-imide (e.g., TORLON®) hollow fiber 100 was removed from the IMMP reactor module 400 and cross-sectioned for SEM imaging and thickness measurements, as discussed below.

FIGS. 27A-27C show the development of the ZIF-8 membrane morphology at the three different arrest points #1, #2 and #3 shown in FIG. 26B. Tables 6 & 7 show information about average thickness and $C_3H_6/C_3H_8$ permeation characteristics for each of these arrest points.

Figure 28:
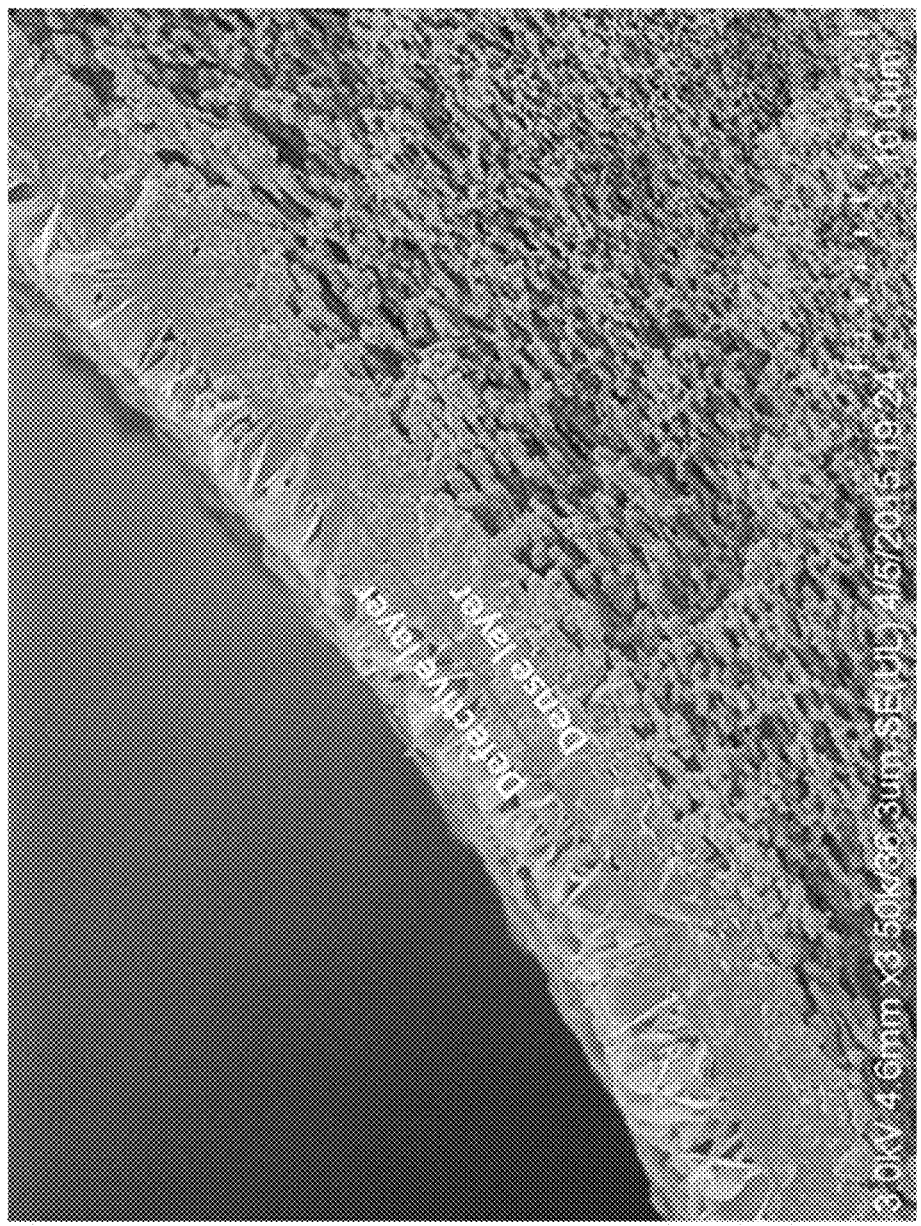
FIG. 28 illustrates a magnified SEM image of dense and defective ZIF-8 membrane layers grown on a polyamide-imide (e.g., TORLON®) hollow fiber after 120 minutes of continuous membrane growth using isothermal IMMP approach.

After the 120 minutes of the continuous membrane growth step (arrest point #1), a dual-layer ZIF-8 membrane may be observed on the inner bore surface 110 of the hollow fiber 100 (see FIGS. 27A & 28) with an overall thickness of about 7 μm (see Table 6), of which about 4.5 μm is a dense ZIF-8 membrane layer and the remainder is a discontinuous membrane layer composed of plate-like structures.

Without wishing to be bound to any theory, the inventors believe this morphology arises from the rapid penetration of mIm (which is soluble in both water and octanol) into the octanol phase. At the inner surface of the fiber, mIm may be rapidly consumed by reaction with $Zn^{2+}$ to form a dense ZIF-8 membrane layer. However, the formation of this initial dense layer may act as a barrier that restricts the availabilty of mIm species further into the octanol phase, leading to the diffusion-limited formation of a second discontinuous film morphology on top of the dense layer (see FIGS. 29A-29B).

Figure 29:
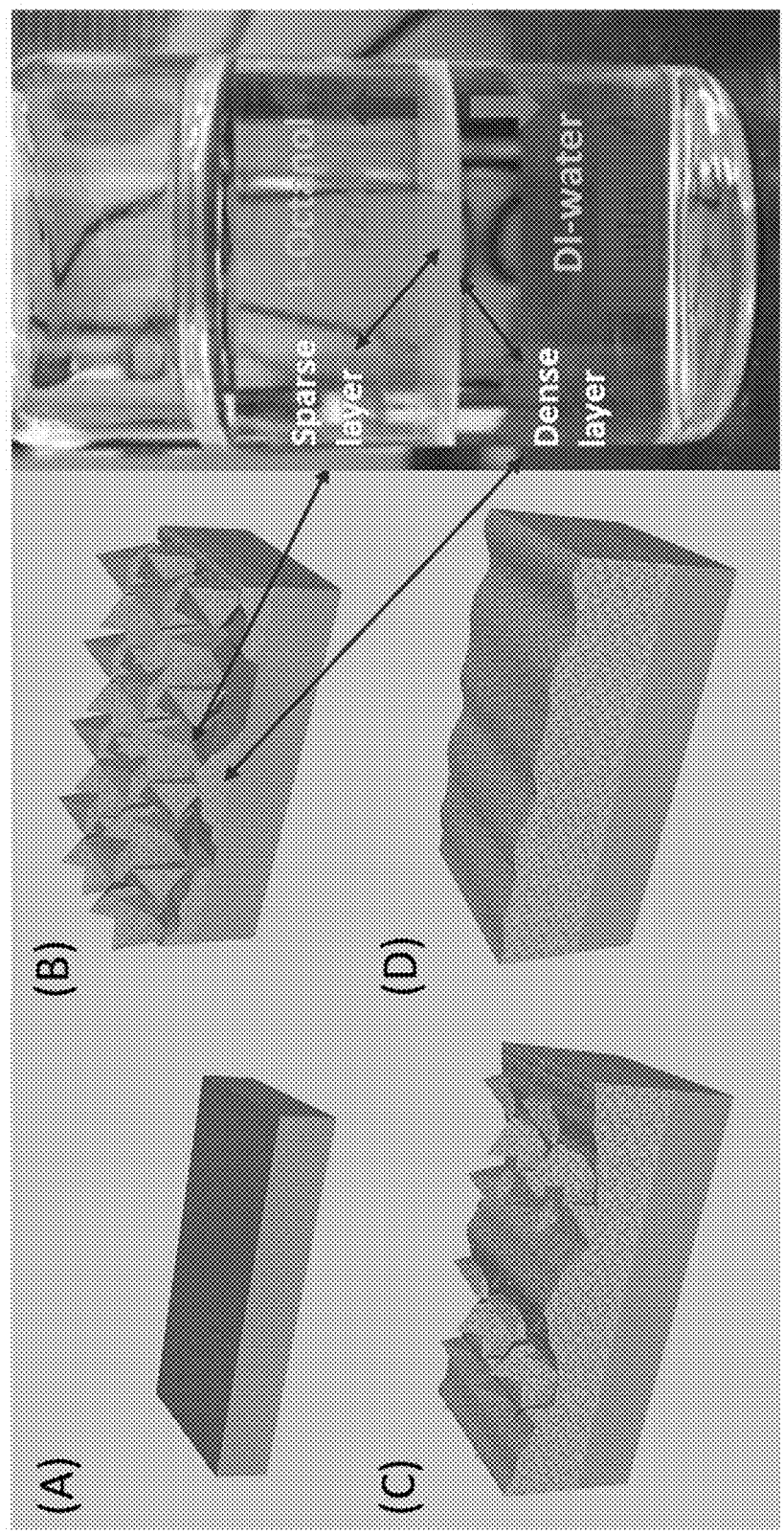
FIG. 29 illustrates a schematic of the ZIF-8 membrane growth mechanism on polyamide-imide (e.g., TORLON®) hollow fibers: (A) depicts a side perspective view of a hollow fiber (tan) at 0 hours and (B) depicts a side perspective view of a ZIF-8 membrane (gray) grown on the hollow fiber (tan) during synthesis after 2 hours of continuous membrane growth (Step 1), (C) depicts a side perspective view of the ZIF-8 membrane (gray) grown on the hollow fiber (tan) during synthesis after 2 hours of continuous membrane growth (Step 1) and 3.5 hours of static membrane growth (Step 2), (D) depicts a side perspective view of the ZIF-8 membrane (gray) grown on the hollow fiber (tan) during synthesis after 2 hours of continuous membrane growth (Step 1), 3.5 hours of static membrane growth (Step 2) and 20 minutes of second continuous membrane growth followed by a final 3.5 hours of second static membrane growth (Step 3); and a (E) depicts a photograph of the two reactants (i.e., zinc nitrite hexahydride and mIm) in the two solvents (i.e., DI and 1-octanol) after 15 minutes of interfacial contact in a glass vial.

Since this effect is difficult to observe directly inside the hollow fiber 100, the inventors performed a similar experiment by contacting the two phases in a transparent glass vial (see FIG. 29E). As shown in FIG. 29E, a dense membrane layer forms at the DI/1-octanol interface and a cloudy layer with sparse crystallization forms further into the 1-octanol phase. Further, the dense membrane layer has nanoscopic defects which lead to high permeances of both propylene ($C_3H_6$) and propane ($C_3H_8$) (about 31 G.P.U. and 11 G.P.U., respectively) and a low propylene selectivity (about 2.8). The initial continuous growth step of the IMMP approach does not yield a viable ZIF-8 membrane, and, therefore, further IMMP processing is required.

After 210 minutes of the static membrane growth step (arrest point #2) during which there was no continuous replenishment of the limiting reactant $Zn^{2+}$, a single layer ZIF-8 membrane on the inner bore surface 110 of the hollow fiber 100 was observed with an overall thickness of about 10 μm (see Table 6). The overall ZIF-8 membrane growth rate during the static membrane growth step is much lower than during the initial continuous membrane growth step due to limited availability of $Zn^{2+}$ as well as slow diffusion of mIm through defects in the dense layer. FIG. 27B reveals that the dual-layer morphology is replaced with a single dense membrane layer during the static membrane growth step. The discontinuous membrane layer is gradually densified by slow addition of crystallized material as depicted in FIG. 29C. The information in Table 7 shows a decrease in permeance for both $C_3H_6$ and $C_3H_8$ (about 26 G.P.U. and about 1.8 G.P.U., respectively) and an increase in propylene ($C_3H_6$) selectivity (about 14.3), indicating that nanoscopic defects are being filled in with ZIF-8 material and that the static membrane growth step is important for defect control.

After the 20 minutes of the second continuous membrane growth step followed by 210 minutes of the second static membrane growth step (arrest point #3), a single, continuous layer ZIF-8 membrane on the inner bore surface 110 of the hollow fiber 100 was observed with an overall thickness of about 12 μm (see Table 6). FIGS. 27C & 29D reveal that the single membrane layer is further densified to a continuous membrane layer during the second static membrane growth and second static membrane growth steps. The information in Table 7 shows a further decrease in permeance for both $C_3H_6$ and $C_3H_8$ (about 23 G.P.U. and about 1.3 G.P.U., respectively) (i.e., 1 G.P.U.=$3.348 \times 10^{-10}$ molm$^{-2}$ s$^{-1}$ Pa$^{-1}$) and a further increase in $C_3H_6$ selectivity (about 17).

TABLE 6

Measurement of an average thickness for In-Situ grown ZIF-8 Membrane after each Interfacial Microfluidic Membrane Processing (IMMP) process step.

| Processing Method | Average Thickness (μm) After Step 1 (Arrest Point #1) | | Average Thickness (μm) After Step 2 (Arrest Point #2) | | Average Thickness (μm) After Step 3 (Arrest Point #3) | |
|---|---|---|---|---|---|---|
| | Dense | Discontinuous | Dense | Discontinuous | Dense | Discontinuous |
| Isothermal | 4.5 ± 0.5 | 2.7 ± 0.4 | 10.2 ± 2.1 | N/A | 12.3 ± 1.6 | N/A |
| Initial Heating | 2.5 ± 0.6 | 3.2 ± 0.9 | 7.0 ± 1.2 | N/A | 8.0 ± 2.3 | N/A |

TABLE 7

Measurement of Gas Permeation Properties of In-Situ grown ZIF-8 membrane after each IMMP process step in binary $C_3H_6/C_3H_8$ with an equimolar feed mixture.

| Processing Method | After Step 1 (Arrest Point #1) | | | After Step 2 (Arrest Point #2) | | | After Step 3 (After Arrest Point #3) | | |
|---|---|---|---|---|---|---|---|---|---|
| | Permeance (G.P.U.) | | Selectivity | Permeance (G.P.U.) | | Selectivity | Permeance (G.P.U.) | | Selectivity |
| | $C_3H_6$ | $C_3H_8$ | $C_3H_6/C_3H_8$ | $C_3H_6$ | $C_3H_8$ | $C_3H_6/C_3H_8$ | $C_3H_6$ | $C_3H_8$ | $C_3H_6/C_3H_8$ |
| Isothermal | 31 | 11 | 2.8 | 26 | 1.8 | 14.3 | 23 | 1.3 | 17.7 |
| Initial Heating | 45 | 14 | 3.2 | 30 | 2.5 | 12 | 33 | 1.9 | 17.5 |

Role of Polyamide-Imide (e.g., TORLON®) Hollow Fiber

Further, the inventors confirmed that all permeation measurements are reliably measuring the intrinsic properties of the ZIF-8 membranes with negligible effects of polyamide-imide (e.g., TORLON®) hollow fiber support in determining the defect density and selectivity of the membrane. The fabricated polyamide-imide (e.g., TORLON®) hollow fibers have an outer diameter (OD) of about 300 μm and an inner diameter (ID) of about 200 μm, as discussed below.

For scanning probe microscopy (SPM) of the hollow fiber support surfaces, the hollow fibers were immersed in hexane followed by immersion of the saturated fibers in liquid nitrogen. Then, the hollow fibers were gently broken into several pieces, which were then transferred to a silicon wafer for the SPM surface roughness measurements. The RMS surface roughness was obtained by averaging data from several 2 μm×2 μm area images. The RMS roughness was measured as 63±5 nm, which is much smaller than the ZIF-8 membrane thickness and is not expected to lead to large heterogeneities in the film thickness (see Table 6).

Figures 30A, 30B:
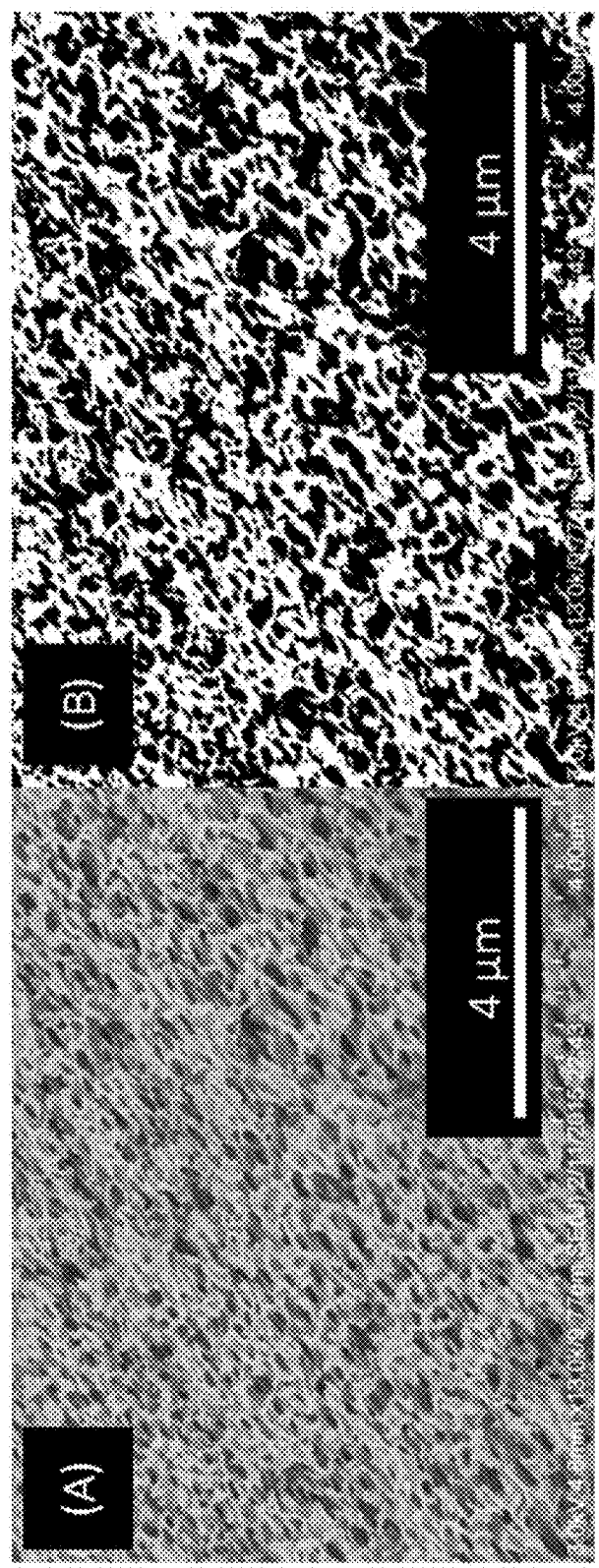
FIG. 30A illustrates a cross-sectional SEM image of a polyamide imide (e.g., TORLON®) hollow fiber.
FIG. 30B illustrates an associated binary image for estimation of porosity of the image in FIG. 30A.
Figures 30C, 30D:
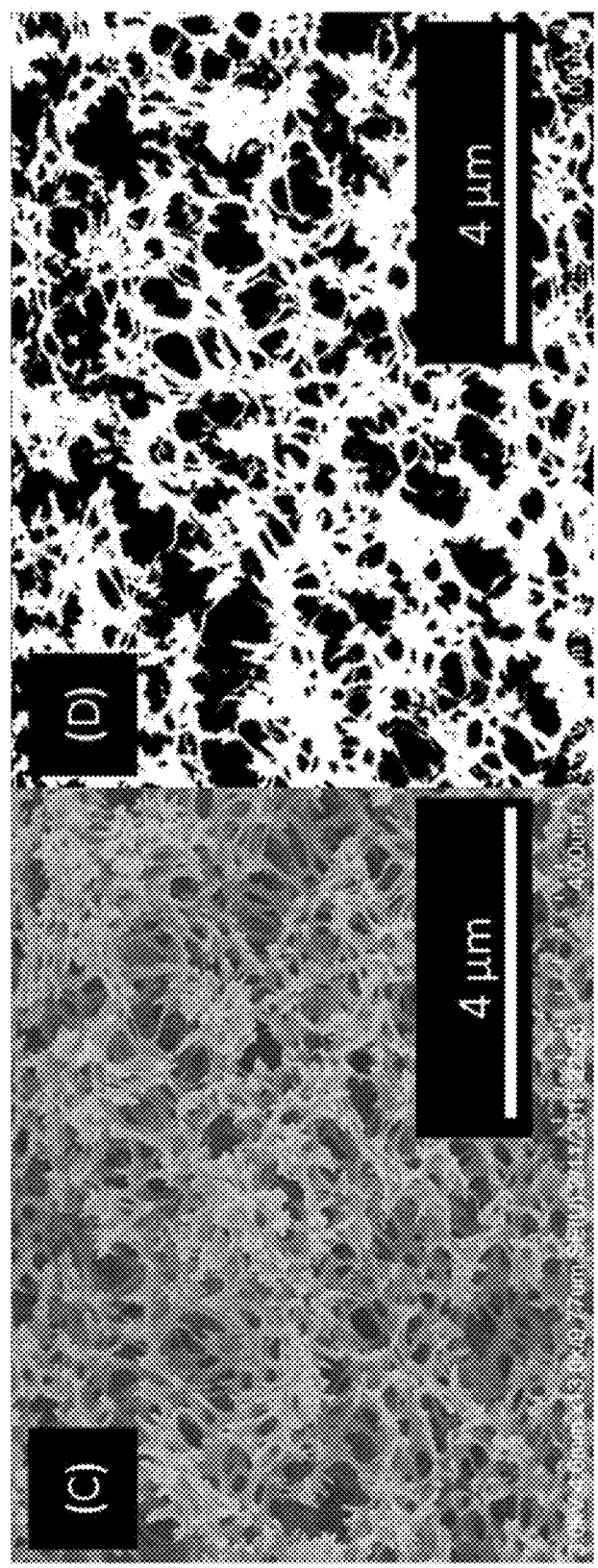
FIG. 30C illustrates a cross-sectional SEM image of a modified polyamide imide (e.g., TORLON®) hollow fiber.
FIG. 30D illustrates an associated binary images for estimation of the porosity of the image in FIG. 30C.

The inventors also characterized the porosity of the hollow fibers from SEM images using the Khare and Burris method.[21] For this purpose (see FIGS. 30A-30B), binary images were obtained from cross-sectional SEM images of the support via the image analysis program ImageJ.[22] The porosity (c) and average pore size of the fibers were estimated at 44% and 290 nm, respectively.

The hollow fibers are also highly permeable, as characterized by their $N_2$ permeance of 54000 G.P.U. and permeability of $2.7 \times 10^6$ Barrer (i.e., 1 Barrer=1 G.P.U. μm) at 25° C.

Without wishing to be bound to any theory, the inventors believe that hollow fibers with larger porosity and somewhat larger pore size may allow faster formation of a thin ZIF-8 membrane layer and better anchoring of this membrane layer to the fiber surface.

Negligible Effects of External Mass Transfer Resistances

Further, the inventors confirmed that all permeation measurements are reliably measuring the intrinsic properties of the ZIF-8 membranes with negligible effects of external mass transfer resistances. The total permeation resistance ($R_{Total}$) through the membrane was modeled as a result of three series resistances: membrane layer ($R_{membrane}$), support ($R_{Torlon}$), and external ($R_{external}$). To quantify the contributions of the support+external mass transport resistances to the total resistance through the membrane, the inventors obtained single-component gas permeation data through a bare polyamide-imide (e.g., TORLON®) hollow fiber at 25° C.

For an accurate estimate from a bare polyamide-imide (e.g., TORLON®) hollow fiber that has been exposed to actual IMMP process conditions, the inventors performed IMMP approach on the bare hollow fiber 100 with only the aqueous mIm solution and no $Zn^{+2}$ metal source in the 1-octanol solution (to prevent ZIF-8 formation).

Using the measured bare hollow fiber permeances along with the permeances from the ZIF-8 membrane (Case 1), Equations 1 & 2 were used to back-calculate the value of $R_{Torlon}+R_{external}$ and, therefore, determine the corrected values of $R_{membrane}$ and $P_{membrane}$ (G.P.U.) as shown in Table 8. External and support resistances lead to only a correction of 0.01-5% in the permeance measurements for the three gases, which is negligible.

$$R_{membrnae} = \frac{1}{P_{membrane}} \quad (1)$$

$$R_{Total} = R_{membrane} + R_{Torlon+external} \quad (2)$$

TABLE 8

Single gas permeance results before and after considering the effect of polyamide-imide (e.g., TORLON ®) hollow fiber and external mass transfer resistances at 25° C.

| Gas | Measured Permeance (G.P.U.) | Corrected Permeance (G.P.U.) | Error |
|---|---|---|---|
| Propane ($C_3H_8$) | 1.0 | 1.0 | 0.01% |
| Propylene ($C_3H_6$) | 66.5 | 66.8 | 0.5% |
| Hydrogen ($H_2$) | 1537 | 1596 | 3.7% |

Fabrication of Polyamide-Imide (e.g., TORLON®) Hollow Fiber Supports

Polyamide imide (e.g., TORLON®) hollow fibers of outer diameter (OD) of about 300 µm and inner diameter (ID) of about 200 µm were produced by a spinning method. The polymer dope compositions and spinning conditions are shown in Table 9.

TABLE 9

Spinning conditions of polyamide imide (e.g., TORLON ®) hollow fiber porous support.

| | |
|---|---|
| Dope composition (PAI/LiNO$_3$/NMP/ethanol) (wt %) | 15/15/66/4 |
| Dope flow rate (ml/hr) | 360 |
| Bore fluid (NMP/H$_2$O) (wt %) | 80/20 |
| Bore fluid flow rate (ml/hr) | 120 |
| Air gap (cm) | 16 |
| Take up rate (m/min) | 45 |
| Operating temperature (° C.) | 25 |
| Quench bath temperature (° C.) | 25 |

A polyamide-imide (e.g., TORLON®) core dope was fed to the spinneret compartment. The extruded polymer dope passed through an air-gap and into a water quench bath (primary coagulant) where the fiber phases separate. A standard bore fluid used in this experiment comprised a non-volatile solvent (NMP) and deionized water (DI) with the weight ratio of 80:20.

Then, the fiber was passed over a TEFLON® guide and collected on a rotating take-up drum partially submerged in a second water bath, which was continuously replenished with fresh water.

Next, fibers spun under identical conditions were removed from the take-up drum, tied loosely and soaked in DI for about 4 days at room temperature (i.e., about 25° C.) with fresh DI added daily to remove any residual NMP and promote complete removal of the water-soluble LiNO$_3$.

Then, the water in the hollow fiber was exchanged with a solvent by immersion for about 1 hour each in three batches of fresh methanol (to remove excess water) and then about 1 hour each in three batches of fresh hexane (to remove excess methanol).

After about 2 hours air drying step, the hollow fibers were dried at about 130° C. for about 24 hours to completely remove any residual NMP.

The hollow fibers had an RMS roughness of 63±5 nm, which is much smaller than the ZIF-8 membrane thickness and is not expected to lead to large heterogeneities in the film thickness (see Table 6). Further, the porosity and average pore size of the hollow fibers were estimated at 44% and 290 nm, respectively (see FIGS. 30A-30B).

Fabrication of Improved Polyamide Imide (e.g., TORLON®) Hollow Fiber Supports

The improved polyamide imide (e.g., TORLON®) hollow fibers of outer diamer (OD) of about 360 µm and inner diameter (ID) of about 270 µm and enhanced porosity were fabricated by a modified spinning approach. The modified polymer dope compositions and spinning conditions are shown in Table 10.

TABLE 10

Modified spinning conditions of polyamide imide (e.g., TORLON ®) hollow fiber porous support.

| | |
|---|---|
| Dope composition (PAI/LiNO$_3$/NMP/ethanol) (wt %) | 15/15/66/4 |
| Dope flow rate (ml/hr) | 300 |
| Bore fluid (NMP/H$_2$O) (wt %) | 85/15 |
| Bore fluid flow rate (ml/hr) | 100 |
| Air gap (cm) | 15 |
| Take up rate (m/min) | 40 |
| Operating temperature (° C.) | 27 |
| Quench bath temperature (° C.) | 25 |

Non-volatile solvent (NMP), non-solvent (water) and pore formers (LiNO$_3$) in the dope composition, quench bath temperatures (i.e., about 25° C.), take-up rate (i.e., about 40 m/minute) and air gap height (i.e., about 15 cm) were applied in order to identify a robust process to produce improved hollow fibers with engineered surface porosity. The key parameters control the morphology of the improved hollow fibers include composition of the polymer dope, composition of the bore liquid, height of the air gap and spinning speed.

A polyamide-imide (e.g., TORLON®) core dope was fed to the spinneret compartment. The extruded polymer dope passed through an air-gap and into a water quench bath (primary coagulant) where the fiber phases separate. To increase the porosity of the hollow fibers, a bore fluid used in this experiment comprised NMP and deionized water (DI) with the weight ratio of 85:15 (instead of 80:20).

Then, the fiber was passed over a TEFLON® guide and collected on a rotating take-up drum partially submerged in a second water bath, which was continuously replenished with fresh water.

Next, fibers spun under identical conditions were removed from the take-up drum, tied loosely and soaked in DI for about 5 days at room temperature (i.e., about 25° C.) with fresh DI added daily to remove any residual NMP and promote complete removal of the water-soluble LiNO$_3$.

Then, the water in the hollow fiber was exchanged with a solvent by immersion for about 1 hour each in three batches of fresh methanol (to remove excess water) and then about 1 hour each in three batches of fresh hexane (to remove excess methanol).

After about 2 hours air drying step, the hollow fibers were dried at about 130° C. for about 24 hours to completely remove any residual NMP.

The resulting hollow fibers had an RMS roughness of 62±6 nm which is similar to the previous hollow fibers (discussed above) and, thus, provides a flat surface for ZIF-8 membrane layer formation. However, the porosity and average pore size of the improved hollow fibers were much larger at 55% and 480 nm, respectively (see FIGS. 30C-30D).

Improved Membrane Synthesis

To investigate the effect of modified hollow fibers in conjunction with a modified IMMP approach, the inventors prepared ZIF-8 membranes in three different ways: Case 1 uses a fabricated polyamide-imide (e.g., TORLON®) hollow fiber and an isothermal IMMP approach; Case 2 uses an improved polyamide-imide (e.g., TORLON®) hollow fiber prepared using a modified spinning technique and a modified initial heating IMMP approach; and Case 3 uses the improved polyamide-imide (e.g., TORLON®) hollow fiber and the modified initial heating IMMP approach.

Performance in Membrane Synthesis Using IMMP Reactor Cell/Module: Isothermal Temperatures Starting with a fabricated polyamide-imide (e.g., TORLON®) hollow fiber mounted in the IMMP reactor module 400,[12] about 10 mL of neat 1-octanol was flowed at about 2 mL/min through a bore 110 of a hollow fiber 100 using a syringe pump. Then, about 3 mL of a Zn+2/1-octanol solution containing about 0.22 g Zinc nitrate hexahydrate ($Zn^{+2}$) in about 40 mL 1-octanol (about 0.018 mol/L) was flowed at about 0.6 mL/hour through the bore 110 of the hollow fiber 100 while an aqueous mum solution containing about 9 g of mum in about 80 mL deionized water (DI) (about 1.37 mol/L) was poured into the reactor chamber 345 immersing the outer (shell) side surface 105 of the hollow fiber 100 while stirring the solution at about 60 rpm for about 120 minutes to provide a continuous membrane growth step. The fabrication of the hollow fiber 100 is discussed below.

The temperature of reactor module 400 was set and maintained at about 30° C.

After the 120 minute continuous membrane growth step, the flow rate of about 0.6 mL/hour through the bore 110 of the hollow fiber 100 was stopped for about 210 minutes to provide a static membrane growth step.

After the 210 minute static membrane growth step, the flow rate of about 0.6 mL/hour through the bore 110 of the hollow fiber 100 was continued for about 20 minutes to provide a second continuous membrane growth step.

After the 20 minute second continuous membrane growth step, the flow rate of about 0.6 mL/hour through the bore 110 of the hollow fiber 100 was stopped for about 210 minutes to provide a second static membrane growth step.

After the 210 minute second static membrane growth step, the reaction was stopped.

To stop the reaction, about 10 mL of neat 1-octanol solvent was flowed at about 2 mL/min through the bore 110 while the outer (shell) side surface 105 was soaked in about 70 mL of neat DI (and replaced three times) to remove the excess $Zn^{+2}$. Next, about 10 mL heptanes were flowed at about 2 mL/min through the bore 110 while the outer (shell) side surface 105 was soaked in about 70 mL heptanes to remove the 1-octanol. Next, similar procedure was performed with a more volatile hexane solution. Then, about 10 mL hexane was flowed at about 2 mL/min through the bore 110 while outer (shell) side surface 105 was soaked in about 70 mL hexane to remove the heptanes. Finally, about 20 mL of MeOH was flowed at about 2 mL/min through the bore 110 while the outer (shell) side surface 105 was soaked in about 70 mL methanol to remove the DI. The membrane was dried at about room temperature (e.g., about 25° C.) for about 2 days.

Figures 31A, 31B, 31C:
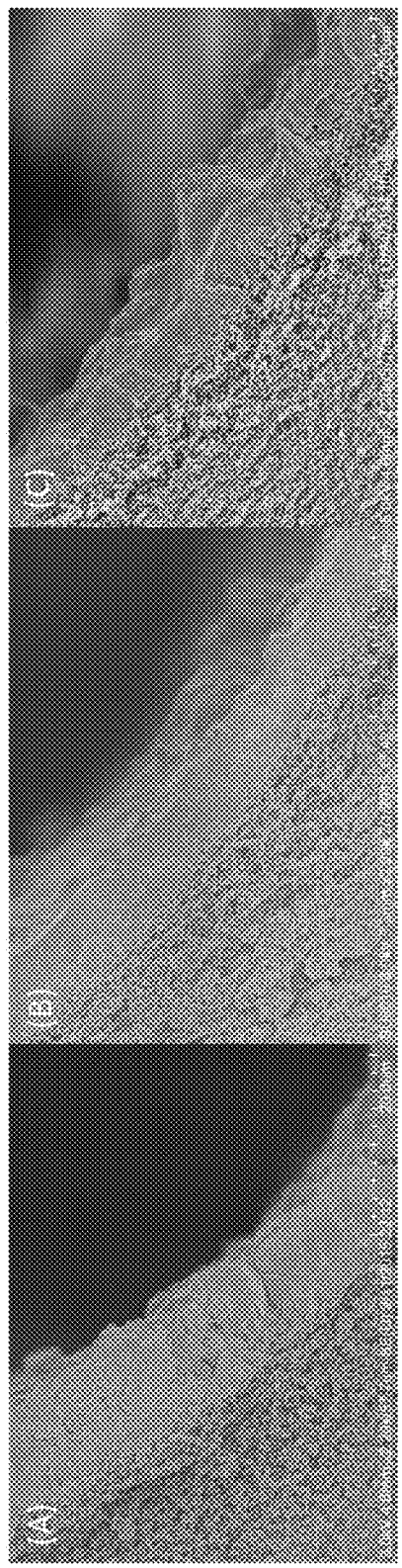
FIG. 31A illustrates exemplary cross-sectional SEM images of a ZIF-8 membrane grown on a polyamide-imide (e.g., TORLON®) hollow fiber using isothermal IMMP approach as in Case 1.
FIG. 31B illustrates exemplary cross-sectional SEM images of a ZIF-8 membrane grown on a polyamide-imide (e.g., TORLON®) hollow fiber using isothermal IMMP approach as in Case 2.
FIG. 31C illustrates exemplary cross-sectional SEM images of a ZIF-8 membrane grown on a polyamide-imide (e.g., TORLON®) hollow fiber using initial heating IMMP approach as in Case 3.

Cross-sectional views of SEM micrographs of ZIF-8 membranes grown under various IMMP process conditions are shown in FIGS. 31A-32C. FIGS. 31A-31C shows cross-sectional SEM images of the ZIF-8 membranes obtained in Cases 1, 2 and 3, depicting uniform membrane layers for each case. FIG. 32A-32C show detailed measurements of membrane thickness at different axial locations along the 5 cm length of the hollow fiber for Cases 1, 2 and 3. Notably, the membrane thickness in Case 3 (about 5 µm) is much lower than for Case 1 and Case 2 (about 10 µm, and about 9 µm, respectively) indicating that the initial heating IMMP approach remains effective in reducing the membrane thickness on the improved hollow fiber support.

The separation properties of the ZIF-8 membranes grown on the inner bore of the polyamide-imide (e.g., TORLON®) hollow fiber 100 were characterized by hydrogen($H_2$)/propane ($C_3H_8$) and propylene ($C_3H_6$)/propane ($C_3H_8$) binary equimolar mixture permeation as a function of temperature, with the reactor module 400 directly acting as a permeation cell. See FIG. 16. The separation properties of the ZIF-8 membranes were also characterized by $H_2/C_3H_6/C_3H_8$ tertiary equimolar mixture permeation as a function of temperature. In an embodiment, the feed mixture may be selected from the group consisting of hydrogen/hydrocarbons, hydrogen/propane, propylene/propane and butenes/butanes.

A steady-state Wicke Kallenbach technique was used to test binary $H_2/C_3H_8$ and $C_3H_6/C_3H_8$ and tertiary $H_2/C_3H_6/C_3H_8$ mixtures.[24] Specifically, 1:1 or 1:1:1 feed mixtures were flowed at 1 atmosphere through a bore 110 of the ZIF-8 membrane grown on the polyamide-imide (e.g., TORLON®) hollow fiber 100 at a precisely controlled flow rate (e.g., about 10 mL/minutes) via a mass flow controller (MFC) while an argon sweep gas was flowed across an outer (shell) side surface 105 of the hollow fiber 100 at about 30 mL/minute. The injected gases were contacted in a mixer before entering the feed side of the reactor/permeation module. A similar apparatus was used for measurements at higher feed pressures (up to 6 bar), except that MFCs rated for high-pressure operation were used.

An online gas chromatograph (Shimadzu GC-2014) with TCD and FID detectors was used to determine the composition of permeate.

Membrane defect characterization was performed with permporosimetry equipment with the IMMP reactor module 400 directly acting as a permeation cell. First, helium was introduced into one end of the bore 110 of the ZIF-8 membrane while plugging the other end with a Swagelok fitting. The pressure differential between the bore side 110 and the shell side 105 was, thus, controlled from 0 psi to 90 psi helium while the shell side 105 helium flow rate was measured using a digital flow meter. Then, the bore 110 of the ZIF-8 membrane was saturated with Fluorinert (FC-40) solution that has a low surface tension. Then, the shell side 105 helium flow rate was measured again.

Atomic force microscopy (AFM) images of inner surfaces of the hollow fibers were obtained with an ICON Dimension® scanning probe microscope (Bruker). The AFM was operated under tapping mode with Mikromasch NSC14 silicon cantilevers (8 nm tip radius, 5 N/m force constant, and 160 kHz typical resonance frequency).

Table 11 shows information about $C_3H_6/C_3H_8$ permeation characteristics for various IMMP processes in Cases 1, 2 and 3.

TABLE 11

Measurement of Gas Permeation Properties of In-Situ grown ZIF-8 membranes $C_3H_6/C_3H_8$ equimolar mixed gas permeance results at 25° C.

| Example | Permeance (G.P.U.) | | Selectivity |
|---|---|---|---|
| | $C_3H_6$ | $C_3H_8$ | $C_3H_6/C_3H_8$ |
| Case 1 | 27 ± 4 | 3 ± 1 | 9 ± 1 |
| Case 2 | 34 ± 4 | 1.4 ± 0.3 | 24 ± 3 |
| Case 3 | 66 ± 3 | 1.0 ± 0.1 | 65 ± 5 |

Without wishing to be bound by any theory, the inventors believe that increasing the rate of formation of the initial dense barrier layer may significantly reduce its thickness during the initial continuous membrane growth step, since a more rapidly formed barrier layer would effectively inhibit further reaction-limited dense film growth. This would result in a reduced overall membrane thickness and, hence, a higher permeance.

Performance in Membrane Synthesis Using IMMP Reactor Cell/Module: Initial Heating Starting with a fabricated polyamide-imide (e.g., TORLON®) hollow fiber mounted in the IMMP reactor module 400,[12] about 10 mL of neat 1-octanol was flowed at about 2 mL/min through a bore 110 of a hollow fiber 100 using a syringe pump. Then, about 3 mL of a Zn+2/1-octanol solution containing about 0.22 g Zinc nitrate hexahydrate ($Zn^{+2}$) in about 40 mL 1-octanol (about 0.018 mol/L) was flowed at about 0.6 mL/hour through the bore 110 of the hollow fiber 100 while an aqueous mum solution containing about 9 g of mum in about 80 mL deionized water (DI) (about 1.37 mol/L) was poured into the reactor chamber 345 immersing the outer (shell) side surface 105 of the hollow fiber 100 while stirring the solution at about 60 rpm for about 120 minutes to provide a continuous membrane growth step. The fabrication of the hollow fiber 100 is discussed above.

The temperature of the reactor module 400 was initially set at about 22° C. During the continuous membrane growth step, the temperature of the reactor module 400 was increased linearly from about 22° C. to about 42° C. in about 25 minutes (about 0.8° C./min) to increase the formation of the initial dense membrane layer. Then, the temperature of the reactor module 400 was decreased from about 42° C. to about 30° C. in about 60 minutes (about 0.2° C./min) For the remainder of the synthesis, the temperature of the reactor module was set and maintained at about 30° C.

After the 120 minute continuous membrane growth step, the flow rate of about 0.6 mL/hour through the bore 110 of the hollow fiber 100 was stopped for about 210 minutes to provide a static membrane growth step.

After the 210 minute static membrane growth step, the flow rate of about 0.6 mL/hour through the bore 110 of the hollow fiber 100 was continued for about 20 minutes to provide a second continuous membrane growth step.

After the 20 minute second continuous membrane growth step, the flow rate of about 0.6 mL/hour through the bore 110 of the hollow fiber 100 was stopped for about 210 minutes to provide a second static membrane growth step.

After the 210 minute second static membrane growth step, the reaction was stopped.

To stop the reaction, about 10 mL of neat 1-octanol solvent was flowed at about 2 mL/min through the bore 110 while the outer (shell) side surface 105 was soaked in about 70 mL of neat DI (and replaced three times) to remove the excess $Zn^{+2}$. Next, about 10 mL heptanes were flowed at about 2 mL/min through the bore 110 while the outer (shell) side surface 105 was soaked in about 70 mL heptanes to remove the 1-octanol. Next, a similar procedure was performed with a more volatile hexane solution. Then, about 10 mL hexane was flowed at about 2 mL/min through the bore 110 while outer (shell) side surface 105 was soaked in about 70 mL hexane to remove the heptanes. Finally, about 20 mL of MeOH was flowed at about 2 mL/min through the bore 110 while the outer (shell) side surface 105 was soaked in about 70 mL methanol to remove the DI. The membrane was dried at about room temperature (e.g., about 25° C.) for about 2 days.

The initial heating IMMP approach increased the rate of formation of the initial dense layer. See FIGS. 27D-27F. A considerably thinner (about 2.5 μm) dense membrane layer is formed initially, leading to thinner final membrane thickness (about 8 μm) with a correspondingly higher propylene permeance (about 33 G.P.U.) and no loss of selectivity over the isothermal case. See Tables 6 & 7.

Performance in Membrane Synthesis Using IMMP Reactor Cell/Module: Improved Hollow Fiber Support and Initial Heating Starting with a fabricated, improved polyamide-imide (e.g., TORLON®) hollow fiber mounted in the IMMP reactor module 400,[12] about 10 mL of neat 1-octanol was flowed at about 2 mL/min through a bore 110 of a hollow fiber 100 using a syringe pump. Then, about 3 mL of a Zn+2/1-octanol solution containing about 0.22 g Zinc nitrate hexahydrate ($Zn^{+2}$) in about 40 mL 1-octanol (about 0.018 mol/L) was flowed at about 0.6 mL/hour through the bore 110 of the hollow fiber 100 while an aqueous mum solution containing about 9 g of mum in about 80 mL deionized water (DI) (about 1.37 mol/L) was poured into the reactor chamber 345 immersing the outer (shell) side surface 105 of the hollow fiber 100 while stirring the solution at about 60 rpm for about 120 minutes to provide a continuous membrane growth step. The fabrication of the improved hollow fiber 100 is discussed above.

The temperature of the reactor module 400 was initially set at about 22° C. During the continuous membrane growth step, the temperature of the reactor module 400 was increased linearly from about 22° C. to about 42° C. in about 25 minutes (i.e., at about 0.8° C./min) Then, the temperature of the reactor module 400 was decreased from about 42° C. to about 30° C. in about 60 minutes (i.e., about 0.2° C./min) For the remainder of the synthesis, the temperature of the reactor module was set and maintained at about 30° C.

After the 120 minute continuous membrane growth step, the flow rate of about 0.6 mL/hour through the bore 110 of the hollow fiber 100 was stopped for about 210 minutes to provide a static membrane growth step.

After the 210 minute static membrane growth step, the flow rate of about 0.6 mL/hour through the bore 110 of the hollow fiber 100 was continued for about 20 minutes to provide a second continuous membrane growth step.

After the 20 minute second continuous membrane growth step, the flow rate of about 0.6 mL/hour through the bore 110 of the hollow fiber 100 was stopped for about 210 minutes to provide a second static membrane growth step.

After the 210 minute second static membrane growth step, the reaction was stopped.

To stop the reaction, about 10 mL of neat 1-octanol solvent was flowed at about 2 mL/min through the bore 110 while the outer (shell) side surface 105 was soaked in about 70 mL of neat DI (and replaced three times) to remove the excess $Zn^{+2}$. Next, about 10 mL heptanes were flowed at about 2 mL/min through the bore 110 while the outer (shell) side surface 105 was soaked in about 70 mL heptanes to remove the 1-octanol. Next, a similar procedure was performed with a more volatile hexane solution. Then, about 10 mL hexane was flowed at about 2 mL/min through the bore 110 while outer (shell) side surface 105 was soaked in about 70 mL hexane to remove the heptanes. Finally, about 20 mL of MeOH was flowed at about 2 mL/min through the bore 110 while the outer (shell) side surface 105 was soaked in about 70 mL methanol to remove the DI. The membrane was dried at about room temperature (e.g., about 25° C.) for about 2 days.

To compare the performance of these ZIF-8 membranes, equimolar $C_3H_6/C_3H_8$ mixed-gas permeation data were collected using a steady-state Wicke-Kallenbach technique at 25° C. with the IMMP reactor directly acting as a permeation module (see Table 11). The Case 3 ZIF-8 membrane shows much higher $C_3H_6$ permeance than the Cases 1 and 2 membranes due to a much lower thickness. Also, the Case 3 membrane also shows much higher $C_3H_6/C_3H_8$ selectivity due to a significant drop in the $C_3H_8$ permeance.

Figure 33:
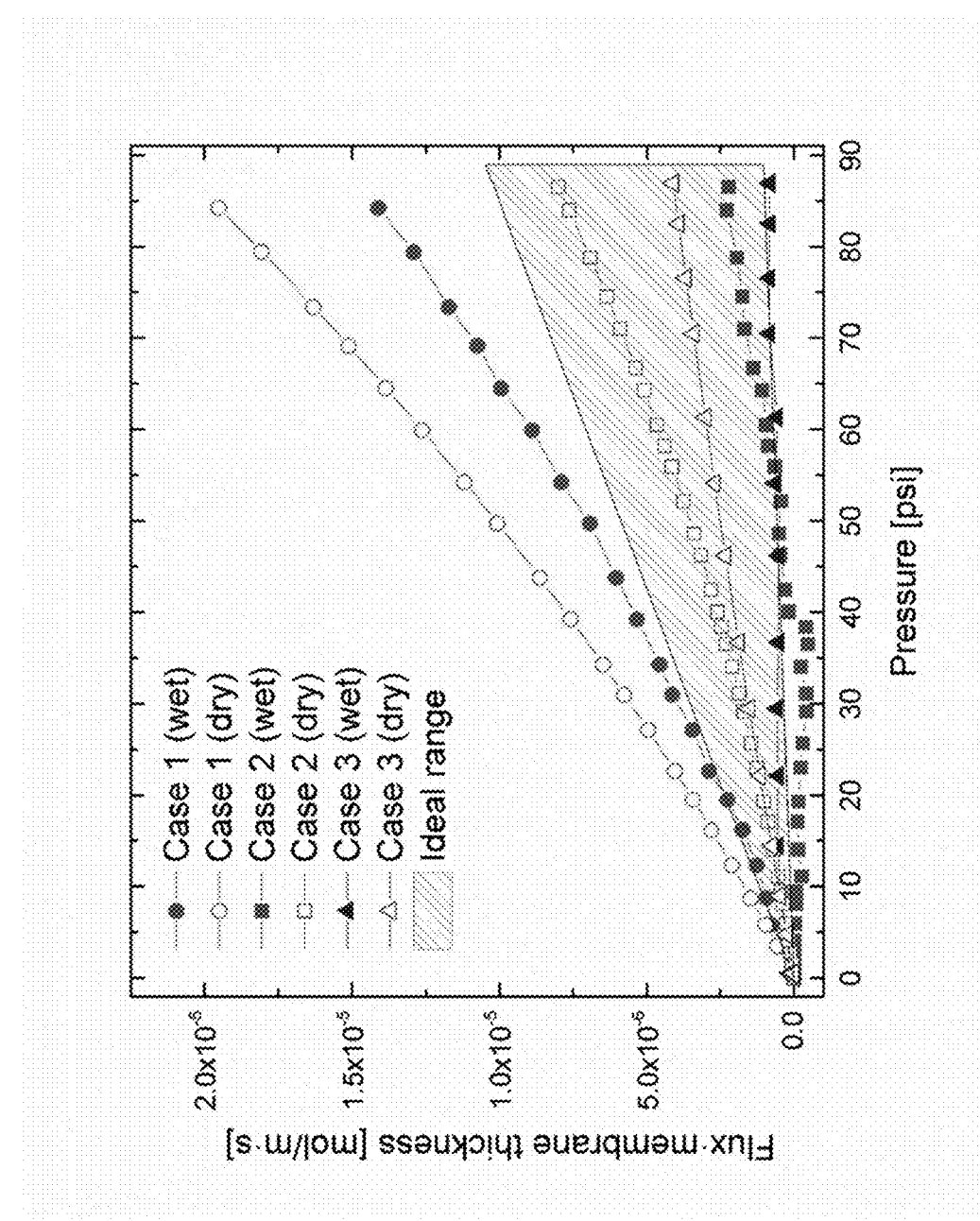
FIG. 33 illustrates a chart of Pressure (psi) vs. Flux membrane thickness (mol/m·s), showing helium permeabilities (expressed as flux×membrane thickness) measured at room temperature under dry and wetted conditions for ZIF-8 membranes grown on polyamide-imide (e.g., TORLON®) hollow fibers as in Cases 1-3.

Without wishing to be bound by any theory, the inventors believe that the ZIF-8 membrane defects are decreased due to better anchoring of the membrane layer on the more porous hollow fiber support. The microstructural changes were investigated in more detail with helium permporosimetry.[22] The helium flux was measured under dry conditions and, then, after wetting with Fluorinert (FC-40) liquid that has a low surface tension, helium permeance is measured as a function of pressure in the feed gas. Under wetted conditions, ZIF-8 membranes that have mesopore defects such as pinholes or cracks would show a sudden increment in helium permeance at a pressure that is sufficient to displace the wetting liquid from the mesopore defects. The defect size can then be estimated by the Cantor equation.[23] However, such phenomena are not observed in the pressure range 0-90 psi for any of the Case 1-3 ZIF-8 membranes (see FIG. 33), showing that continuous membrane layers are formed over the entire fiber with no large defects (i.e., defects less than 20 nm in diameter, length or width at 90 psi helium).

However, the dry helium permeabilities (see FIG. 33) also allow the qualitative characterization of nanoscopic defects (i.e., less than 20 nm). The ideal range of helium permeability from a ZIF-8 membrane free of defects is represented by the shaded area in FIG. 33, which is obtained using the range of corrected diffusivity and adsorption isotherm parameters for helium in ZIF-8 as given by Zhang et al.[24] The Case 1 ZIF-8 membranes display significantly higher dry helium permeability outside the ideal region, clearly indicating the presence of nanoscopic defects. However, the dry helium permeability progressively declines and reaches the ideal region in Case 2 and Case 3 ZIF-8 membranes, indicating that both membrane thickness and defect density have been reduced. The Case 3 ZIF-8 membrane has the lowest dry helium permeability, corresponding to the most defect-free membranes which also has the best separation performance as shown in Table 11.

Figures 34A, 34B:
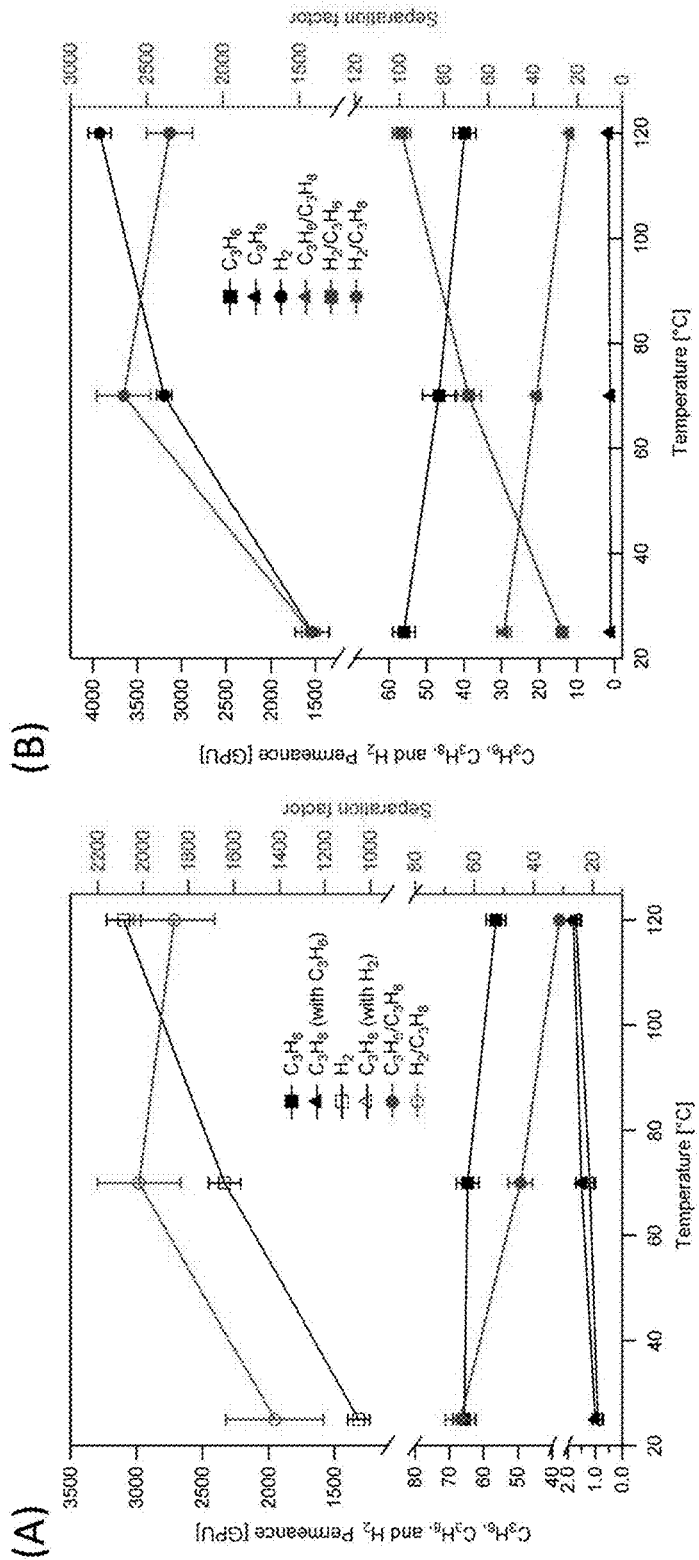
FIG. 34A illustrates a chart of Temperature (C) vs. Permeance (G.P.U.) and Separation Factor, showing binary $H_2/C_3H_8$ and $C_3H_6/C_3H_8$ permeation characteristics for an equimolar feed mixture on a ZIF-8 membrane grown on polyamide-imide (e.g., TORLON®) hollow fiber as in Case 3.
FIG. 34B illustrates a chart of Temperature (C) vs. Permeance (G.P.U.) and Separation Factor, showing ternary $H_2/C_3H_6/C_3H_8$ permeation characteristics for equimolar feed mixtures on a ZIF-8 membrane grown on polyamide-imide (e.g., TORLON®) hollow fiber as in Case 3.

Finally, the inventors characterized the binary and ternary mixture separation properties of the Case 3 ZIF-8 membranes in more detail as a function of temperature from about 25° C. to about 120° C. FIG. 34A shows equimolar binary ($H_2/C_3H_8$ and $C_3H_6/C_3H_8$) mixture permeation properties. Clear molecular sieving effects are observed for the improved ZIF-8 membranes on polyamide-imide (e.g., TORLON®) hollow fibers with $H_2/C_3H_8$ and $C_3H_6/C_3H_8$ separation factors of about 2000 at 70° C. and about 65 at 25° C., respectively. This performance is much improved from previously reported ZIF-8 membranes on polyamide-imide (e.g., TORLON®) hollow fibers with separation factors of about 370 at 120° C. and about 12 at 25° C., respectively).[25] This data shows a strong temperature dependence of the $C_3H_6$ permeance, resulting in a moderate decrease in separation factor as temperature increases. However, the ZIF-8 membranes still achieve a $C_3H_6/C_3H_8$ separation factor of about 31 G.P.U. at 120° C.

FIG. 34B shows the equimolar ternary ($H_2/C_3H_6/C_3H_8$) mixture separation properties. This feed mixture simulates the composition of an exit stream from near-equilibrium propane dehydrogenation (PDH) reactors that are used for propylene production. The Case ZIF-8 membrane continues to effectively separate $C_3H_6$ from $C_3H_8$ in the presence of $H_2$ with separation factor of about 53 at 25° C. It is also noted that these Case 3 membranes can be utilized to separate $H_2$ from $C_3H_6$ (i.e., $H_2/C_3H_6$ separation factor of 99±3 at 120° C., which industrially attractive).[19]

Further, the Case 3 ZIF-8 membrane was tested for binary $C_3H_6/C_3H_8$ separation performance at feed pressures up to 6 bar at 25° C. The selectivity remains high and shows only minor (about 13-15%) reduction at 6 bar. The $C_3H_6$ permeance shows a reduction of about 25%, which is expected in molecular sieve materials due to pore saturation effects. However, it is important to note that the actual $C_3H_6$ flux (throughput) at 6 bar is about 3.75 to 4 times higher due to the much greater driving force.

In conclusion, the mechanistic findings and resulting significant improvements in membrane performance supports a two-stage separation of ternary $H_2/C_3H_6/C_3H_8$ mixtures (e.g., a first ZIF-8 membrane stage of small total area that takes advantage of the very high $H_2$ permeance to separate it from $C_3H_6$ and $C_3H_8$, followed by a second ZIF-8 membrane stage of larger area that separates $C_3H_6$ from $C_3H_8$). Such two-stage separation is possible due to the significant advancements of the present invention, first, the modification of the IMMP approach to include an initial heating growth step and, secondly, the engineering of a modified hollow fiber support with enhanced surface properties.

In a hydrocarbon separation embodiment, the feed mixture to the reactor cell 400 comprises about 2 mol % to about 95 mol % hydrogen, about 2 mol % to about 95 mol % i-butane, about 2 mol % to about 95 mol % n-butane and mixtures thereof. For example, the feed mixture may comprise about 0 mol % to about 2 mol % ethane, about 0 mol % to about 5 mol % n-propane, about 0 mol % to about 5 mol % i-propane, about 0 mol % to about 5 mol % butenes, about 2 mol % to about 95 mol % i-butane, about 2 mol % to about 95 mol % n-butane, about 0 mol % to about 2 mol % pentenes and about 0 mol % to about 15 mol % pentanes and mixtures thereof.

In a hydrocarbon separation embodiment, an operating temperature for the reactor cell 400 is from about 30° C. to about 120° C. or any value there between. In an embodiment, the operating temperature is about 30° C. In an embodiment, the operating temperature is about 70° C. In an embodiment, the operating temperature is about 120° C.

In a hydrocarbon separation embodiment, an operating pressure for the reactor cell 400 is from about 1 bar to about 14 bar or any value there between. In an embodiment, the operating pressure is about 1 bar. In an embodiment, the operating pressure is about 4 bar. In an embodiment, the operating pressure is about 7 bar. In an embodiment, the operating pressure is about 10 bar. In an embodiment, the operating pressure is about 14 bar.

The embodiments and examples set forth herein are presented to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims. The invention is specifically intended to be as broad as the claims below and their equivalents.

Definitions

As used herein, the terms "a," "an," "the," and "said" means one or more, unless the context dictates otherwise.

As used herein, the term "about" means the stated value plus or minus a margin of error or plus or minus 10% if no method of measurement is indicated.

As used herein, the term "or" means "and/or" unless explicitly indicated to refer to alternatives only or if the alternatives are mutually exclusive.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the phrase "consisting of" is a closed transition term used to transition from a subject recited before the term to one or more material elements recited after the term, where the material element or elements listed after the transition term are the only material elements that make up the subject.

As used herein, the term "free of defects" means that the metal-organic framework (MOF) membrane coating is from about 95% to about 100% free of defects (and any range or value there between), and, preferably, from about 97% to about 100% free of defects or about 100% free of defects, and that any existing defect sizes is less than about 20 nanometer (and any range or value there between) in diameter, length or width, and, preferably, the defect sizes are less than 10 nanometers in diameter, length or width such that the membrane coating is essentially continuous to prevent gas or liquid being treated from leaking through a defect (e.g., pore, crack, void, etc.).

As used herein, the phrase "growth solvent" means a liquid in which the MOF seed crystals can be increased in size, either by crystal deposition or synthesis, but without harming the polymer.

As used herein, the term "mesoporous" means having a 3D structure of interconnected pores, wherein the pore sizes range in diameter from about 0.1 nanometer to about 10 nanometers (and any range or value there between), and, preferably, the pore sizes range in diameter from about 1 nanometer to about 5 nanometers or from about 2 nanometers to about 4 nanometers. However, the pores sizes may be varied depending on the gases to be separated.

As used herein, the phrase "nanocrystals" means the seed crystals have an average size of less than one micron, preferably about 400-600 nm, and a size distribution of about ±10%. For polymers with very small pores, a smaller seed crystal may be needed, and therefore the seed crystal size can be reduced as needed.

As used herein, the phrase "non-solvent" means a liquid in which the MOF precursors have a low solubility, such that on introducing the non-solvent to the mixture, the precursors are unable to stay in solution and condense quickly to form a large number of nuclei, which are the seeds for growing a large number of very small crystals.

As used herein, the term "polymer" means polymers made from one or more monomeric unit, and, thus, the term is intended to include polymers, copolymers, block copolymers, terpolymers and the like unless explicitly limited to specific types of polymers.

As used herein, the phrase "seed solvent" means a liquid in which the MOF nanocrystals can be carried into the pores of the polymer. Thus, the seed crystals should have low solubility in the solvent and the solvent should penetrate or wet the pores of the polymer, but without harming the polymer.

As used herein, the term "simultaneously" means occurring at the same time or about the same time, including concurrently.

As used herein, "starting material" means that the recited chemical is made or purchased for use as an early reactant in the synthetic pathway. However, if made, rather than purchased, there may be other ingredients that pre-date same.

ABBREVIATIONS

Abbreviations are used in this disclosure, as follows:

| | |
|---|---|
| AFM | Atomic force microscopy |
| DI | Deionized water |
| DLS | Dynamic light scattering |
| EDS | Energy dispersive X-ray spectroscopy |
| $H_2$ | Hydrogen |
| IMMP | Interfacial Microfluidic Membrane Processing |
| mIm | 2-methyl imidazole |
| MOF | Metal organic framework |
| PDMS | Poly(dimethylsiloxane) |
| $C_3H_8$ | Propane |
| C3H6 | Propylene |
| SEM | Scanning electron microscope |
| SPM | Scanning probe microscopy |
| XRD | X-ray diffraction |
| ZIF | Zeolitic imidazolate framework |
| ZIF-8 | Zeolitic imidazolate framework 8 |
| ZIF-90 | Zeolitic imidazolate framework 90 |

INCORPORATION BY REFERENCE

All patents and patent applications, articles, reports, and other documents cited herein are fully incorporated by reference to the extent they are not inconsistent with this invention, as follows:
1) J. Gascon, et al., CHEM. MATER. 24 (2012) 2829-2844.
2) K. Varoon, et al., SCIENCE 334(6052) (2011) 72-75.
3) M. Shah, et al., IND. ENG. CHEM. RES. 51 (2012) 2179-2199.
4) M. G. Buonomenna, RSC ADVANCES 3 (2013) 5694-5740.

5) M. Tsapatsis, Science 334(6057) (2011) 767-768.
6) T. Cao, et al., Science 334(6062) (2011) 1533-1538.
7) J. Choi, et al., Science 325(5940) (2009) 590-593.
8) Y. Pan, et al., J. Membr. Sci. 421-422 (2012) 292-298.
9) J. A. Thompson, et al., Chem. Mater. 24 (2012) 1930-1936.
10) K. S. Park, et al., Proc. Natl. Acad. Sci. U.S.A. 103(27) (2006) 10186-10191.
11) A. Huang, et al., J. Am. Chem. Soc. 132(44) (2010) 15562-15564.
12) A. J. Brown, et al., Angela. Chem. 124 (2012) 10767-10770.
13) R. Ameloot, et al., Nat. Chem. 3 (2011) 382-387.
14) M. Pera-Titus, et al., J. Membr. Sci. 278 (2006) 401-409.
15) K. Li, et al., J. Am. Chem. Soc. 131(30) (2009) 10368-10369.
16) K. S. Jang, et al., Chem. Mater. 23 (2011) 3025-3028.
17) Y. Pan, et al., J. Membr. Sci. 390-391 (2012) 93-98.
18) H. Bux, et al., Chem. Mater. 23 (2011) 2262-2269.
19) Y. Pan, Z. Lai, Chem. Commun. 47(37) (2011) 10275-10277.
20) H. T. Kwon, et al., Chem. Commun. 49 (2013) 3854-3856.
21) H. S. Khare, et al., Polymer 51 (2010) 719-729.
22) W. S. Rasband, "ImageJ", U.S. National Institutes of Health, Bethesda Md., USA.
23) D. Korelskiy, et al., J. Membr. Sci. 417-418 (2012) 183-192.
24) J. Kärger, et al., Diffusion in Zeolites and Other Microporous Solids (Wiley, 1992).
25) J. I. Calvo, et al., J. Colloid & Interface Sci. 176(2) (1995) 467-478.
26) C. Zhang, et al., J. Phys. Chem. Lett. 3(16) (2012) 2130-2134.
27) A. J. Brown, et al., S. Nair, Science 345(6192) (2014) 72-75.

What is claimed is:

1. A reactor cell for flow processing molecular sieving membranes, comprising:
    a reactor module having a base shape and a first height, wherein the base shape is selected from the group consisting of square, rectangular, circular and ellipse; wherein a reactor chamber extends into the reactor module from an upper surface; wherein a first hole extends into the reactor chamber from a first surface, a second hole opposing the first hole extends into the reactor chamber from a second surface, a third hole extends into the reactor chamber from a third surface and a fourth hole opposing the third hole extends into the reactor chamber from a fourth surface; wherein the first hole is fluidically connected to a first inlet, the second hole is fluidically connected to a first outlet, the third hole is fluidically connected to a second inlet and the fourth hole is fluidically connected to a second outlet;
    a reactor module cover having the same base shape as the reactor module and a second height, wherein the reactor module cover is fastened to the reactor module to seal the reactor chamber; and
    a hollow fiber having a first end and a second end, wherein a length of the first end is supported by and sealed into the first hole and a length of the second end is supported by and sealed into the second hole; wherein the first and second ends of the hollow fiber are capped with a capping solution, wherein a molecular sieving membrane that is uniform and at least 95% free of defects is grown on an inner bore surface of the hollow fiber.

2. The device of claim 1, wherein the molecular sieving membrane is at least about 97% free of defects and wherein any defects are less than about 20 nm in diameter, length or width.

3. The device of claim 1, wherein the molecular sieving membrane is at least about 97% free of defects and wherein any defects are less than about 10 nm in diameter, length or width.

4. The device of claim 1, wherein the first hole extends into the reactor chamber from the first surface, the second hole opposing the first hole extends into the reactor chamber from the second surface, the third hole extends into the reactor chamber from the first surface and the fourth hole opposing the third hole extends into the reactor chamber from the second surface.

5. The device of claim 1, wherein the first hole extends into the reactor chamber from the first surface, the second hole opposing the first hole extends into the reactor chamber from the second surface, the third hole extends into the reactor chamber from an upper surface of a reactor module cover and the fourth hole opposing the third hole extends into the reactor chamber from a bottom surface of the reactor chamber.

6. The device of claim 1, wherein the lengths of the first and second ends of the hollow fiber are sealed into the first and second holes with an adhesive.

7. The device of claim 1, wherein the capping solution is about 8 wt % to about 10 wt % poly(dimethylsiloxane) (PDMS) in heptane.

8. A method of making a reactor cell device, the reactor cell device comprising
    a reactor module having a base shape and a first height, wherein the base shape is selected from the group consisting of square, rectangular, circular and ellipse; wherein a reactor chamber extends into the reactor module from an upper surface; wherein a first hole extends into the reactor chamber from a first surface, a second hole opposing the first hole extends into the reactor chamber from a second surface, a third hole extends into the reactor chamber from a third surface and a fourth hole opposing the third hole extends into the reactor chamber from a fourth surface; wherein the first hole is fluidically connected to a first inlet, the second hole is fluidically connected to a first outlet, the third hole is fluidically connected to a second inlet and the fourth hole is fluidically connected to a second outlet;
    a reactor module cover having the same base shape as the reactor module and a second height, wherein the reactor module cover is fastened to the reactor module to seal the reactor chamber; and
    a hollow fiber having a first end and a second end, wherein a length of the first end is supported by and sealed into the first hole and a length of the second end is supported by and sealed into the second hole; wherein the first and second ends of the hollow fiber are capped with a capping solution, wherein a molecular sieving membrane that is uniform and at least 95% free of defects is grown on an inner bore surface of the hollow fiber,
making the reactor cell device comprising the steps of:
    fabricating the reactor chamber extending into the reactor module from the upper surface of the reactor module;
    fabricating an O-ring groove with an inner dimension slightly larger than and offset from the outer dimension of the reactor chamber;

fabricating the first hole extending into the reactor chamber from the first surface and the second hole opposing the first hole and extending into the reactor chamber from the second surface;

fabricating a third hole extending into the reactor chamber from a third surface and a fourth hole opposing the third hole and extending into the reactor chamber from a fourth surface;

supporting and sealing the length of the first end of the hollow fiber in the first hole and the length of the second end of the hollow fiber into the second hole;

capping the first and second ends of the hollow fiber with a capping solution;

fabricating the reactor module cover to fit on the upper surface of the reactor module and fastening the reactor module cover to the seal the reactor chamber;

fluidly connecting a bore solution to the first inlet;

fluidly connecting a shell solution to the second inlet; and growing the molecular sieving membrane that is uniform and at least about 95% free of defects on an inner bore surface of the hollow fiber.

9. The method of claim 8, wherein the molecular sieving membrane is at least about 97% free of defects and wherein any defects are less than about 20 nanometers in diameter, length or width.

10. The method of claim 8, wherein the molecular sieving membrane is at least about 97% free of defects and wherein any defects are less than about 10 nanometers in diameter, length or width.

11. The method of claim 8, wherein the bore solution contains a limited $Zn+2$ concentration ranging from about 0.005 to about 0.1 mol/L $Zn+2$ in 1-octanol.

12. The method of claim 8, wherein the bore solution contains a limited $Zn+2$ concentration ranging from about 0.01 to about 0.03 mol/L $Zn+2$ in 1-octanol.

13. The method of claim 8, wherein the bore solution is about 0.018 mol/L $Zn+2$ in 1-octanol.

14. The method of claim 8, wherein the shell solution contains an excess mum ligand concentration ranging from about 0.5 to about 10 mol/L 2-methyl imidazole (mum) in deionized water.

15. The method of claim 8, wherein the shell solution contains an excess mum ligand concentration ranging from about 1.2 to about 1.6 mol/L 2-methyl imidazole (mum) in deionized water.

16. The method of claim 8, wherein the shell solution is about 1.37 mol/L mum in deionized water.

17. The method of claim 8, further comprising the step of gently stirring the shell solution to prevent formation of local concentration gradients.

18. The method of claim 14, wherein the shell solution is stirred at about 40 rpm to about 80 rpm.

19. The method of claim 8, further comprising the steps of
a. flowing the bore solution at a first flow rate for a first period, wherein a first temperature is increased to a second temperature during a portion of the first period;
b. stopping the first flow rate of the bore solution for a second period;
c. flowing the bore solution at a second flow rate for a third period; and
d. stopping the second flow rate of the bore solution for a fourth period.

20. The method of claim 19, wherein the second temperature is decreased to a third temperature during a portion of the first period.

21. The method of claim 19, wherein the first and second flow rates are about 1 µL/hour to about 1000 µL/hour per individual hollow fiber.

22. The method of claim 19, wherein the first and second flow rates are about 10 µL/hour to about 100 µL/hour per individual hollow fiber.

23. The method of claim 19, wherein the first period is about 1 hour to about 3 hours, the second period is about 3 hours to about 4 hours, the third period is about 10 minutes to about 30 minutes, and the fourth period is about 3 hours to about 4 hours.

24. The method of claim 19, further comprising the step of rinsing the membrane in solvents selected from the group consisting of 1-octanol, heptanes, hexane, methanol and deionized water.

25. A method of using a reactor cell device, comprising:
providing a reactor cell device of claim 8,
fluidically connecting a feed mixture to the first inlet;
fluidically connecting a sweep gas to the second inlet;
collecting a separated mixture from the first outlet; and
collecting permeate from the second outlet.

26. The method of claim 25, wherein the feed mixture to the device is selected from the group consisting of hydrogen/hydrocarbons, hydrogen/propane, propylene/propane and butenes/butanes.

27. The method of claim 25, wherein the feed mixture to the device is selected from the group consisting of hydrogen/propane, propylene/propane and butenes/butanes.

28. The method of claim 26, wherein the feed mixture to the device comprises about 2 mol % to about 95 mol % i-butane, about 2 mol % to about 95 mol % n-butane and mixtures thereof.

29. The method of claim 25, wherein an operating temperature for the device is from about 30° C. to about 95° C. or any value there between.

30. The method of claim 25, wherein an operating pressure for the device is from about 1 bar to about 14 bar or any value there between.

* * * * *